United States Patent [19]
Hirsh et al.

[11] Patent Number: 6,001,820
[45] Date of Patent: Dec. 14, 1999

[54] COMPOSITIONS AND METHODS FOR INHIBITING THROMBOGENESIS

[75] Inventors: Jack Hirsh, Hamilton; Jeffrey I. Weitz, Ancaster, both of Canada

[73] Assignee: Hamilton Civic Hospitals Research Development Inc., Canada

[21] Appl. No.: 08/870,528

[22] Filed: Jun. 6, 1997

Related U.S. Application Data

[63] Continuation-in-part of application No. 08/624,327, Mar. 29, 1996, Pat. No. 5,763,427, which is a continuation-in-part of application No. 08/540,324, Oct. 6, 1995, Pat. No. 5,744,457, which is a continuation-in-part of application No. 08/412,332, Mar. 31, 1995, abandoned.

[51] Int. Cl.$^6$ .......................... A61K 31/725; C08B 37/10
[52] U.S. Cl. .............................. 514/56; 514/54; 514/921; 536/21; 536/122; 536/123.1; 536/124
[58] Field of Search ................................ 514/54, 56, 921; 536/21, 122, 123.1, 124

[56] References Cited

U.S. PATENT DOCUMENTS

| | | | |
|---|---|---|---|
| 4,281,108 | 7/1981 | Fussi | 536/21 |
| 4,351,938 | 9/1982 | Barnett | 536/21 |
| 4,496,550 | 1/1985 | Lindahl et al. | 514/54 |
| 4,500,519 | 2/1985 | Lormeau et al. | 514/56 |
| 4,629,699 | 12/1986 | Bianchini | 435/101 |
| 4,687,765 | 8/1987 | Vairel et al. | 514/56 |
| 4,791,195 | 12/1988 | Bianchini | 536/21 |
| 4,847,338 | 7/1989 | Linhardt et al. | 536/54 |
| 4,916,219 | 4/1990 | Linhardt et al. | 536/21 |
| 4,933,326 | 6/1990 | Bianchini et al. | 514/56 |
| 4,942,156 | 7/1990 | Foley et al. | 514/56 |
| 4,981,955 | 1/1991 | Lopez | 536/21 |
| 4,990,502 | 2/1991 | Lormeau et al. | 536/55.3 |
| 5,010,063 | 4/1991 | Piani et al. | 514/56 |
| 5,013,724 | 5/1991 | Petitou et al. | 514/54 |
| 5,019,649 | 5/1991 | Lormeau et al. | 536/21 |
| 5,039,529 | 8/1991 | Bergendahl et al. | 424/630 |
| 5,084,564 | 1/1992 | Vila et al. | 536/21 |
| 5,106,734 | 4/1992 | Nielsen | 435/84 |
| 5,236,910 | 8/1993 | Egidio et al. | 514/56 |
| 5,547,944 | 8/1996 | Mascellani et al. | 514/54 |

FOREIGN PATENT DOCUMENTS

| | | |
|---|---|---|
| 101 141 | 2/1984 | European Pat. Off. |
| 121 067 | 4/1987 | European Pat. Off. |
| 244 235 | 11/1987 | European Pat. Off. |
| 048 231 | 6/1988 | European Pat. Off. |
| 337 327 | 10/1989 | European Pat. Off. |
| 214 879 | 11/1990 | European Pat. Off. |
| 496 233 | 7/1992 | European Pat. Off. |
| 511 075 | 10/1992 | European Pat. Off. |
| 513 513 | 11/1992 | European Pat. Off. |
| 355 905 | 1/1993 | European Pat. Off. |
| 293 539 | 6/1994 | European Pat. Off. |
| 287 477 | 11/1994 | European Pat. Off. |
| 623 629 | 11/1994 | European Pat. Off. |
| WO 82/01005 | 4/1982 | WIPO |
| WO 82/03627 | 10/1982 | WIPO |
| WO 90/01501 | 2/1990 | WIPO |
| WO 90/04607 | 5/1990 | WIPO |
| WO 90/04970 | 5/1990 | WIPO |
| WO 91/15217 | 10/1991 | WIPO |
| WO 92/02232 | 2/1992 | WIPO |
| WO 92/11294 | 7/1992 | WIPO |
| WO 92/17187 | 10/1992 | WIPO |
| WO 92/17188 | 10/1992 | WIPO |
| WO 92/17506 | 10/1992 | WIPO |
| WO 92/18545 | 10/1992 | WIPO |
| WO 93/05074 | 3/1993 | WIPO |
| WO 93/16112 | 8/1993 | WIPO |
| WO 93/19737 | 10/1993 | WIPO |
| WO 94/12618 | 6/1994 | WIPO |
| WO 95/12403 | 5/1995 | WIPO |

OTHER PUBLICATIONS

Alhenc–Gelas, et al., "Laboratory Control of Low–Molecular–Weight Heparins: Needs and Possibilities," *Fundamental and Clinical Cardiology*, 19:43–54 (1994).

Atha, et al., "Physicochemical Characterization of Low Molecular Weight Heparin," *J. Pharm. Sciences*, 84(3):360–364 (1995).

Barzu, et al., "O–Acylated heparin derivatives with low anticoagulant activity decrease proliferation and increase α–smooth muscle active expression in cultured arterial smooth muscle cells," *Euro. J. Pharm.*, 219:225–233 (1992).

Barzu, et al., "Preparation and Anti–HIV Activity of O–Acylated Heparin and Dermatan Sulfate Derivatives with Low Anticoagulant Effect," *J. Med. Chem.*, 36:3546–3555 (1993).

Cifonelli, et al., "The Distribution of 2–Acetamido–2–Deoxy–D–glucose residues in Mammalian Heparins," *Charbo. Res.*, 21:173–186 (1972).

Doctor, et al., "Anticoagulant Properties of Semisynthetic Polysaccharide Sulfates," *Thrombosis Research*, 64:413–425 (1991).

(List continued on next page.)

*Primary Examiner*—Kathleen K. Fonda
*Attorney, Agent, or Firm*—Townsend and Townsend and Crew LLP

[57] ABSTRACT

The present invention provides compositions and methods for the treatment of cardiovascular diseases. More particularly, the present invention relates to modifying thrombus formation by administering an agent which, inter alia, is capable of (1) selectively inactivating thrombin which is bound either to fibrin in a clot or to some other surface, but which has only minimal inhibitory activity against free thrombin, i.e., fluid-phase thrombin; (2) inhibiting the assembly of the intrinsic tenase complex, thereby inhibiting the activation of Factor X by Factor IXa; and (3) inhibiting the activation of Factor IX by Factor XIa. The compositions and methods of the present invention are particularly useful for preventing thrombosis in the circuit of cardiac bypass apparatus and in patients undergoing renal dialysis, and for treating patients suffering from or at risk of suffering from thrombus-related cardiovascular conditions, such as unstable angina, acute myocardial infarction (heart attack), cerebrovascular accidents (stroke), pulmonary embolism, deep vein thrombosis, arterial thrombosis, etc.

45 Claims, 23 Drawing Sheets

OTHER PUBLICATIONS

Horton, et al., The Nitrous Acid Deamination of Glycosides and Acetates of 2–Amino–2–Deoxy–D–Glucose, *Charbo. Res.*, 30:367–374 (1973).

Jordan, et al., "The Kinetics of Hemostatic Enzyme–Antithrombin Interactions in the Presence of Low Molecular Weight Heparin," *J. of Biol. Chem.*, 255(21):10081–10090 (1980).

Lagunoff, et al., "Determination of 2–Deopxy–2–Sulfoaminohexose Content of Mucopolysaccharides," *Archives of Biochem. and Biophys.*, 99:396–400 (1962).

Linhardt, et al., "Oligosaccharide Mapping of Low Molecular Weight Heparins: Structure and Activity Differences," *J. Med. Chem.*, 33:1639–1645 (1990).

Mascellani, et al., Active Sites of Dermatan Sulfate for Heparin Cofactor II. Isolation of a Nonasaccharide Fragment Containing Four Disaccharide Sequences [α–L–Iduronic Acid 2–O–Sulfate (1,3)–β–D–N–Acetylgalactosamine 4–Sulfate], *J. Carbohydrate Chem.*, 14(8):1165–1177 (1995).

Mattsson, et al., "Antithrombotic Effects of Heparin Oligosaccharides," *Annals of the N.Y. Acad. Sci.*, 556:323–332 (1989).

Nagase, et al., "Depolymerized Holothurian Glycosaminoglycan With Novel Anticoagulant Actions: Antithrombin III—and Heparin Cofactor II–Independent Inhibition of Factor X Activation by Factor IXa–Factor VIIIa Complex and Heparin Cofactor II–Dependent Inhibition of Thrombin," *Blood*, 85(6):1527–1534 (1995).

Schoen, et al., "The Effect of Sulfation of the Anticoagulant and Antithrombin III–Binding Properties of a Heparin Fraction with Low Affinity for Antithrombin III," *Thrombosis Research*, 57:415–423 (1990).

Shimotori, et al., "Comparative Studies of Heparin Cofactor Activity Toward Antithrombin III and Heparin Cofactor II, and Antithrombin III Affinity Between Low Molecular Weight heparin and Unfractionated Heparin," *Seminars in Thrombosis and Hemostasis*, 16 (supp.):71–76 (1990).

Shively, et al., "Formation of Anhydrosugars in the Chemical Depolymerization of Heparin," *Biochemistry*, 15(18):3932–3942 (1976).

Shively, et al., "Nearest Neighbor Analysis of Heparin: Identification and Quantitation of the Products Formed by Selective Depolymerization Procedures," *Biochemistry*, 15(18):3943–3950 (1976).

Shively, et al., "Stoichiometry of the Nitrous Acid Deaminative Cleavage of Model Amino Sugar Glycosides and Glycosaminoglycuronans," *Biochemistry*, 9(1):33–43 (1970).

Svahn, et al., "Inhibition of angiogenesis by heparin fragments in the presence of hydrocortisone," *Carbohydrate Polymers*, 18:9–16 (1992).

Tollefsen, et al., "Effect of Low Molecular Weight Heparin Preparations on the Inhibition of Thrombin by Heparin Cofactor II," *Seminars in Thrombosis and Hemostasis*, 16 (supp.):66–70 (1990).

Weitz, et al., "New Anticoagulant Strategies," *J. Lab. Clin. Med.*, 122(4):364–373 (1993).

Cade, et al., "A Comparison of the Antithrombotic and Haemorrhagic Effects of Low Molecular Weight Heparin Fractions: The Influence of the Method of Preparation," *Thrombosis Research*, 35:613–625 (1984).

The Merck Index, Twelfth Edition; S. Budavari et al., eds.; Merck & Co., Inc., 1996, Whitehouse Station, New Jersey; monograph 4685.

** HEPARIN AND LMWH INHIBIT; VASOFLUX DOES NOT INHIBIT.

*** VASOFLUX INHIBITS; HEPARIN AND LMWH DO NOT INHIBIT.

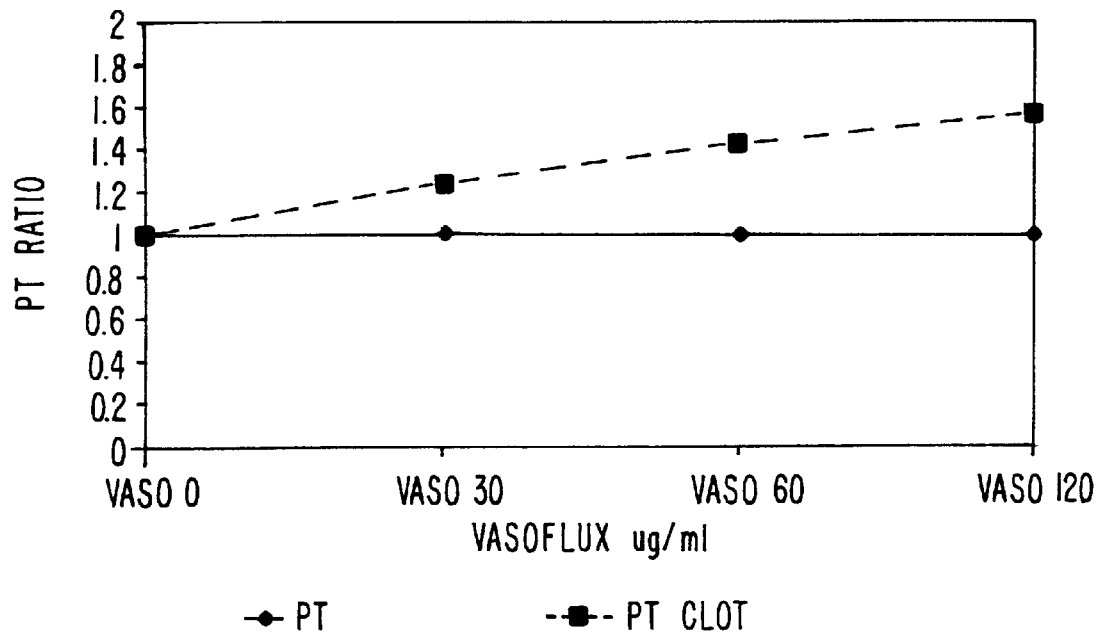
FIG. IIA.
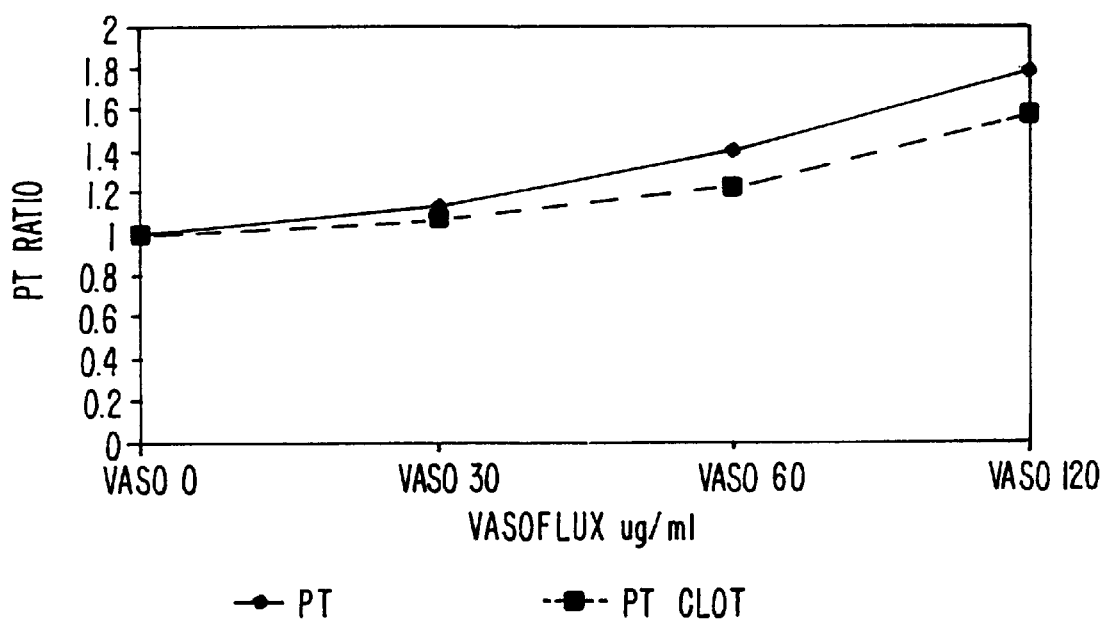
FIG. IIB.

| LMWH ug/mlU | NORMAL RATIO | IX DEF RATIO |
|---|---|---|
| 0 | 1.0 | 1.0 |
| 8 | 1.25 | 1.25 |
| 15 | 1.6 | 1.9 |
| 30 | 2.5 | 2.8 |

| HEPARIN NU/ml | NORMAL RATIO | IX DEF RATIO |
|---|---|---|
| 0 | 1.0 | 1.0 |
| 0.1 | 1.1 | 1.1 |
| 0.2 | 1.4 | 1.3 |
| 0.3 | 1.8 | 1.5 |

FIG. 14.

| CONTROL PLASMA | | FACTOR IX DEFICIENT | |
|---|---|---|---|
| NO CLOT | CLOT | NO CLOT | CLOT |
| 50 SECS | 39 SECS | 44 SECS | 32 SECS |
| 50 SECS | 39 SECS | 43 SECS | 32 SECS |
| 42 SECS | 38 SECS | 45 SECS | 33 SECS |
| 50 SECS | 36 SECS | 46 SECS | 33 SECS |
| MEAN 48 SECS | MEAN 38 SECS | MEAN 44.5 SECS | MEAN 32.5 SECS |

FIG. 13.

COMPOSITIONS AND METHODS FOR INHIBITING THROMBOGENESIS

RELATED APPLICATIONS

This application is a continuation-in-part of Ser. No. 08/624,327, filed Mar. 29, 1996, now U.S. Pat. No. 5,763,427, which is a continuation-in-part of Ser. No. 08/540,324, filed Oct. 6, 1995, now U.S. Pat. No. 5,744,457, which is a continuation-in-part of Ser. No. 08/412,332, filed Mar. 31, 1995, now abandoned, the teachings of all of which are incorporated herein by reference.

FIELD OF THE INVENTION

The present invention relates generally to compositions and methods for the treatment of cardiovascular disease. More particularly, the present invention relates to modifying thrombus formation and growth by administering an agent which, inter alia, is capable of (1) selectively inactivating thrombin which is bound either to fibrin in a clot or to some other surface, but which has only minimal inhibitory activity against free thrombin, i.e., fluid-phase thrombin; (2) inhibiting the assembly of the intrinsic tenase complex, thereby inhibiting the activation of Factor X by Factor IXa; and (3) inhibiting the activation of Factor IX by Factor XIa. The invention also relates to heparin cofactor II-specific (HCII) catalytic agents, the activity of which allows them to (1) inactivate fibrin-bound thrombin, (2) inhibit the assembly of the intrinsic tenase complex and, in turn, the activation of Factor X by Factor IXa, and (3) inhibit the activation of Factor IX by Factor XIa in a patient at concentrations which produce minimal inactivation of free thrombin, thereby diminishing the risk of bleeding. In addition, the present invention provides methods and compositions useful for treating cardiovascular disease.

BACKGROUND OF THE INVENTION

Blood coagulation is a process consisting of a complex interaction of various blood components, i.e., factors, which eventually gives rise to a fibrin clot. Generally, the blood components which participate in what has been referred to as the coagulation "cascade" are proenzymes or zymogens, i.e., enzymatically inactive proteins which are converted to proteolytic enzymes by the action of an activator which is, itself, an activated clotting factor. Coagulation factors that have undergone such a conversion are generally referred to as "active α factors," and are designated by the addition of a lower case "a" suffix (e.g., Factor VIIa).

Activated Factor X ("Xa") is required to convert prothrombin to thrombin, which then converts fibrinogen to fibrin as a final stage in forming a fibrin clot. There are two systems, i.e., pathways, that promote the activation of Factor X. The "intrinsic pathway" refers to those reactions that lead to thrombin formation through utilization of factors present only in plasma. A series of protease-mediated reactions ultimately generates Factor IXa which, in conjunction with Factor VIIIa, cleaves Factor X into Xa. An identical proteolysis is effected by Factor VIIa and its co-factor, tissue factor, in the "extrinsic pathway" of blood coagulation. Tissue factor is a membrane bound protein and does not normally circulate in plasma. Upon vessel disruption, however, it can complex with Factor VII or Factor VIIa to catalyze Factor X activation or Factor IX activation in the presence of $Ca^{2+}$ and phospholipid. While the relative importance of the two coagulation pathways in hemostasis is unclear, Factors IX activation by the Factor VIIa-tissue factor complex has, in recent years, been found to play a pivotal role in the initiation of the normal clotting response. However, Factor IX activation in response to tissue factor exposed at sites of vascular injury has also been implicated in thrombosis, a pathological manifestation of the clotting cascade in blood vessels.

Thrombosis, which can complicate rupture of an atherosclerotic plague, can cause partial or total occlusion of the affected blood vessel, thereby leading to a number of important cardiovascular complications, including unstable angina, acute myocardial infarction (heart attack), or cerebral vascular accidents (stroke). Vessel injury and/or stasis can trigger venous thrombosis causing deep vein thrombosis and subsequent pulmonary embolism. Such diseases are a major cause of disability and mortality throughout the world, but particularly in Western societies. Moreover, thrombin and, in particular, surface-bound thrombin plays a role in thrombus formation in cardiac bypass circuits, after angioplasty and during and after thrombolytic therapy for acute myocardial infarction. Therefore, patients undergoing these procedures must be treated with very high doses of anticoagulants or antithrombin agents. Although high doses of these agents may effectively prevent clotting, they can give rise to serious bleeding complications.

The clot or thrombus, which forms as a result of activation of the clotting cascade, contains fibrin, platelets and numerous other blood components. Thrombin bound to fibrin remains active and causes growth of the clot by continued cleavage of fibrinogen and activation of platelets and other coagulation factors, such as Factor V and factor VIII. Moreover, unlike free thrombin which is readily inactivated by naturally occurring anti-thrombins (e.g., antithrombin III (ATIII)), clot-bound thrombin is protected from inactivation. As a result, the clot acts as a reservoir for active thrombin which triggers further clot growth. In addition, thrombin also induces smooth cell proliferation and, thus, may be involved in proliferative responses, such as graft-induced atherosclerosis and restenosis after angioplasty or atherectomy.

Because thrombin is critical to thrombus formation, the use of thrombin inhibitors for treating thrombosis and thrombotic complications has long been proposed. A number of partially effective inhibitors have been in use for years. Heparin, for example, can be used as an anticoagulant and antithrombin agent to inhibit fibrin formation, platelet aggregation and thrombus formation. Heparin, however, has a number of limitations. For example, it has biophysical limitations because it acts as an anticoagulant by activating ATIII and, thus, it is relatively ineffective at inactivating fibrin-bound thrombin at safe doses, thereby allowing the continued growth of thrombus mediated by thrombin bound to fibrin in the pre-existing thrombus. In addition, the doses required to produce an antithrombotic effect are quite unpredictable and, therefore, the dosage must be monitored closely. Low molecular weight heparins (LMWHs) can also be used as anticoagulants and anti-thrombin agents to inhibit fibrin formation, platelet aggregation and thrombus formation. LMWHs act by activating ATIII and, as such, have the same biophysical limitations as heparin. However, LMWHs produce a more predictable anticoagulant effect than heparin. Thus, both heparin and LMWH have the limitation of not readily inactivating surface-bound thrombin. The consequences of this are (a) high concentrations are needed to achieve an anti-thrombin effect which can lead to excessive bleeding, and (b) once the agents are cleared from the circulation, the surface-bound thrombin can reactivate clotting.

Inactivation of clot-bound thrombin may be achieved with another set of compounds known as direct thrombin inhibitors. Such inhibitors include hirudin and its derivatives, and inhibitors of the active site of thrombin, such as argatroban and PPACK (D-phenylalanyl-L-propyl-L-arginyl chloromethyl ketone). Hirudin is an anti-thrombin substance extracted from the salivary glands of leeches. Related compounds include hirulog which is a small, synthetic analog of hirudin. While these drugs are able to inhibit clot-bound thrombin, they have the following limitations. First, they do not typically inactivate clot-bound thrombin selectively, but do so at the same concentrations which are required to inhibit free thrombin. Secondly, their inactivation of thrombin is generally stoichiometric and, thus, unless very high concentrations are used, the inhibitory effect can be overcome by the large amounts of thrombin that are generated at sites where surface-bound thrombin accumulates (e.g., on bypass circuits, or at sites of arterial or venous thrombosis). As a result of the above two limitations, high concentrations of direct thrombin inhibitors (e.g., hirudin) must typically be administered to interact with and inhibit the free thrombin generated by clot-bound thrombin. Such high inhibitor concentrations can, however, cause unwanted bleeding. Moreover, direct thrombin inhibitors (e.g., hirudin, its analogs and small molecule active site thrombin inhibitors, such as argatroban) are generally reversible and, thus, their inhibitory effect is lost when the drugs are cleared from the blood. Unfortunately, this reversible inhibition can lead to rebound activation of coagulation.

In addition, inactivation of clot-bound thrombin may be achieved with a third class of compounds which bind reversibly or irreversibly to the active, i.e., catalytic, site of thrombin. PPACK is an example of an irreversible active site inhibitor. Such inhibitors, however, generally lack sufficient specificity for thrombin and, thus, have questionable safety. For example, PPACK also inactivates tissue type plasminogen activator, the major initiator of clot lysis. Thus, PPACK administration could trigger thrombosis by blocking the major pathway for clot degradation. Moreover, inhibitors such as PPACK have the same limitation as hirudin in that they typically have equal activity against clot-bound and free thrombin. This is problematic because evidence indicates that total inhibition of free thrombin using irreversible active site inhibitors may lead to excessive bleeding.

Moreover, other anticoagulant and antithrombin agents have been described in the literature. For instance, hirudin derivatives for blocking the active site of thrombin are described in U.S. Pat. Nos. 5,240,913 and 5,196,404. A bifunctional anti-thrombotic composition which includes both a glycoprotein IIb/IIIa inhibitory domain and a thrombin inhibitory domain is described in WO 92/10575. Peptide analogs of glycoprotein IIIa for thrombogenesis inhibition are described in WO 90/00178. Inhibitors of factor X and/or Xa are described in U.S. Pat. Nos. 5,239,058 and 5,189,019, and PCT publications WO 93/09803, WO 92/04378 and WO 92/01464. Inhibitors of factors VII and/or VIII are described in U.S. Pat. Nos. 5,223,427 and 5,023,236 and WO 92/06711. Platelet anti-adhesives and related antibodies are described in WO 92/08472. For a review of the structure and function of thrombin, see, Stubbs and Bode, *Thrombosis Research* 69:1–58 (1993).

In addition, numerous modified heparin compositions, as well as other glycosaminoglycans and their derivatives, have been developed. For example, U.S. Pat. Nos. 5,296,471, 5,280,016 and 5,314,876 describe the desulfation of heparin, periodate oxidation of heparin/heparan sulfates followed by reduction of resulting aldehyde groups, and high molecular mass N,O-sulfated heparosans, respectively. Low molecular weight heparin fractions have been used for several years (see, Boneu, et al., *Thrombosis Research* 40:81–89 (1985)). More recently, various dermatan sulfates have been developed and their interactions with heparin cofactor II studied (see, Mascellani, et al., *Thrombosis Research* 74:605–615 (1994), and Sheehan, et al., *J. Biol. Chem.* 289:32747–32751 (1994)). For a review of the limitations of heparin and the potential advantages of new anticoagulants as anti-thrombotics, see, Hirsh, *Circ.* 88:I-C (1993).

In view of the foregoing, there remains a need in the art for improved compositions and methods that are useful, for example, for inhibiting thrombogenesis associated with cardiovascular disease. An ideal antithrombotic agent would be one which can pacify the clot by inactivating fibrin-bound thrombin at concentrations which do not produce abnormal bleeding resulting from inhibition of thrombin production in the general circulation and/or which can selectively block the coagulation cascade at a desirable point. The present invention fulfills these and other needs.

SUMMARY OF THE INVENTION

The present invention provides compositions and methods for the treatment of cardiovascular diseases. More particularly, the present invention relates to modifying thrombus formation and growth by administering an agent which, inter alia, is capable of (1) selectively inactivating thrombin which is bound either to fibrin in a clot or to some other surface, but which has only minimal inhibitory activity against free thrombin, i.e., fluid-phase thrombin; (2) inhibiting the assembly of the intrinsic tenase complex, thereby inhibiting the activation of Factor X by Factor IXa; and (3) inhibiting the activation of Factor IX by Factor XIa. By modulating fibrin-bound thrombin, Factor Xa generation and Factor IX activation, the agents of the present invention are effective at modifying thrombus formation and, thus, are invaluable as antithrombotic agents.

More particularly, the agents of the present invention are capable of selectively inactivating clot-bound thrombin. In one aspect, the present invention provides heparin cofactor II-specific (HCII) catalytic agents capable of selectively inactivating thrombin which is bound either to fibrin in a clot or to some other surface, but which has only minimal inhibitory activity against free thrombin. The selective activity of the HCII-specific catalytic agents of the present invention allows them to inactivate fibrin-bound thrombin in a patient at concentrations which produce minimal inactivation of free thrombin, thereby diminishing the risk of bleeding. Preferably, the inactivation of fibrin- or surface-bound thrombin is essentially irreversible so that clot accretion will not substantially resume after such HCII-specific catalytic agents (i.e., activating agents which activate, catalyze or induce HCII-mediated inactivation of fibrin-bound thrombin) are cleared from the blood.

Moreover, the agents of the present invention are capable of disrupting or inhibiting the assembly of the intrinsic tenase complex and, in turn, the activation of Factor X by Factor IXa. More particularly, the process of blood coagulation occurs on the platelet surface as a result of the assembly of a number of the coagulation factors on the surface of activated platelets. For instance, in the presence of calcium, Factor IXa complexes with platelet-bound Factor VIIIa to form the intrinsic tenase complex which activates Factor X to Factor Xa. In the presence of calcium, Factor Xa forms a complex with Factor Va on the platelet surface (i.e., the prothombinase complex) which, in turn, converts prothrombin to thrombin. Surprisingly, it has been discovered that the agents of the present invention are capable of disrupting the assembly of the intrinsic tenase complex, thereby inhibiting the activation of Factor X by Factor IXa. In studying the mechanism by which the agents of the present invention impair the assembly of the intrinsic tenase complex, it was found that the agents have a marked inhibitory effect of Factor Xa generation induced by either Factor IXa or XIa.

In addition, it has also surprisingly been found that the agents of the present invention are capable of prolonging the activated partial thromboplastin time (APTT) assay without exhibiting appreciable anti-factor Xa or anti-thrombin activity. Moreover, it has been found that this effect on the APTT is to a large extent independent of HCII and ATIII. The ability of the agents of the present invention to interfere with the assembly of the intrinsic tenase complex explains, in part, some of the HCII- and ATIII-independent effects of the agents of the present invention on the APTT. The ability of the agents of the present invention to interfere with the intrinsic tenase complex assembly is extremely important in that it confers on such agents the ability to passivate activated platelets in addition to the ability to inactivate thrombin bound to thrombin.

In one embodiment, the agents of the present invention are low molecular weight heparin (LMWH) preparations that have been modified so that they contain less than about 5% and, more preferably, less than about 3% of the anti-thrombin III (ATIII) catalyzing activity or, interchangeably, activating activity of unmodified LMWH or standard heparin, but more ATIII activating activity than dermatan sulfate. Moreover, because of their reduced chain length compared to standard heparin, the agents of the present invention have much less activity as catalysts of HCII-mediated inactivation of free thrombin than either standard heparin or dermatan sulfate. As such, the agents of the present invention have very little activity when assayed against free thrombin in a thrombin clotting time assay and would not have been predicted to be effective anti-thrombotic agents. Quite surprisingly, as explained above, the agents of the present invention are able to effectively catalyze HCII-mediated inactivation of surface-bound thrombin, e.g., fibrin-bound thrombin or, interchangeably, clot-bound thrombin.

Surface-bound thrombin is typically inactivated through the formation of a covalent, irreversible thrombin-HCII complex. Thus, in contrast to typical anti-thrombins and other anticoagulants (e.g., dermatan sulfate, heparin, low molecular weight heparins (LMWHs), hirudin and other direct thrombin inhibitors), the HCII-specific catalytic agents of the present invention have the ability to selectively and, preferably, irreversibly inactivate fibrin-bound thrombin without having major inhibitory effects against fluid-phase thrombin. Without being bound to a given theory, this ability is explained by the observation that the agents of the present invention produce a conformational change in HCII which enables it to bind thrombin effectively when the enzyme is immobilized on a surface, but which lacks the chain length necessary to bridge thrombin to HCII effectively when thrombin is free in the fluid phase.

The agents of the present invention can be used in various methods, for example, to modify thrombus formation in a patient without inducing a clinically unsafe increase in systemic bleeding by, for example, (1) selectively inactivating clot-bound thrombin with only minimal inactivation of free thrombin, (2) inhibiting the assembly of the intrinsic tenase complex, thereby inhibiting the activation of Factor X by Factor IXa, and/or (3) inhibiting the activation of Factor IX by Factor XIa. Such methods generally comprise administering to a patient a pharmacologically acceptable dose of an agent of the present invention. Such agents are preferably characterized by a specific anti-factor IIa activity mediated by heparin cofactor II of about 2 to about 5 units/mg in an anti-factor IIa assay, an antithrombin III catalyst specific activity of about 0.2 to about 1.5 units/mg in an anti-factor Xa assay, and a solubility in aqueous media ranging from about 150 to about 1,000 mg/ml. Moreover, such agents have the ability to impair the assembly of the intrinsic tenase complex by having a marked inhibitory effect on Factor Xa generation induced by either Factor IXa or XIa. In addition, such agents have an anticoagulant effect which is contributed to by both an HCII- and ATIII-mediated mechanism, and by a mechanism which is independent of both HCII and ATIII. Such agents are preferably polyanionic carbohydrates of less than about 24 monosaccharide units, typically derived from heparin preparations, having molecular weights of between about 3,000 and 8,000 Daltons (±1,000 Daltons).

The present invention includes heparin preparations which can be prepared from heparin using a variety of techniques. In one embodiment, heparin, i.e., standard, unfractionated heparin, is first reduced in molecular size by chemical depolymerization and the fractions with molecular weights ranging from 3,000 to 8,000 Daltons (±1,000 Daltons) are isolated and pooled. In a presently preferred embodiment, heparin is depolymerized using nitrous acid. Thereafter, the resulting low molecular weight heparin is chemically modified to reduce its affinity for antithrombin III. This can be accomplished chemically or, alternatively, through the use of an antithrombin III affinity column. In a presently preferred embodiment, this is accomplished chemically by an oxidation reaction followed by a reduction reaction. In this preferred embodiment, the resulting low affinity, low molecular weight heparin is a mixture of heparin molecules having a native sugar (e.g., a uronic acid residue) as the nonreducing terminal and a 2,5-anhydromannitol residue as the reducing terminal, and having molecular weights ranging from about 3,000 to about 8,000 Daltons. In this embodiment, it is believed that the reduction in molecular size together with the reduction in ATIII activating activity endows the agents of the present invention with their ability to selectively inactivate clot-bound thrombin with only minimal inactivation of free thrombin.

As an alternative to being heparin preparations, the agents of the present invention can be, for example, negatively charged polysaccharides other than heparin, negatively charged polyanions, electronegative organic molecules with an affinity for HCII, and the like. Such substances will typically bind to HCII with an affinity of at least $10^{-6}$ M, preferably at least about $10^{-8}$ M or stronger, but with weak affinity for thrombin, preferably weaker than about $10^{-6}$ M.

As desired, and depending on the use, pharmaceutical compositions useful for inhibiting thrombogenesis without substantially inhibiting normal coagulation in a patient can be prepared, the compositions comprising:

i) about 90 to about 99.9 weight percent of an agent which is capable of (1) selectively inhibiting clot-bound thrombin with only minimal inactivation of free thrombin, (2) inhibiting the assembly of the intrinsic tenase complex, thereby inhibiting the activation of Factor X by Factor IXa, and/or (3) inhibiting the activation of Factor IX by Factor XIa; and ii) about 0.1 to about 10 weight percent of an ATIII catalytic agent or, interchangeably, an ATIII activating agent, such as heparin or low molecular weight heparin (LMWH), capable of inactivating fluid phase thrombin. In a presently preferred embodiment, the agent is an HCII-specific catalytic agent that has minimal affinity for, or is essentially devoid of, ATIII binding affinity and is capable of non-inactivating fibrin-bound thrombin. In a presently preferred embodiment, the HCII catalytic activity or, interchangeably, the HCII activating activity of the, optionally blended, composition is about 2 to 5 units/mg and, more preferably, about 1 to 4 units/mg.

In another embodiment, the present invention provides a method for inhibiting clot-bound thrombin, assembly of the intrinsic tenase complex (i.e., Factor Xa generation by Factor IXa and/or Factor IXa generation by Factor XIa) and fluid-phase thrombin in a patient without inducing a clinically unsafe increase in systemic bleeding, the method comprising the step of administering to the patient a pharmacologically acceptable dose of (i) an HCII-specific catalytic agent capable of inactivating clot-bound thrombin and blocking the assembly of the intrinsic tenase complex, the HCII-specific catalytic agent having minimal affinity for antithrombin III (ATIII) and a HCII specific activity against HCII of about 2 to about 5 units/mg in an anti-factor IIa assay; and (ii) an ATIII catalytic, i.e., activating, agent capable of inactivating fluid-phase thrombin. ATIII activating agents suitable for use in this method include, but are not limited to, heparin and low molecular weight heparin. In this method, the HCII-specific catalytic agent and the ATIII catalytic agent, i.e., ATIII activating agent, can be administered to the patient either simultaneously or sequentially. When administered to the patient simultaneously, the HCII-specific catalytic agent and the ATIII catalytic agent can be administered as a single solution or compound or, alternatively, as two different solutions or compounds.

In another embodiment, the present invention provides a product comprising (i) an agent of the invention capable of inactivating clot-bound thrombin and the assembly of the intrinsic tenase complex; and (ii) an ATIII catalytic agent capable of inactivating fluid-phase thrombin as a combined preparation for simultaneous, separate or sequential use for inhibiting clot-bound thrombin, the assembly of the intrinsic tenase complex and fluid-phase thrombin in a patient, preferably without inducing a clinically unsafe increase in systemic bleeding. ATIII catalytic agents suitable for use in this product include, but are not limited to, heparin and low molecular weight heparin. In this product, the thrombin and intrinsic tenase complex inactivating agent and the ATIII catalytic agent can be for administration to the patient simultaneously. When administered to the patient simultaneously, the thrombin and intrinsic tenase complex inactivating agent and the ATIII catalytic agent can be administered as a single solution or compound or, alternatively, as two different solutions or compounds.

As explained above, preferred agents of the invention are obtainable from heparin. One class of products included in the invention comprises such preferred agents and, as a separate sub-class, the heparin preparations of the present invention, which products in both sub-classes have non-sulfated uronic acid residues in open-ring form and are substantially free of aldehyde groups. Exemplary members of the class have about 30% of their uronic acid residues in open ring form. Another class of such preferred agents and heparin preparations comprises products having a native sugar (e.g., a uronic acid residue) as the nonreducing terminal and a 2,5-anhydromannitol residue as the reducing terminal. Some particularly preferred products belong to both the aforesaid classes.

Another aspect of the invention resides in a polyanionic carbohydrate capable of selectively inactivating clot-bound thrombin in favor of free thrombin and of inhibiting the assembly of the intrinsic tenase complex, the polyanionic carbohydrate obtainable from heparin and having its non-sulfated uronic acid residues in open-ring form and substantially free of aldehyde groups.

Also provided by the invention is a product capable of (1) selectively inhibiting clot-bound thrombin, and (2) inactivating the assembly of the intrinsic tenase complex (i.e., inhibiting Factor Xa generation by Factor IXa and/or Factor IXa generation by Factor XIa), the product being an HCII-specific catalytic agent obtainable by:

(i) depolymerizing standard unfractionated heparin by nitrous acid depolymerization;

(ii) oxidizing the depolymerized heparin with sodium periodate in an aqueous medium for 24 hour at 4° C., and stopping the oxidation reaction by the addition of excess ethylene glycol followed by extensive dialysis against distilled water using dialysis tubing with a 500 MW cut off.

(iii) reducing the oxidized product by the addition of sodium borohydride and, after allowing the reaction mixture to stand for 25 hours at 23° C., adjusting the pH of the reaction mixture to 3.0 with HCl to destroy excess borohydride then quickly increasing the pH to 7.0 by the addition of NaOH;

(iv) dialyzing the resultant product extensively against distilled water; and (v) recovering the product by lyophilization; and optionally (vi) passing the product over an anti-thrombin III affinity column.

Typically, the product obtained will have the following properties: (a) a molecular weight of from 3,000 to 8,000 (±1,000); (b) a specific activity of about 2 to about 5 anti-Factor IIa (thrombin) units/mg; and (c) a specific activity of less than about 1.5 anti-factor IIa units/mg.

In a further aspect, there is provided a process for preparing an HCII-specific catalytic agent having a native non-reducing sugar as one end group and a 2,5-anhydromannitol non-reducing sugar as the other end group, the process comprising:

(i) depolymerizing unfractionated heparin;

(ii) oxidizing the resultant low molecular weight heparin; and (iii) reducing the oxidized, low molecular weight heparin; wherein the process optionally includes additional purification or other procedures to obtain said HCII-specific catalytic agent.

The products and agents of the invention are preferably for pharmaceutical use. The invention therefore includes the use for the manufacture of a medicament for the treatment of a cardiovascular disease of any of the products or agents of the invention, such as, for example, an agent for (1) activating HCII mediated inhibition of thrombin to the exclusion of significant ATIII mediated inhibition of thrombin, (2) impairing the assembly of the intrinsic tenase complex, thereby inhibiting the activation of Factor X by Factor IXa, and/or (3) inhibiting the activation of Factor IX by Factor XIa. Other products and agents of the invention which may be so used include the HCII-specific catalytic agents, LMWH preparations, polyanionic carbohydrates and products obtainable as aforesaid and product V18 described in the Examples (or a substantially similar product to V18), as well as substances having substantially the same characteristics or inhibitory or pharmacological properties as the aforesaid products and agents.

The invention further includes the use for the manufacture of a medicament for the treatment of thrombosis by prophylaxis or therapy of a heparin derivative having its non-sulfated uronic acid residues in open-ring form and substantially free of aldehyde groups.

In addition to the foregoing, pharmaceutical compositions are provided comprising an agent or product which binds to HCII and allows it to interact with a non-fibrin-binding site on thrombin. The present invention further provides pharmaceutical compositions comprising an HCII-specific catalytic agent and an ATIII catalytic agent, i.e., an ATIII activating agent, and compositions comprising an agent for selectively inactivating surface-bound or clot-bound thrombin and an inhibitor of thrombin in the fluid phase. Such pharmaceutical compositions, which may be in the form of blends, are useful for treating numerous cardiovascular conditions. In addition, such compositions are useful in conjunction with conventional thrombolytic treatments, such as the administration of tissue plasminogen activator (tPA), streptokinase, and the like, as well as with intravascular intervention, such as angioplasty, atherectomy, and the like.

A further understanding of the nature and advantages of the invention will become apparent by reference to the remaining portions of the specification and drawings.

BRIEF DESCRIPTION OF THE DRAWINGS

FIGS. 11a and 11b illustrate the effects of V18 and heparin, respectively, on the dilute PT ratio in the presence and absence of a clot in normal plasma.

FIG. 13 compares the dilute PT in control plasma with that in Factor IX-deficient plasma.

FIG. 14 illustrates the effect of heparin and LMWH on the dilute PT in normal and Factor IX deficient plasma.

DETAILED DESCRIPTION OF THE INVENTION AND PREFERRED EMBODIMENTS

Figure 1:
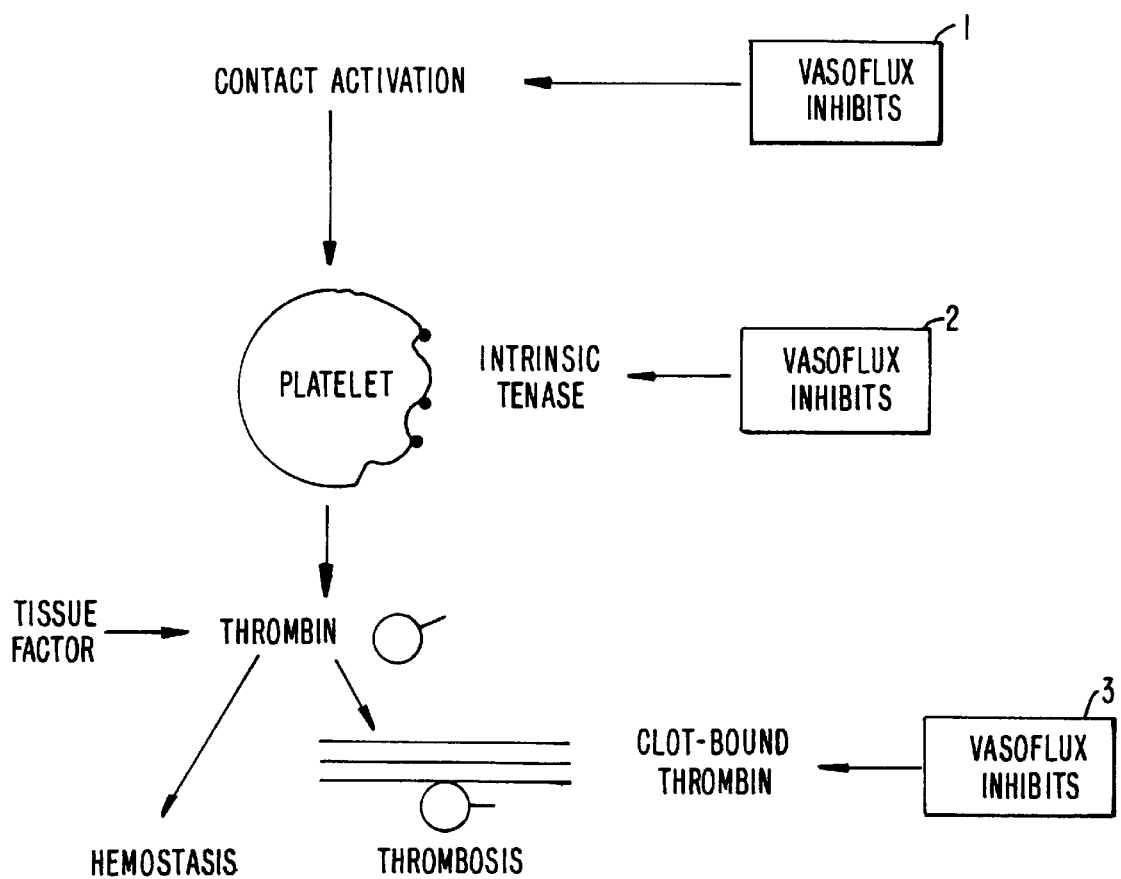
FIG. 1 illustrates three of the unique mechanisms exhibited by V18. The first is the selective inactivation of fibrin-bound thrombin through a HCII-mediated mechanism, and the second and third impair factor Xa generation through the intrinsic pathway.
Figure 2:
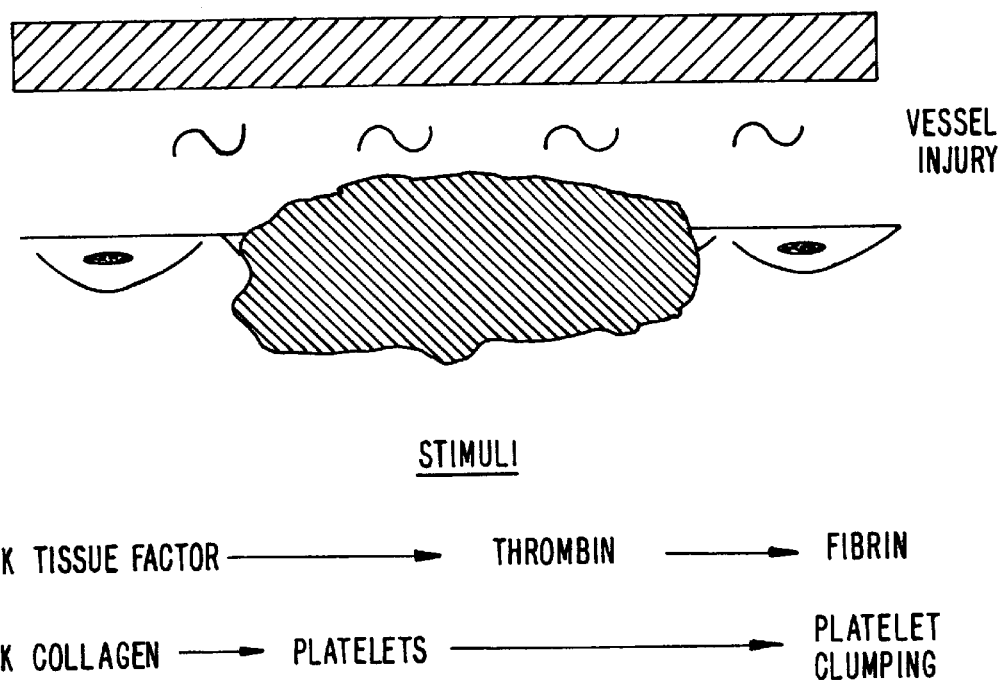
FIGS. 2 and 3 illustrate the differences in stimuli in thrombosis and hemostasis.

The present invention provides compositions and methods for the treatment of cardiovascular diseases. More particularly, the present invention relates to modifying thrombus formation and growth by administering an agent which, inter alia, is capable of (1) selectively inactivating thrombin which is bound either to fibrin in a clot or to some other surface, but which has only minimal inhibitory activity against free thrombin, i.e., fluid-phase thrombin; (2) inhibiting the assembly of the intrinsic tenase complex, thereby inhibiting the activation of Factor X by Factor IXa; and (3) inhibiting the activation of Factor IX by Factor XIa. By modulating fibrin-bound thrombin, Factor Xa generation by Factor IXa and Factor IX activation by Factor XIa, the agents of the present invention are effective at modifying thrombus formation and, thus, are invaluable antithrombotic agents.

As such, the compositions and methods of the present invention are particularly useful for preventing thrombosis in the circuit of cardiac bypass apparatus and in patients undergoing renal dialysis, and for treating patients suffering from or at risk of suffering from thrombus-related cardiovascular conditions, such as unstable angina, acute myocardial infarction (heart attack), cerebrovascular accidents (stroke), pulmonary embolism, deep vein thrombosis, arterial thrombosis, etc. The present invention is not limited to such uses, however, and the compositions and methods described herein may find use in other in vitro and in vivo situations whenever it is desirable to inhibit clot or thrombus accretion, or to promote clot or thrombus solubilization. For example, the compositions of the present invention may be used as an anticoagulant for inhibiting thrombin-induced clotting in various in vitro studies, assays and the like.

"Proteoglycan," as used herein, includes reference to a protein to which is attached one or more glycosaminoglycan chains. Proteoglycans are polyanionic compounds that have properties that reflect both the protein and the glycosaminoglycan chains.

"Glycosaminoglycan," as used herein, includes reference to a polysaccharide composed of repeating disaccharide units. The disaccharides always contain an amino sugar (i.e., glucosamine or galactosamine) and one other monosaccharide, which may be a uronic acid (i.e., glucuronic acid or iduronic acid) as in hyaluronic acid, heparin, heparan sulfate, chondroitin sulfate or dermatan sulfate—or a galactose as in keratin sulfate. The glycosaminoglycan chain may be sulfated on either moiety of the repeating disaccharide. With the exception of hyaluronic acid, all glycosaminoglycans are covalently attached to a "core protein," i.e., they occur as proteoglycans.

"Heparin" (or, interchangeably, "standard heparin" (SH) or "unmodified heparin"), as used herein, includes reference to a mixture of polysaccharide chains composed of repeating disaccharides made up of a uronic acid residue (D-glucuronic acid or L-iduronic acid) and a D-glucosamine and residue. Many of these disaccharides are sulfated on the uronic acid residues and/or the glucosamine residue. Generally, heparin has a molecular weight ranging from about 6,000 Daltons to 20,000 Daltons, depending on the source of the heparin and the methods used to isolate it. The structural formula of the repeating disaccharide units of heparin is generally as follows:

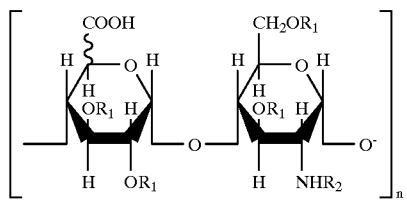

In the above formula, the "squiggle" bond at C5–C6 of the uronic acid indicates that the uronic acid may be either D-glucuronic acid (carboxyl up) or L-iduronic acid (carboxyl down). In addition, $R_1$ may be either H or $SO_3$, and $R_2$ may be H, Ac (acetyl) or $SO_3$.

A "heparin preparation," as used herein, includes reference to a preparation prepared from standard, unfractionated heparin. In a preferred embodiment, the HCII-specific catalytic agents of the present invention are modified heparins which have been prepared from standard, unfractionated heparin using the following chemical reactions: (1) nitrous acid depolymerization of unfractionated heparin to yield low molecular weight heparin (LMWH); (2) oxidation of the resulting LMWH to open the ring structures the unsulfated uronic acid moieties using, for example, sodium periodate; and (3) reduction of the oxidized LMWH to reduce the aldehydes (to alcohols) formed during the depolymerization and oxidation steps using, for example, sodium borohydride.

"Low Molecular Weight Heparin" (LMWH), as used herein, includes reference to a heparin preparation having a molecular weight of about 3,000 Daltons to about 8,000 Daltons.

"Low Affinity Heparin" (LAH) (or, interchangeably, "low affinity standard heparin" (LASH)), as used herein, includes reference to a heparin preparation which binds to antithrombin III (ATIII) with an affinity of about $10^{-6}$ M, preferably weaker than about $10^{-5}$ M.

"Low Affinity-Low Molecular Weight Heparin" (LA-LMWH), as used herein, includes reference to a heparin preparation having a molecular weight of about 3,000 Daltons to about 8,000 Daltons and which binds to ATIII with an affinity of about $10^{-6}$ M, preferably weaker than about $10^{-5}$ M. The LA-LMWH preparation can be a mixture of heparin molecules having molecular weights ranging from 3,000 to 8,000 Daltons (±1,000 Daltons). This mixture of LA-LMWH molecules is generally referred to herein as V18 or, interchangeably, as L18. Alternatively, the mixture of heparin molecules can be separated into its various components using, for example, gel exclusion chromatography. The LA-LMWH mixture can be arbitrarily separated into three LA-LWMH fractions by gel exclusion chromatography. Fraction 1 has a mean molecular weight of about 8,000 Daltons, Fraction 2 has a mean molecular weight of about 5,000 Daltons and Fraction 3 has a mean molecular weight of about 3,000 Daltons.

"Heparan Sulfate" (HS), as used herein, includes reference to a glycosaminoglycan which contains a disaccharide repeat unit similar to that of heparin, but which has more N-acetyl groups, fewer N-sulfate groups, and a lower degree of O-sulfate groups.

"Dermatan Sulfate" (DS), as used herein, includes reference to a heterogeneous glycosaminoglycan that contains disaccharide repeat units consisting of N-acetyl-D-galactosamine and D-glucuronic acid and disaccharide repeat units consisting of N-acetyl-D-galactosamine and L-iduronic acid. The uronic acids are present with variable degrees of sulfation.

"Hirudin," as used herein, includes reference to an antithrombin substance that is extracted from the salivary glands of leeches. "Hirulog," as used herein, includes reference to a small, synthetic analog of hirudin.

"Monosaccharide," as used herein, refers a polyhydroxy alcohol containing either an aldehyde or a ketone group, i.e., a simple sugar. Monosaccharide includes reference to naturally occurring simple sugars as well as simple sugars which have been chemically modified. Modified monosaccharides include, but are not limited to, monosaccharides that have increased or decreased sulfation or which have modified carboxyl, amino or hydroxyl groups. Monosaccharides may be chemically modified by: N-desulfation (see, e.g., Inoue, Y., et al., *Carbohydrate Res.* 46, pp. 87–95 (1976)); N-resulfation (see, e.g., Lloyd, A. G., et al., *Biochem. Pharmacol.* 20, pp. 637–648 (1971)), N-acetylation (see, e.g., Danishefsky, I., et al., *Biophys.* 90, pp. 114–121 (1970)); N-succinylation (see e.g., Nagasawa, K., et al., *J. Biochem.* 81, pp. 989–993 (1977)); N-deacetylation (see, e.g., Dimitriev, B. A., et al., *Carbohydr. Res.* 40, pp. 365–372 (1975)); O-desulfation (see, e.g., Jacobson, I., et al., *J. Biol. Chem.* 255, pp. 5084–5100 (1980); carboxy reduction; methylation of free hydroxyl or amino groups, etc.

"Polysaccharide," as used herein, refers a linear or branched polymer of more than 10 monosaccharides that are linked by means of glycosidic bonds.

"Polyanion," as used herein, refers a molecule that possesses a large number of negative charges. "Polyanionic carbohydrates," as used herein, includes reference to carbohydrates that possess a large number of negative charges.

A "heparin additive," as used herein, includes reference to heparin or a heparin-like compound which is mixed with an agent of the present invention prior to patient administration. In a presently preferred embodiment, the heparin additive is either unfractionated heparin or the lowest third molecular weight fraction isolated from unfractionated heparin.

"Vicinal alcohol groups," as used herein, includes reference to two hydroxyl groups on adjacent carbon atoms. More particularly, "vicinal alcohol groups" is used herein to refer to the two hydroxyl groups on the C2 and C3 carbon atoms of the heparin preparations of the present invention.

"Oxidizing agent" or, interchangeably, "oxidant," as used herein, includes reference to a substance that (1) yields oxygen readily, (2) removes hydrogen from a compound, or (3) attracts negative electrons. Suitable oxidizing reagents include, but are not limited to, sodium periodate and, under reaction conditions known to those of skill in the art, lead tetraacetate.

"Reducing agent" or, interchangeably, "reducer," as used herein, includes reference to a substance that is readily oxidized by reducing another substance. Suitable reducing agents include, but are not limited to, sodium borohydride, other metal hydrides and, under reaction conditions known to those of skill in the art, lithium aluminum hydride.

"Affinity," as used herein, is expressed in terms of the dissociation constant ($K_d$). As such, each time an affinity is mentioned, it is referring to the $K_d$, not the $K_a$.

"A clinically unsafe increase in systemic bleeding," as used herein, includes, in preferred embodiments, reference to an activated clotting time of greater than 400 seconds and a thrombin clotting time of greater than 100 seconds.

The "anti-factor IIa or antithrombin assay," as used herein, is an HCII catalytic assay that is carried out as follows: a fixed amount of human thrombin (factor IIa) is added to plasma containing a chromogenic synthetic thrombin substrate. After incubation with the compound of interest, the amount of residual thrombin activity is determined by measuring the absorbance at 405 nm.

The "anti-factor Xa assay," as used herein, is an ATIII catalytic assay that is carried out as follows: a fixed amount of factor Xa is added to plasma to which additional ATIII may or may not be added (additional ATIII is often added to ensure that ATIII is not limiting in the reaction mixture) containing a chromogenic synthetic factor Xa substrate. After incubation with the compound of interest, the amount of residual factor Xa activity is determined by measuring the absorbance at 405 nm.

As explained herein, the agents of the present invention are able to:

1) catalyze HCII-mediated inactivation of fibrin-bound thrombin, while having minimal effects on inactivation of fluid-phase thrombin, either through an HCII- or ATIII-mediated mechanism;

2) disrupt or block the assembly of the intrinsic tenase complex, thereby impairing the activation of Factor X by Factor IXa; and 3) impair factor IX activation by Factor XIa.

The above three properties, among others, render the agents of the present invention unique among antithrombotic agents and provide such agents with potential advantages over other antithrombotic agents.

With respect to the first of the above three properties, it has been demonstrated that the fibrin-binding site on thrombin (anion-binding exosite 2) is distinct from the fibrinogen-binding site on thrombin (anion-binding exosite 1). That is, when thrombin is bound to fibrin, as is the case in clot or thrombus matrices, the fibrin-binding site will be occupied, while the fibrinogen-binding site remains sterically available to bind fibrinogen and orient the bound fibrinogen for interaction with the thrombin catalytic site which promotes the conversion of fibrinogen to fibrin. The enzyme's active site and exosite 1 are available to bind and cleave other substrates as well, including factor V, factor VIII and the thrombin receptor on platelets.

Thus, it is possible to disrupt or interfere with binding between the fibrin-binding site on the thrombin and/or the thrombin-binding site on the fibrin in order to release thrombin from the clot or thrombus into a surrounding aqueous environment, usually into blood in the vascular environment. While fibrin-bound thrombin in the clot or thrombus is protected from inactivation by heparin and endogenous anti-proteinases, thrombin released from the clot or thrombus becomes susceptible to inactivation from endogenous anti-proteinases and/or appropriate drug therapies.

It is known that free thrombin, i.e., fluid-phase thrombin, is irreversibly inactivated by two plasma inhibitors, antithrombin III (ATIII) and heparin cofactor II (HCII), with ATIII being the primary inhibitor. Both of these inhibitors exhibit a markedly increased activity in the presence of certain classes of sulfated polysaccharides. It has been found that the activity of ATIII is catalyzed by heparin and by low molecular weight heparin (LMWH), whereas the activity of HCII is catalyzed by high concentrations of heparin and by dermatan sulfate. However, although heparin (but not LMWH) is a potent catalyst of HCII, the predominant effect of heparin at therapeutic concentrations is as a catalyst of ATIII, because heparin has a higher affinity for ATIII than HCII. Moreover, the plasma concentration of ATIII is more than twice that of HCII (2.4 $\mu$M and 1 $\mu$M, respectively) and, thus, heparin catalyzes both ATIII and HCII only when it is administered in very high concentrations or when the concentration of ATIII is limiting.

HCII inactivates thrombin by acting as a pseudo-substrate for the enzyme. Thrombin cleaves HCII, resulting in the formation of a covalent enzyme-inhibitor complex. The formation of this complex is very slow in the absence of a catalyst. However, in the presence of dermatan sulfate or heparin, the rate of HCII-mediated inhibition of thrombin increases by about 2,000 fold (See, Tollefson, *Ann. NY Acad. Sci.* 714:21–31 (1994)).

A model for HCII catalysis by dermatan sulfate or heparin involves a two-step process. First, the sulfated polysaccharide binds to a positively charged region on HCII and causes unfolding of the N-terminal, negatively charged segment of the HCII molecule. This electronegative N-terminal segment then interacts with the positively charged region on thrombin known as exosite 1. The interaction of the conformationally altered HCII with thrombin increases the rate of inhibition by approximately 50-fold. If the sulfated polysaccharide chain is sufficiently long, a second step occurs which markedly enhances the rate of HCII-mediated inactivation of thrombin. In this second step, the sulfated polysaccharide binds to the electropositive region on thrombin known as exosite 2. Sulfated polysaccharides that can bind to both the inhibitor and the enzyme effectively approximate HCII and thrombin, thereby increasing the rate of HCII-mediated inactivation of thrombin by about 2,000-fold.

The activity of the HCII-specific catalytic agents of the present invention is based, in part, on inactivating thrombin bound to fibrin without necessitating displacement. More particularly, one of the modes of activity of the HCII-specific catalytic agents of the present invention is based, in part, on the following observations. First, because thrombin binds to fibrin via exosite 2, exosite 1 is available to interact with conformationally altered HCII. As a result, conformationally altered HCII can inactivate thrombin bound to fibrin without necessarily displacing it. Second, it has been discovered that certain sulfated polysaccharides, which are poor catalysts of HCII-mediated inactivation of thrombin in solution because they are of insufficient chain length to bind both HCII and thrombin, are still able to effectively catalyze the inactivation of fibrin-bound thrombin by HCII. Thus, the HCII-specific catalytic agents of the present invention are useful, in part, as selective inhibitors of clot-bound thrombin in vivo because they inactivate thrombin bound to fibrin without inducing a marked systemic anticoagulant state.

Without intending to be restricted to a particular theory, it is thought that this selective inhibition occurs because the requirements for catalysis, i.e., activation, of HCII-mediated inactivation of free thrombin are different from those needed for activation of HCII-mediated inactivation of fibrin-bound thrombin. Thus, in accordance with the present invention, polyanions have been identified that are more effective at inactivating fibrin-bound thrombin than free thrombin. These polyanions are unable to catalyze fully HCII-mediated inactivation of free thrombin either because they are of insufficient chain length, or because they lack the necessary negative charge to bind to both HCII and thrombin. Such agents, however, are able to inactivate fibrin-bound thrombin because, in theory, bridging (i.e., binding to both HCII and thrombin) is not a prerequisite for efficient HCII-mediated inactivation of thrombin when the enzyme is immobilized on the fibrin surface. Instead, conformational alteration of HCII by, for example, sulfated polyanions is sufficient to promote the inactivation.

The ability of sulfated polysaccharides to bind to both HCII and thrombin is molecular mass dependent. Sulfated polysaccharides which contain less than about 24 monosaccharide units are typically of insufficient length to simultaneously bind to both HCII and thrombin and, hence, do not dramatically increase the rate of HCII-mediated thrombin inhibition. However, because these agents can still bind to HCII and induce a conformational change, they will increase the rate of thrombin inhibition to a modest extent. Moreover, when thrombin is bound to fibrin at exosite 2 and immobilized, the polysaccharide is not required to bind to thrombin and, thus, the clot-bound thrombin can be readily inactivated by HCII provided that the inhibitor has been modified by the low molecular weight polysaccharide. This is thought to be a possible mechanistic explanation for the selectivity of the HCII-specific catalytic agents of the present invention against clot-bound thrombin.

As such, the compositions and methods of the present invention can provide, inter alia, for complete or near-complete inactivation of clot-bound or thrombus-bound thrombin, whereby thrombin-mediated amplification of coagulation is substantially inhibited or prevented. Usually, at least about 60% inhibition of clot- or thrombus-bound thrombin can be achieved, preferably at least about 90% inhibition, and more preferably at least about 95% inhibition (by "inhibition," in this context, it is meant that the thrombin activity is substantially, irreversibly inactivated so that the thrombin molecule cannot promote clot or thrombus formation or accretion; more generally, inhibition refers to a reduction in activity).

Several HCII catalyst assays or, interchangeably, HCII activating assays are well known to those of skill in the art. An example of such an HCII activating assay is the anti-factor IIa assay (see, Ofoso, Blood 64:742–747 (1984)). Other HCII activating assays include those described in U.S. patent application Ser. No. 08/175,211 (filed Dec. 27, 1993). Similarly, several ATIII catalyst assays or, interchangeably, ATIII activating assays are well known to those of skill in the art. An example of such an ATIII activating assay is the anti-factor Xa assay (see, Teien, et al., Thromb. Res. 8:413–416 (1976)). In addition, several anticoagulant assays are known to those of skill in the art, such as thrombin clotting time, factor Xa clotting time, activated partial thromboplastin time and activated clotting time. The foregoing assays are generally described in, e.g., Low-Molecular-Weight Heparin in Prophylaxis and Therapy of Thromboembolic Diseases (H. Bounameaux (ed.); Marcel Dekker, Inc.; New York, N.Y. (1994)), the teachings of which are incorporated herein by reference for all purposes.

In addition to their ability to selectively inactivate clot-bound thrombin, the products or agents of the present invention can also inhibit the assembly of the intrinsic tenase complex, thereby inhibiting the activation of Factor X by Factor IXa. That is to say, the agents of the present invention are also capable of disrupting or inhibiting the assembly of the intrinsic tenase complex and, in turn, the activation of Factor X by Factor IXa. More particularly, the process of blood coagulation occurs on the surface of activated platelets as a result of the assembly of a number of the coagulation factors on the surface. For instance, in the presence of calcium, Factor IXa complexes with platelet-bound Factor VIIIa to form the intrinsic tenase complex which activates Factor X to Factor Xa. In the presence of calcium, Factor Xa forms a complex with Factor Va on the platelet surface (i.e., the prothombinase complex) which, in turn, converts prothrombin to thrombin. It has surprising been discovered that the agents of the present invention are capable of disrupting the assembly of the intrinsic tenase complex, thereby inhibiting the activation of Factor X by Factor IXa. In studying the mechanism by which the agents of the present invention impair the assembly of the intrinsic tenase complex, it was found that the agents have a marked inhibitory effect of Factor Xa generation induced by either Factor IXa or XIa.

In addition, it has also surprisingly been found that the agents of the present invention are also capable of prolonging the activated partial thromboplastin time (APTT) without exhibiting appreciable anti-factor Xa or anti-factor IIa activity.

Moreover, it has been found that this effect on the APTT is to a large extent independent of HCII and ATIII. The ability of the agents of the present invention to interfere with the assembly of the intrinsic tenase complex explains, in part, some of the HCII- and ATIII-independent effects of the agents of the present invention on the APTT. The agents also inhibit Factor IX activation by Factor XIa which also contributes to prolongation of the APTT. The ability of the agents of the present invention to interfere with the intrinsic tenase complex assembly is extremely important in that it confers on such agents the ability to passivate activated platelets in addition to the ability to inactivate thrombin bound to fibrin.

The products and agents of the invention will now be described in more detail, by way of example only, with illustrative reference to the HCII-specific catalytic agents of the present invention. The preferred properties described below in relation to such HCII-specific catalytic agents are applicable also to the agents and products of other aspects of the invention.

The HCII-specific catalytic agents of the present invention will preferably exhibit one or more of the following characteristics:

i) an HCII catalyst specific activity or, interchangeably, an HCII activating specific activity of about 2 to 5 units/mg in a chromogenic anti-factor IIa assay and, more preferably, about 3 to 4 units/mg;

ii) an ATIII catalyst specific activity or, interchangeably, an ATIII activating specific activity of about 0.2 to 1.5 units/mg in a chromogenic anti-factor Xa assay, preferably about 0.5 to about 1.3 units/mg and, more preferably, about 1 unit/mg;

iii) an ability to inhibit or disrupt the assembly of the intrinsic tenase complex, thereby inhibiting the activation of Factor X by Factor IXa;

iv) an ability to inhibit the activation of Factor IX by Factor XIa;

v) a solubility in aqueous media ranging from about 150 to about 1,000 mg/ml, preferably from about 200 to about 750 mg/ml and, more preferably, from about 400 to about 500 mg/ml;

vi) at concentrations which exert an anti-thrombic effect in vivo, an anticoagulant activity in plasma as measured by thrombin clotting time from 20 to 80 seconds (with a control of 20 seconds), preferably 25 to 45 seconds, and more preferably 30 seconds;

vii) an anticoagulant effect which is contributed to by both an HCII- and ATIII-mediated mechanism, and by a mechanism which is independent of both HCII and ATIII.

The HCII-specific catalytic agents of the present invention are preferably glycosaminoglycans. More particularly, the HCII-specific catalytic agents are preferably polyanionic carbohydrates of about 10 to about 24 monosaccharide units and, more preferably, polyanionic carbohydrates of about 14 to about 20 monosaccharide units. Typically, the HCII-specific catalytic agents are heparin preparations having molecular weights ranging from about 3,000 to 8,000 Daltons ($\pm$1,000 Daltons). As such, in one embodiment, heparin is a preferred source of the HCII-specific catalytic agents of the present invention. Heparin, as previously explained, is a highly sulfated dextrorotary mucopolysaccharide comprised of D-glucosamine and D-glucuronic acid or L-iduronic residues. Generally, heparin has a molecular weight ranging from about 6,000 Daltons to 20,000 Daltons, depending on the source of the heparin and the methods used to isolate it. In a preferred embodiment, the HCII-specific catalytic agents of the present invention are heparin preparations which have been prepared from heparin using the following chemical reactions: (1) depolymerization of unfractionated heparin to yield LMWH; (2) oxidation of the resulting LMWH; and (3) reduction of the oxidized LMWH. It will be readily apparent to those of skill in the art that the order of these steps can be modified, e.g., unfractionated heparin can be oxidized, depolymerized and reduced or, alternatively, oxidized, reduced, depolymerized and reduced, provided the final step is a reduction step.

In addition to being heparin preparations, however, the HCII-specific catalytic agents of the present invention can be, for example, negatively charged polysaccharides other than heparin, negatively charged polyanions, electronegative organic molecules with an affinity for HCII, and the like. Such substances will typically bind to HCII with an affinity of at least $10^{-6}$ M, preferably at least about $10^{-8}$ M or stronger, but with weak affinity for ATIII, preferably weaker than about $10^{-6}$ M.

In one embodiment, the HCII-specific catalytic agents of the present invention can have the following formula:

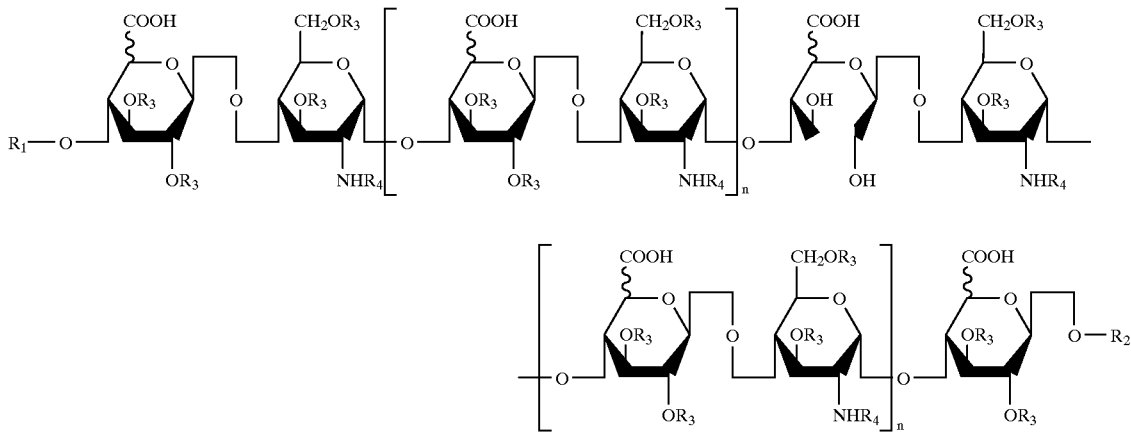

In the above formula, $R_1$ is a member selected from the group consisting of H, D-glucosamine acid residue, D-glucuronic acid residue and L-iduronic acid residue. $R_2$ is a member selected from the group consisting of H, D-glucosamine acid residue, D-glucuronic acid residue, L-iduronic acid residue and anhydromannitol. $R_3$, in the above formula, is a member selected from the group consisting of H and $SO_3^-$. Finally, $R_4$ is a member selected from the group consisting of H, $SO_3^-$ and $CH_3CO^-$. In the above formula, indexes "n" are independently selected and can have values ranging from 0 to about 14. The values of "n" are selected such that the HCII-specific catalytic agents of the present invention will have molecular weights ranging from about 3,000 Daltons to about 8,000 Daltons ($\pm$1,000 Daltons).

In another embodiment, the heparin-derived HCII catalytic agents of the present invention can have the following formula:

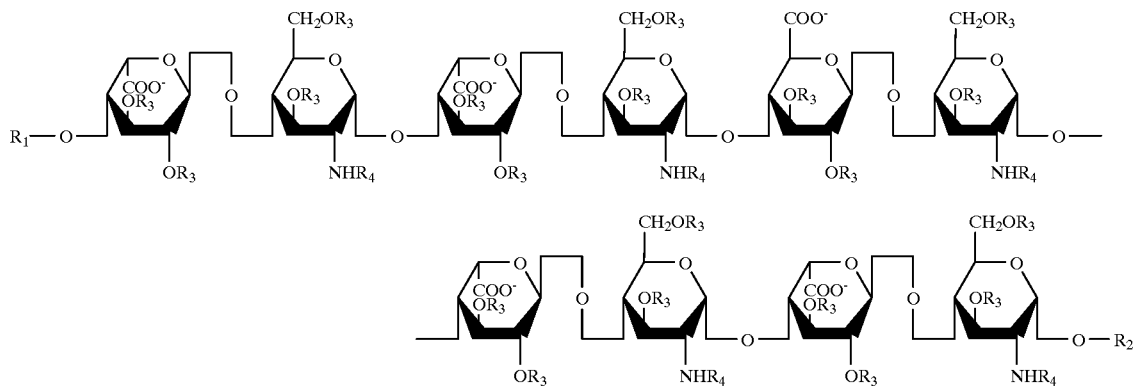

In the above formula, $R_1$ and $R_2$ are members independently selected from the group consisting of H, D-glucosamine acid residue, D-glucuronic acid residue and L-iduronic acid residue. $R_3$, in the above formula, is a member selected from the group consisting of H and $SO_3^-$. Finally, $R_4$ is a member selected from the group consisting of H, $SO_3^-$ and $CH_3CO^-$. In the above structure, sequences having the heparin pentasaccharide sequence for ATIII have been substantially removed by ATIII affinity chromatography. As mentioned, the HCII catalytic agents of the present invention will typically have molecular weights ranging from about 3,000 Daltons to about 8,000 Daltons (±1,000 Daltons).

The HCII-specific catalytic agents (i.e., catalytic agents which selectively catalyze HCII-mediated inactivation of fibrin-bound thrombin, impair the assembly of the intrinsic tenase complex and inhibit the activation of Factor IX by Factor XIa) obtained from heparin preparations can be prepared using a number of different methods. As noted above, in a preferred embodiment, the HCII-specific catalytic agents of the present invention are heparin preparations which have been prepared from heparin using the following chemical reactions: (1) depolymerization of unfractionated heparin to yield LMWH; (2) oxidation of the resulting LMWH to open the ring structures the unsulfated uronic acid moieties; and (3) reduction of the oxidized LMWH to reduce the aldehydes (to alcohols) formed during the depolymerization and oxidation steps. In a further preferred embodiment, the HCII-specific catalytic agents of the present invention are prepared from heparin using the following chemical reactions: (1) depolymerization of unfractionated heparin to yield LMWH using nitrous acid; (2) oxidation of the resulting LMWH using sodium periodate; and (3) reduction of the oxidized LMWH using sodium borohydride. In this preferred embodiment, the resulting low affinity, low molecular weight heparin is a mixture of heparin molecules having a native sugar (e.g., a uronic acid residue) as the nonreducing terminal and a 2,5-anhydromannitol residue as the reducing terminal, and having molecular weights ranging from about 3,000 to about 8,000 Daltons.

More particularly, heparin with low affinity for ATIII is prepared from standard unfractionated heparin (specific activity 150 to 160 anti-factor Xa and anti-factor IIa units/mg) or low molecular weight heparin either chemically by an oxidation reaction followed by a reduction reaction or, alternatively, by ATIII affinity chromatography. In a preferred embodiment, heparin with low affinity for ATIII is prepared chemically. Such chemical modifications involve treating the vicinal alcohol groups present in the heparin preparation with an oxidizing agent followed by a reducing agent in accordance with the protocol set forth in the Example Section. Suitable oxidizing agents include, but are not limited to, sodium periodate and, under certain reaction conditions known to those of skill in the art, lead tetraacetate. Suitable reducing agents include, but are not limited to, sodium borohydride, other metal hydrides and, under certain reaction conditions known to those of skill in the art, lithium aluminum hydride. These reactions cleave the vicinal, i.e., C2–C3, bond of a critical non-sulfated glucuronic acid residue found within the heparin pentasaccharide sequence, i.e., that sequence that has high affinity for ATIII. Cleavage of this bond markedly reduces the affinity of heparin for ATIII. Alternatively, ATIII affinity chromatography can be used to select those heparin chains with little or no affinity for ATIII. When prepared by either technique, the resultant low affinity heparin (LAH) has the following characteristics:

a) It is essentially devoid of ATIII-catalyzing, i.e., ATIII-activating, activity (with <1.5 anti-factor Xa units/mg), but retains anti-factor IIa activity (of about 2 to about 5 units/mg) because of its ability to catalyze, i.e., activate, HCII.

b) Compared to the starting material, the LAH or LA-LMWH (V18) has reduced anticoagulant activity in plasma (as measured by the thrombin clotting time) compared to dermatan sulfate (DS), a high molecular mass HCII catalyst, or hirudin (Table 1). Although LAH or LA-LMWH have reduced activity against free thrombin, they are able to catalyze the inactivation of fibrin-bound thrombin by HCII.

TABLE 1

|  | TCT (seconds) |
| --- | --- |
| Baseline | 19.2 |
| V18 120 µg/mL | 26.5 |
| V18 240 µg/mL | 31.5 |
| V18 480 µg/mL | 37.2 |
| V18 960 µg/mL | 43.6 |
| DS 120 µg/mL | 75.9 |
| DS 240 µg/mL | 445 |
| DS 480 µg/mL | 577 |
| DS 960 µg/mL | 841 |
| LAH 120 µg/mL | 556 |
| LAH 240 µg/mL | 717 |
| LAH 480 µg/mL | 1065 |
| LAH 960 µg/mL | 3403 |
| Hirudin 10 U/mL | >500 |
| Hirudin 20 U/ml | >500 | c) In filter-containing plate assays, the LAH is as effective as standard heparin at promoting HCII-mediated displacement and inactivation of fibrin-bound thrombin.

Both unfractionated heparin and LAH inhibit fibrin-bound thrombin to a greater extent than they displace it, consistent with the concept that HCII is able to inactivate thrombin that is bound to fibrin via exosite 2.

d) Most of the thrombin displaced by either standard heparin or LAH is covalently complexed to HCII as determined by SDS-PAGE analysis.

e) Based on the extent of inhibition of clot-induced fibrinopeptide A (FPA) generation in plasma, LAH is as effective as unfractionated heparin at inactivating fibrin-bound thrombin. In a hanging clot assay, both agents produce only minimal thrombin displacement because the thrombin is bound to fibrin via exosite 2, leaving exosite 1 and the active site free to interact with HCII.

As explained above, a low molecular weight heparin (LMWH) fraction can be prepared using a variety of techniques, including chemical depolymerization using nitrous acid, enzymatic degradation with heparinase and gel filtration. In a preferred embodiment, LWMH is prepared from standard, unfractionated heparin using nitrous acid depolymerization. The resulting LMWH is typically a mixture of heparin molecules having molecular weights ranging from about 3,000 Daltons to about 8,000 Daltons (±1,000 Daltons). This mixture of materials can be used directly or, alternatively, it can be separated into its various components using, for example, gel exclusion chromatography. For instance, the LMWH mixture can be arbitrarily separated into three fractions by gel exclusion chromatography. Fraction 1 has a mean molecular weight of about 8,000 Daltons, Fraction 2 has a mean molecular weight of about 5,000 Daltons and Fraction 3 has a mean molecular weight of about 3,000 Daltons. It has been determined that these three fractions have properties which are distinct from each other as well as from the mixture of materials, i.e., the mixture of heparin molecules having molecular weights ranging from about 3,000 Daltons to about 8,000 Daltons. Thus, depending on whether the mixture of materials, Fraction 1, Fraction 2, Fraction 3 or various combinations of these materials are used, one can take advantage of different properties.

Although LA-LMWH, e.g., V18, is less effective than standard (unfractionated) heparin at displacing thrombin from fibrin-coated filters, it effectively inhibits the bound thrombin. For example, 4 $\mu$M V18, a HCII-specific catalytic agent which is a mixture of LA-LMWH molecules having molecular weights ranging from about 3,000 to about 8,000 Daltons, only displaces 60% of the bound thrombin, but produces greater than 85% inhibition of the activity of the bound enzyme. However, V18 causes less inhibition of fluid-phase thrombin because 4 $\mu$M V18 produces a thrombin clotting time of only 50 sec, whereas 4 $\mu$M unfractionated heparin produces an unmeasurable thrombin clotting time.

The LA-LMWH of the present invention has the following characteristics:

a) Its specific activity is about 0.2 to about 1.5 anti-factor Xa units/mg and about 2 to about 5 anti-factor IIa units/mg.

b) Compared to both standard unfractionated heparin and LAH, LA-LMWH has reduced anticoagulant activity in plasma (as measured by the thrombin clotting time) and produces less catalysis, i.e., activation, of HCII-mediated thrombin inactivation in buffer containing physiological concentrations of HCII (see, Table 1, supra).

c) In filter-containing plate assays, LA-LMWH is less effective than standard heparin or LAH at promoting HCII-mediated displacement of fibrin-bound thrombin, but it is able to promote the inactivation of the bound thrombin to a similar extent.

d) Based on its ability to inhibit clot-induced fibrinopeptide A (FPA) generation in plasma, LA-LMWH is substantially as effective as standard, unfractionated heparin and LAH at inactivating fibrin-bound thrombin. In contrast, the LA-LMWH is less than about one-tenth as effective as heparin and LAH at inactivating free thrombin in a thrombin clotting time assay. Thus, compared to standard, unfractionated heparin and LAH, the LA-LMWH selectively promotes the inactivation of fibrin-bound thrombin.

e) The LA-LMHH of the present invention has an anticoagulant effect which is contributed to by both an HCII- and ATIII-mediated mechanism, and by a mechanism which is independent of both HCII and ATIII.

f) The LA-LMWH of the present invention has an ability to inhibit or disrupt the assembly of the intrinsic tenase complex, thereby inhibiting the activation of Factor X by Factor IXa.

g) The LA-LMHH of the present invention has an ability to inhibit the activation of Factor IX by Factor XIa.

Thus, the products and HCII-specific catalytic agents of the present invention preferably have one or more of the following characteristics. In one embodiment, the present invention preferably provides heparin preparations that have been chemically modified in two ways. First, they are chemically depolymerized using, e.g., nitrous acid and, thus, reduced in size to about one-third of the size of the heparin parent molecule and, thus, they typically have molecular weights ranging from about 3,000 to about 8,000 Daltons (±1,000 Daltons). This modification results in a marked loss of their ability to catalyze the activity of heparin co-factor II (HCII) against free thrombin, while retaining their ability to catalyze the activity of HCII against surface-bound thrombin. Second, they are subjected to oxidation and reduction reactions which result in a loss of about 95 to about 99% of their antithrombin III-binding activity. More particularly, they have weak ATIII catalytic activity or, interchangeably, ATIII activating activity as evidenced by an anti-factor Xa level of approximately 0.2 to about 1.5 units per ml, which represents about a 95 to about 99% reduction in activity compared to the unmodified low molecular weight heparin. Thus, the resulting HCII-specific catalytic agents of the present invention have weak activity against free thrombin, as evidenced by their inability to prolong the thrombin clotting time more than five-fold at concentrations which effectively inactivate surface-bound thrombin. These two properties, namely, a relatively greater ability than other HCII catalysts or, interchangeably, HCII activators (such as dermatan sulfate) to inactivate surface-bound rather than free thrombin and some, albeit markedly reduced, ATIII-dependent anti-factor Xa activity, are responsible for their improved anti-thrombic effects compared to heparin, dermatan sulfate and hirudin in a bypass circuit, which is a measure of surface-bound thrombin, at concentrations which have a lesser effect than these other anticoagulants on the inactivation of free thrombin as measured by the prolongation of the thrombin clotting time.

Moreover, and quite surprisingly, such agents have an anticoagulant effect which is contributed to by both an HCII- and ATIII-mediated mechanism, and by a mechanism which is independent of both HCII and ATIII. As explained above, the ability of the agents of the present invention to interfere with the assembly of the intrinsic tenase complex explains, in part, some of the HCII- and ATIII-independent effects of the agents of the present invention on the APTT. The ability of the agents of the present invention to interfere with the intrinsic tenase complex assembly is extremely important in that it confers on such agents the ability to passivate activated platelets in addition to the ability to inactivate thrombin bound to fibrin.

As a result of the foregoing properties, the products and HCII-specific catalytic agents of the present invention (i.e., catalysts which are capable of displacing and/or inactivating clot-bound thrombin, of disrupting or impairing the assembly of the intrinsic tenase complex and of inactivating Factor IXa generation by Factor XIa) can be used for preventing thrombus formation and/or for blocking thrombus growth in a patient without producing excessive bleeding, i.e., without producing a clinically unsafe increase in systemic bleeding. More particularly, the HCII-specific catalytic agents of the present invention can be administered in doses which inactivate surface-bound thrombin, inhibit the assembly of the intrinsic tenase complex and inhibit activation of Factor X by Factor IXa and/or activation of Factor IX by Factor XIa, but which have only small effects at inhibiting free thrombin. As such, in another embodiment, the present invention provides a method for inhibiting thrombus formation in a patient, preferably without inducing a clinically unsafe increase in systemic bleeding, the method comprising the step of administering to the patient a pharmacologically acceptable dose of a heparin cofactor II-specific catalytic agent of the present invention, the HCII-specific catalytic agent characterized, in part, by: (i) a heparin cofactor II specific activity against heparin cofactor II of about 2 to about 5 units/mg in an anti-factor IIa assay; (ii) an anti-thrombin III (ATIII) specific activity against factor Xa of about 0.2 to about 1.5 units/mg in an anti-factor Xa assay; and (iii) a solubility in aqueous media ranging from about 150 to about 1,000 mg/ml.

The HCII-specific catalytic agents of the present invention are effective when used alone or, alternatively, when used with low doses of heparin or low molecular weight heparin which are required to inactivate free thrombin. In heparin-resistant conditions (i.e., disorders requiring very high doses of heparin), for example, the HCII-specific catalytic agents of the present invention can be used as a heparin-sparing agent. As such, in another embodiment, the present invention provides combinations and, preferably, blends of an HCII-specific catalytic agent and an ATIII catalytic agent, i.e., an ATIII activating agent. Such blends are useful for inhibiting thrombogenesis in a patient without substantially inhibiting normal coagulation. Thus, the compositions or blends of the present invention are useful for inhibiting thrombus formation in a patient without inducing a clinically unsafe increase in systemic bleeding. In addition, such compositions or blends are useful for prophylaxis, for the treatment of venous or arterial thrombosis and for the prevention of clotting in extracorporeal circuits.

The blends of the present invention will typically be from about 90 to about 99.9 percent by weight of an HCII-specific catalytic agent and, more preferably, from about 95 to about 98.5 percent by weight; and from about 0.1 to about 10 percent by weight of an ATIII catalytic agent, i.e., an ATIII activating, and, more preferably, from about 0.5 to about 5 percent by weight. Typically, the overall HCII catalyst activity of the blends will be about 2 to about 5 units/mg and, more preferably, about 2 to about 4 units/mg. ATIII catalytic or activating agents suitable for use in the blends of the present invention include, but are not limited to, heparin and LMWH. In addition, other agents can be added as desired to modify the blend, including, for example, LMWH (0.1 to 5 wt %), heparin (0.1 to 5 wt %), direct thrombin inhibitors, direct inhibitors of activated factor X, etc.

In another embodiment, the present invention provides a method for inhibiting clot-bound thrombin and fluid-phase thrombin in a patient, preferably without inducing a clinically unsafe increase in systemic bleeding, the method comprising the step of administering to the patient a pharmacologically acceptable dose of (i) an HCII-specific catalytic agent capable of inactivating clot-bound thrombin, the HCII-specific catalytic agent having minimal affinity for antithrombin III (ATIII) and a heparin cofactor II specific activity of about 2 to about 5 units/mg in an anti-factor IIa assay; and (ii) an ATIII catalytic agent capable of inactivating fluid-phase thrombin. Suitable ATIII catalytic agents, i.e., ATIII activating agents, include, but are not limited to, heparin, low molecular weight heparin, direct thrombin inhibitors and direct inhibitors of activated factor X. Moreover, in this method, the HCII-specific catalytic agent and the ATIII catalytic agent, i.e., the ATIII activating agent, can be administered to the patient simultaneously, separately or sequentially. When administered to the patient simultaneously, the HCII-specific catalytic agent and the ATIII catalytic agent can be administered together as a single solution or compound or, alternatively, they can be administered separately as two different solutions or compounds.

The HCII-specific catalytic agents and blends of the present invention can be incorporated as components in pharmaceutical compositions which are useful for treating the cardiovascular conditions described above. Such compositions will also be useful in conjunction with conventional thrombolytic treatments, such as the administration of tissue plasminogen activator (tPA), streptokinase, and the like, as well as with intravascular intervention, such as angioplasty, atherectomy, and the like.

Suitable pharmaceutical compositions will contain a therapeutically effective dose of one or more active products of the invention, e.g., a HCII-specific catalytic agent of the present invention, in a pharmaceutically acceptable carrier. Other suitable pharmaceutical compositions will contain a therapeutically effective dose of a blend of an active product of the present invention (e.g., a HCII-specific catalytic agent) and an ATIII-specific catalytic agent. By a "therapeutically effective dose" or, interchangeably, "pharmacologically acceptable dose" or, interchangeably, "anticoagulantly effective amount," it is meant that a sufficient amount of the product or HCII-specific catalytic agent or, alternatively, a combination or blend of, for example, a HCII-specific catalytic agent and an ATIII-specific catalytic agent will be present in order to achieve a desired result, e.g., inhibition of thrombus accretion when treating a thrombus-related cardiovascular condition such as those described above by, for example, inactivating clot-bound thrombin, inhibiting or disrupting the assembly of the intrinsic tenase complex, inhibiting Factor IXa generation by Factor Xa, inhibiting Factor IXa generation by Factor XIa, inhibiting both clot-bound and fluid-phase thrombin, or combinations thereof.

Typically, the active product or HCII-specific catalytic agent will be present in the pharmaceutical composition at a concentration ranging from about 200 mg per dose to 2 g per dose and, more preferably, at a concentration ranging from about 500 mg per dose to 1 g per dose. Daily dosages can vary widely, depending on the activity of the particular HCII-specific catalytic agent employed, but will usually be present at a concentration ranging from about 30 $\mu$g per kg of body weight per day to about 500 µg per kg of body weight per day and, more preferably, at a concentration ranging from about 50 µg per kg of body weight per day to about 200 µg per kg of body weight per day.

With respect to the combined or blended pharmaceutical compositions, the active product or HCII-specific catalytic agent will be present at a concentration ranging from about 3 mg/kg per dose to about 30 mg/kg per dose and, more preferably, at a concentration ranging from about 3 mg/kg per dose to 10 mg/kg per dose, and the ATIII catalytic agent, i.e., the ATIII activating agent, will be present at a concentration ranging from about 10 U/kg per dose to 500 U/kg per dose and, more preferably, at a concentration ranging from about 15 U/kg per dose to 100 U/kg per dose. Daily dosages can vary widely, depending on the activity of the particular HCII-specific and ATIII catalytic or, alternatively, activating agents employed. Typically, the HCII-specific catalytic agent will usually be present at a concentration ranging from about 3 mg per kg of body weight per day to about 30 mg per kg of body weight per day and, more preferably, at a concentration ranging from about 3 mg per kg of body weight per day to about 10 mg per kg of body weight per day, whereas the ATIII catalytic agent will usually be present at a concentration ranging from about 10 U per kg of body weight per day to about 500 U per kg of body weight per day and, more preferably, at a concentration ranging from about 15 U per kg of body weight per day to about 100 U per kg of body weight per day.

The pharmaceutically acceptable carrier can be any compatible, non-toxic substance suitable to deliver the HCII catalytic agent or the blend of a HCII-specific catalytic agent and an ATIII-specific catalytic agent to the patient. Sterile water, alcohol, fats, waxes, and inert solids can be used as the carrier. Pharmaceutically acceptable adjuvants, buffering agents, dispersing agents, and the like can also be incorporated into the pharmaceutical compositions. Such compositions will be suitable for oral, nasal, respiratory or parenteral administration, preferably being suitable for parenteral administration, i.e., subcutaneous, vascular and intravenous administration. It may also be preferred to deliver the substances provided by the present invention via transdermal administration.

In view of the foregoing, it is readily apparent to those of skill in the art that the HCII-specific catalytic agents or active products of the present invention can effectively be used, either alone or in combination with other ATIII catalytic agents, to inactivate clot-bound thrombin, to inhibit or disrupt the assembly of the intrinsic tenase complex, to inhibit Factor Xa generation by Factor IXa, to inhibit Factor IXa generation by Factor XIa, to inhibit both clot-bound and fluid-phase thrombin, or combinations thereof, without inducing a clinically unsafe increase in systemic bleeding. For instance, the HCII-specific catalytic agents of the present invention can effectively be used in combination with other ATIII catalytic, i.e., activating, agents (e.g., heparin or LMWH) to, inter alia, inhibit both clot-bound thrombin and fluid-phase thrombin without inducing a clinically unsafe increase in systemic bleeding. As such, the HCII-specific catalytic agents of the present invention can be used alone, or in combination with other ATIII catalytic, i.e., activating, agents to treat a number of important cardiovascular complications, including unstable angina, acute myocardial infarction (heart attack), cerebral vascular accidents (stroke), pulmonary embolism, deep vein thrombosis, arterial thrombosis, etc.

In addition to being useful in pharmaceutical compositions for the treatment of the cardiovascular conditions described above, one of skill in the art will readily appreciate that the active products or HCII-specific catalytic agents and combinations of the present invention can be used as reagents for elucidating the mechanism of blood coagulation in vitro.

Having produced heparin fractions or derivatives thereof having the desired properties described above, other thrombin inactivators or HCII-specific catalytic agents having similar catalytic specificity and/or affinity can be produced by a variety of methods well-known to those of skill in the art. For example, Fodor, et al., U.S. Pat. No. 5,143,854 describe a technique termed "VLSIPS," in which a diverse collection of short peptides are formed at selected positions on a solid substrate. Such peptides are then screened for the ability to conformationally alter HCII, such screening optionally in competition with the heparin fractions. Libraries of short peptides can also be produced and screened using phage-display technology (see, e.g., Devlin, WO 91/18980). Optionally, these polypeptides or variants produced by other methods, can be variegated to achieve improved binding affinity for HCII (see, e.g., Ladner, U.S. Pat. No. 5,223,409, which is incorporated by reference in its entirety for all purposes).

Peptidic analogs of the HCII activators can be prepared by conventional solid phase synthesis or recombinant techniques, both of which are well described in the art. Suitable solid phase synthesis techniques are based on the sequential addition of amino acids to a growing chain on a solid-phase substrate, as first described in Merriefield, *J. Am. Chem. Soc.* 85:2149–2156 (1963). Commercial systems for automated solid-phase synthesis are now widely available from suppliers, such as Applied Biosystems, Inc., Foster City, Calif. Moreover, recombinant polypeptide production techniques are widely described in the technical and scientific literature. See, for example, *Molecular Cloning: A Laboratory Manual,* Sambrook, et al., Eds., Cold Spring Harbor Laboratory Press, Cold Spring Harbor, N.Y. (1989), Vols. 1–3.

Small molecule mimetics of the HCII-specific catalytic agents of the present invention can be achieved through the use of techniques known to those working in the area of drug design. Such methods include, but are not limited to, self-consistent field (SEF) analysis, configuration interaction (CI) analysis, and normal mode dynamics computer programs, all of which are now readily available. See, Rein, et al., *Computer-Assisted Modeling of Receptor-Ligand Interactions,* Alan Liss, New York (1989) and Navia and Marcko, "Use of Structural Information in Drug Design," in *Current Opinion in Structural Biology,* Vol. 2, No. 2, pages 202–210, 1992. The preparation of compounds identified by these techniques will depend on their structure and other characteristics and may normally be achieved by standard chemical synthesis methods as described in available texts, such as Furniss, et al., *Vogel's Textbook of Practical Organic Chemistry,* John Wiley & Sons, New York 1992 and Larock, *Comprehensive Organic Transformations,* VCH Publishers, Inc., New York 1989.

The invention will be described in greater detail by way of specific examples. The following examples are offered for illustrative purposes, and are intended neither to limit or define the invention in any manner. In the Examples, the thrombin inactivators are illustrated by heparin-derived HCII-specific catalytic agents, but the invention is not limited to such agents.

EXAMPLES

I. Preparation of V18

The following examples illustrate experimental protocols which can be used to prepare the HCII-specific catalytic agents of the present invention. As noted above, in a presently preferred embodiment, the chemical reactions leading to the preparation of the HCII-specific catalytic agents of the present invention are: (1) nitrous acid depolymerization of heparin to yield low molecular weight heparin; (2) periodate oxidation of low molecular weight heparin to open the ring structures of nonsulfated uronic acid moieties; and (3) borohydride reduction of aldehydes (to alcohols) formed during the nitrous acid and periodate steps.

1. Example 1: Preparation of V-18, Lot #7-1 a. Step 1: Isolation of LMW-heparin, Lot #7

Porcine intestinal heparin (250 grams) was dissolved in 5 liters of purified water (5% solution). Sodium nitrite (3.45 grams) was added and dissolved into the solution to give a 10 mM concentration. The solution temperature was between 18 and 24 degrees Celsius. Over the course of about 2 minutes, 30 mls of 37% HCl were added and the pH adjusted from an initial value of 6.32 to a final pH of 3.00. The resultant solution was then stirred for 2 hours at ambient temperature to allow depolymerization to occur. At the end of the 2 hour incubation, the pH was adjusted upwards to a value of 6.75 by slow addition of about 18 mls of 50% NaOH solution.

The sample was then diluted to a volume of 12.5 liters and ultrafiltered against 10 volumes of purified water using a Millipore Pellicon ultrafiltration device equipped with 10,000 molecular weight cut-off membranes (1.5 m$^2$). The permeate from the ultrafiltration was then concentrated and dialyzed using a Millipore Pellicon ultrafiltration unit equipped with 3,000 molecular weight cut-off membranes (1.5 m$^2$). Once the 125 liters of permeate was concentrated to about 6 liters, it was then dialyzed against 3-volumes of purified water. The retentate was then freeze-dried to give LMW-heparin, Lot #7. Yield=106 grams (42%)

Molecular weight characteristics of LMW-heparin intermediate #7 (above) were determined by high performance size exclusion chromatography in conjunction with multiangle laser light scattering (HPSEC-MALLS) and are compiled in Table 1.

periodate was added to the buffered LMW-heparin solution. The resultant solution was incubated in the dark at 4–10 degrees C. for 48 hours with gentle stirring.

After 48 hours, excess sodium periodate was destroyed by addition of glycerol (70 mls). The pH of the resultant reaction mixture was raised to neutrality with ~10 mls of 50% NaOH solution and the resultant solution diluted to about 5.5 liters. This solution was then dialyzed (ultrafiltered) using the Millipore Pellicon system equipped with 3,000 MWCO membranes (as in Step 1 above). After ~7 volumes of permeate were collected, the oxidized LMW-heparin intermediate solution was concentrated to a volume of ~3 liters.

Reduction of the oxidized intermediate was carried out as follow: Sodium bicarbonate (63 grams) was added and mixed into the above 3 liter solution to give ~0.25 M NaHCO$_3$ solution. This solution was kept cold (4–10° C.) while a solution (1.2 liters) containing 22.8 grams of NaBH$_4$ (also 4–10° C.) was slowly added with stirring. Once all the NaBH$_4$ solution was added, the reaction was kept at 4–10° C. for 3.5 hours. The reaction pH was then adjusted to 4.0 with 6 N HCl (~230 mls), mixed for ~30 minutes, then adjusted upwards in pH to 6.2 with 50% NaOH addition. This sample was then ultrafiltered again against the 3,000 MWCO membranes using the Millipore Pellicon system (7 volumes) and finally sterile filtered through a 0.2 μm Sterivex (Millipore) filter. The resultant solution was freeze-dried to give V-18, Lot #7-1. Yield=76.6 grams.

Molecular weight characteristics of the product were determined by HPSEC-MALLS and are compiled in Table 1, supra.

2. Example 2: Preparation of V-18, Lots #9-1 and 9-2 a. Step 1: Isolation of LMW-Heparin, Lot #9

Porcine intestinal heparin (250 grams) was dissolved in 5 liters of purified water (5% solution). Sodium nitrite (8.62 grams) was added and dissolved into the solution to give a 25 mM concentration. The solution temperature was between 18 and 24 degrees Celsius. Over the course of about

TABLE 1

HPSEC-MALLS Results for LMW-Heparin Intermediate & V18 Product

| Lot: | #7 | #7-1 | #9 | #9-1 | #9-2 | #20 | #20-1 |
|---|---|---|---|---|---|---|---|
| >2,000 | 100[i] | 100 | 99.8 | 100 | 100 | 99.2 | 100 |
| >3,000 | 100 | 100 | 80.4 | 100 | 100 | 76.4 | 77.1 |
| >4,000 | 57.5 | 61.8 | 50.1 | 63.6 | 63.9 | 52.1 | 51.8 |
| >5,000 | 35.0 | 39.9 | 29.9 | 36.2 | 36.4 | 35.5 | 34.2 |
| >6,000 | 22.2 | 25.0 | 18.2 | 20.6 | 20.6 | 24.4 | 22.9 |
| >7,000 | 14.0 | 16.3 | 10.8 | 12.0 | 11.8 | 16.5 | 15.8 |
| >8,000 | 9.2 | 10.5 | 6.4 | 6.5 | 6.5 | 11.6 | 10.9 |
| >9,000 | 5.8 | 7.1 | 3.6 | 3.6 | 3.6 | 7.7 | 7.6 |
| Mw[ii] | 4,989 | 5,228 | 4,583 | 5,022 | 5,024 | 4,920 | 4,876 |
| Mn[iii] | 4,421 | 4,602 | 4,031 | 4,582 | 4,603 | 4,067 | 4,006 |
| Mw/Mn[iv] | 1.129 | 1.136 | 1.137 | 1.096 | 1.091 | 1.210 | 1.217 |

[i]Weight fraction above a given molecular weight, expressed in percent.
[ii]Weight-average molecular weight.
[iii]Number-average molecular weight.
[iv]Polydispersity.

b. Steps 2 and 3: Oxidation and Reduction of LMW-heparin, Lot #7

LMW-heparin, Lot #7 (100 grams) was dissolved in 1 liter of purified water at 4–10 degrees Celsius. One liter (1 liter) of 200 mM sodium acetate, pH 5.0 was added to the dissolved sample. Two liters (2 liters) of 200 mM sodium 2 minutes, 33 mls of 37% HCl were added and the pH adjusted from an initial value of 6.32 to a final pH of 3.01. The resultant solution was then stirred for 2 hours at ambient temperature to allow depolymerization to occur. At the end of the 2 hour incubation, the pH was adjusted upwards to a value of 6.28 by slow addition of 50% NaOH solution.

The sample was then diluted to a volume of 10 liters and ultrafiltered against 7 volumes of purified water using a Millipore Pellicon ultrafiltration device equipped with 3,000 MWCO membranes (1.5 m$^2$). The sample was then concentrated to ~3.5 liters and freeze-dried to give LMW-heparin Lot #9. Yield=120.4 grams (48%)

Molecular weight characteristics of LMW-heparin intermediate #9 were determined by HPSEC-MALLS and are compiled in Table 1, supra.

b. Steps 2 and 3: Oxidation and Reduction of V-18, Lots 9-1 and 9-2

Two identical but separate fifty gram (50 gm) samples of LMW-heparin, Lot #9, were treated as follows: LMW-heparin (50 gm) was dissolved in 500 ml of purified water (4–10° C.). Sodium acetate buffer (500 mls of 200 mM, pH 5.0) was added to each identical sample. Sodium periodate (1,000 mils of 200 mM solution) was then added to each reaction and the resultant solutions were each incubated in the dark and cold for 72 hours. After the 72 hr. incubation, glycerol (40 mls) was added to each sample to destroy excess periodate. The reaction pH was then raised to ~6.5 for each sample and each ultrafiltered against 7 volumes of purified water using the Pellicon system equipped with 3,000 MWCO membranes.

Reduction of each of the resultant oxidized LMW-intermediates and all other steps in the workup were exactly as indicated for sample 7-1 in Example 1 (above). Yields of V-18, Lots #9-1 and 9-2 were: 37.4 gms and 36.7 gms, respectively.

Molecular weight characteristics of V-18, Lots #9-1 and 9-2 were determined by HPSEC-MALLS and are compiled in Table 1, supra.

3. Example 3: Preparation of V-18, Lot #20-1 a. Step 1: Isolation of LMW-Heparin, Lot #20

Porcine intestinal heparin (500 grams) was dissolved in 10 liters of purified water (5% solution). Sodium nitrate (9.0 grams) was added and dissolved into the solution to give a 12.8 mM concentration. The solution temperature between 18 and 24 degrees Celsius. Over the course of about 2 minutes, 59 mls of 37% HCl were added and the pH adjusted from an initial value of 6.27 to a final pH of 3.00. The resultant solution was then stirred for 2 hours at ambient temperature to allow depolymerization to occur. At the end of the 2 hour incubation, the pH was adjusted upwards to a value of 6.57 by slow addition of about 38 mls of 50% NaOH solution.

The sample was then diluted to a volume of 17 liters and ultrafiltered against 10 volumes of purified water using a Millipore Pellicon II ultrafiltration device equipped with 8,000 molecular weight cut-off membranes (1.5 m$^2$). The permeate from the ultrafiltration was then concentrated and dialyzed using a Millipore Pellicon II ultrafiltration unit equipped with 3,000 molecular weight cut-off membranes (1.5 m$^2$). Once the permeate (170 liters) was concentrated to about 8.5 liters, it was then dialyzed against 7 volumes of purified water. The retentate was then freeze-dried to give LMW-heparin, Lot #20. Yield=171.3 grams (34%).

Molecular weight characteristics of LMW-heparin intermediate #20 (above) were determined by HPSEC-MALLS and are compiled in Table 1, supra.

b. Steps 2 and 3: Oxidation and Reduction of V-18. Lot 20-1

LMW-heparin (170 gms. of Lot #20) was dissolved in 1,700 mls of purified water (4–10° C.). Sodium acetate buffer (1,700 mls of 200 mM, pH 5.0) was added and mixed with the sample. Sodium periodate (3,400 mls of 200 mM solution) was then added to the mixture to initiate reaction and the resultant solution was incubated in the dark and cold for 72 hours. After the 72 hr. incubation, glycerol (115 mls) was added to destroy excess periodate. The reaction pH was then raised to 6.5 and the oxidized LMW-heparin ultrafiltered against 7 volumes of purified water using the Pellicon II system equipped with 3,000 MWCO membranes.

Reduction of the resultant oxidized LMW-intermediate and all other steps in the workup were comparable to conditions used for sample 7-1 in Example 1 (above). Yield of V-18 Lot #20-1 was 131 gms.

Molecular weight characteristics of V-18 Lot #20-1 were determined by HPSEC-MALLS and are included in Table 1, supra.

4. Example 4: Four Large-Scale Preparations of V-18 of Pharmaceutical Quality a. Step 1A. Nitrous Acid Depolymerization of Heparin All of Steps 1A and 1B were carried out in a controlled-access pilot laboratory maintained at ambient temperature (19–26° C.). Porcine intestinal heparin (1 Kg) is dissolved in 20 liters of purified water (20 to 26° C.) in a 10 gallon polypropylene drum, using a propeller-type Lightnin mixer at medium speed to affect dissolution (5% solution of heparin).

Minimum specifications for the heparin used are a USP potency greater than 170 Units/mg with less than 1% dermatan sulfate impurity, as measured by galactosamine content. Purified water was prepared by a process involving reverse osmosis and meets all USP monograph standards for purified water.

Once the heparin was visually in solution (15 to 60 minutes), solid sodium nitrite was added to achieve a final concentration of 22.5 mM (31.1 grams of ACS reagent grade sodium nitrite added). This was dissolved using a Lightnin mixer at medium speed (dissolution takes less than 5 minutes). With continued agitation, a calibrated pH electrode was placed in the solution and the initial pH of the solution measured (typically, pH=6.1 to 6.3). The heparin/sodium nitrite solution was then covered with a hooded canopy, agitation continued, and the pH adjusted to 3.0 (±0.1) with 37% HCl (ACS reagent, 125 to 135 mls required). Reaction/agitation was continued for 2 hours with periodic measurement of the pH and temperature. After 2 hours, with continued agitation, the pH was adjusted to between 6.75 (±0.25) with 50% NaOH (diaphragm grade, 80 to 100 mls required). Processing of the resultant crude LMW-heparin mixture was then carried out as described in Step 1B, below.

b. Step 1B. Purification of LMW-Heparin

The 20 liter sample from Step 1A was then diluted with purified water to an initial volume of approximately 36 liters and ultrafiltered (dialyzed) using a Millipore Pellicon II ultrafiltration device. The ultrafiltration unit was outfitted with 1.5 m$^2$ of Pellicon II ultrafiltration membranes (cellulose), with a 3,000 Dalton nominal molecular weight cutoff. The 36 liter sample was ultrafiltered against 7–8 volumes of purified water (20 to 26° C.), with the permeate discarded and the retentate concentrated to a final volume of about 12 liters. Inlet pressures were maintained at 60 (±2) PSI and back pressure was maintained at 52 (±2) PSI. Typical permeate flow-rates during the ultrafiltration were 500 (±50) mls/min. Temperature, flow-rates, pressures, and flux-rates were measured periodically throughout the ultrafiltration and recorded. Although most of these values were virtually unchanged during ultrafiltration, the temperature did rise and the flow-rate did fall during the final concentration from 36 to about 12 liters. The temperature was never allowed to reach 50° C., and the concentration was discontinued when the flow-rate had dropped to roughly half the nominal value (~250 mls/min).

Once the ultrafiltration of the LMW-heparin intermediate was complete, the 12 liter sample was placed into disposable polypropylene freeze-dryer trays (4 liters/tray). These were loaded into the freeze-dryer (Virtis) and temperature probes inserted. All trays were frozen overnight until all temperature probes had reached −40° C. Vacuum was then applied to the freeze-dryer and the shelf temperature set at 40° C. Vacuum was continued until all temperature probes had reached at least 35° C. for at least four (4) hours (total drying time=48 hours). At this time, filtered air (0.2μ) was then bled into the chamber and the vacuum released. The dried LMW-heparin intermediate was then removed from the trays into a tared polyethylene polyliner bag and the weight of the LMW-heparin intermediate determined. A one (1) gram sample of this material was removed for retrospective molecular weight analysis and the remaining sample carried to Step 2A.

c. Step 2A. Oxidation of LMW-Heparin

All of the following steps were carried out in a cold-room (2–10° C.). The dried LMW-heparin (550–600 grams) was dissolved in WFI-grade water (2–10° C.) to give a 10% w/v solution. A 10 gallon polypropylene tank was used as the reaction vessel and dissolution was affected by means of Lightnin mixer set at medium speed. An equal volume (5.5–6.0 liters) of 100 mM sodium acetate buffer, pH 5.0 was prepared in a separate polypropylene tank with WFI-grade water (2–10° C.), using ACS-grade reagents (sodium acetate and glacial acetic acid). Once prepared, the resultant buffer was admixed with the dissolved LMW-heparin intermediate. The room was then darkened and the polypropylene tank covered with a black polyethylene bag to exclude stray light. In a separate 10 gallon polypropylene tank, a volume of 200 mM sodium periodate (ACS-grade) was prepared by mixing solid $NaIO_4$ with an appropriate volume of WFI-grade water (2–10° C.). The volume of sodium periodate solution prepared was equal to the combined volume of the LMW-heparin/acetate buffer admixture. Once the sodium periodate was dissolved (10–15 minutes, Lightnin mixer at medium speed), this solution was added with continued mixing to the LMW-heparin/acetate buffer solution. If necessary, a few mls of 50% NaOH were then added to this final mixture to adjust the pH of the entire reaction to 5.0 (±0.1). Final reaction concentrations were 2.5% LMW-heparin, 50 mM sodium acetate (pH=5), and 100 mM sodium periodate. The reaction vessel was continuously stirred and kept dark and cold for 72 hours. During this 72 hour period of oxidation, the pH and temperature of the reaction solution were monitored twice each 24 hours.

At the end of 72 hours, excess glycerol was added (400–450 mls) and mixed into the solution. Mixing was continued for 30–60 minutes to allow conversion of the majority of $NaIO_4$ to $NaIO_3$. The pH of the reaction was then raised to 6.75 (±0.25) with 50% NAOH (50–60 mls). The resultant solution was then stored covered in the dark and cold until ultrafiltration (Step 2B) could be carried out.

d. Step 2B. Purification of the Oxy-LMW-Heparin Intermediate

Step 2B was performed in the cold room with most light excluded until the concentration step (below). The crude oxy-LMW-heparin solution from Step 1a (~24 liters) was diluted to 36 liter with cold (2–10° C.) WFI-grade water and ultrafiltered using the Millipore Pellicon II system with 3,000 Dalton cellulose membranes installed. The 36 liter sample was ultrafiltered against 7–8 volumes of WFI-grade water maintained at 2–10° C. Once ultrafiltration was completed, the purified oxy-LMW-heparin solution was concentrated to a volume of about 12–14 liters and then stored overnight at 2–10° C. in a polyethylene drum until the reduction (Step 3A) could be performed. All ultrafiltration conditions (membranes, pressures, flow rates, etc.) were exactly as described for the earlier procedure (Step 1B), except that WFI-grade water was utilized as the wash solution (diluent), rather than purified water.

e. Step 3A. Reduction of the Oxy-LMW-Heparin Intermediate

Steps 3A and 3B were performed in the cold room (2–10° C.). It was no longer necessary to keep the reaction dark however, since periodate and iodate ions were removed in Step 2B. The oxy-LMW-heparin solution (12–14 liters) from Step 2B was stirred at medium speed with a Lightnin mixer and maintained at 2–10° C. during the following reduction by jacketing the polypropylene tank with an ice-water solution. Solid sodium bicarbonate (generally about 275 grams) was dissolved in the oxy-LMW-heparin solution using the Lightnin mixer to give a final bicarbonate concentration of 0.25 M, and a pH=8.25 (±0.25). In a separate polypropylene container, solid sodium borohydride (>98% by assay, generally about 100 grams) was dissolved in an appropriate volume of ice cold (2–10C) 0.1 N NaOH (generally about 5.3 liters) to give a 0.5 M solution of $NaBH_4$. Over the course of about 1 hour, the 0.5 M $NaBH_4$ solution was slowly pumped (peristaltic pump equipped with Tygon tubing) into the buffered oxy-LMW-heparin with continuous agitation of the latter solution. Once all of the $NaBH_4$ solution had been added to the oxy-LMW-heparin, reduction was allowed to proceed for 3–3.5 hours and maintained at a temperature between 2 and 10° C.

Once 3–3.5 hours had elapsed, the reduction reaction solution was covered with a hooded canopy and excess borohydride destroyed by slow addition of 6 N HCl solution until a final reaction pH of 4.0 (±0.2) was reached (generally 950 to 1050 mls of 6 N HCl was required). After stirring the resultant acidified solution for about 30 minutes, the pH of the entire reaction solution was then raised to 6.75 by addition of 50% NaOH (usually requiring 40 to 50 mls). The canopy was then removed from the solution and resultant crude V-18 stored at 2–10° C. until ultrafiltration (Step 3b) was performed.

f. Step 3B. Purification of V-18

Ultrafiltration of the crude V-18 during Step 3B was performed in the cold room (2–10° C.). Final sterile filtration and freeze-drying of the ultrafiltered V-18 was carried out in a controlled access pilot laboratory maintained at ambient temperature (19–26° C.). The crude V-18 heparinoid from Step 3A (~20 liters) was diluted to 36 liters with cold (2–10° C.) WFI-grade water and ultrafiltered using the Millipore Pellicon II system equipped with 3,000 Dalton cellulose membranes. The 36 liter sample was ultrafiltered against 10–12 volumes of WFI-grade water maintained at 2–10° C. All ultrafiltration conditions (membranes, pressures, flow rates, etc.) were as described earlier (Step 1B). Once ultrafiltration was completed, the purified V-18 heparinoid was concentrated to a volume of about 12 liters and placed in 5-gallon polyethylene drum. The pH of the resultant material was then adjusted to a pH of 7.75 (±0.25) with 50% NaOH (0.25 to 0.5 ml required).

The ultrafiltered V-18 was then sterile filtered and depyrogenated by passage of the ~12 liter solution through a series of two cartridge-type membranes. The first membrane was a 0.45μ Gelman nylon-66 capsule filter and the second was a Pall Posidyne 0.2μ nylon capsule filter. A peristaltic pump operated at ~1 liter/minute and fitted with Tygon tubing and the two sequential filters were used to pass the V-18 from the first polypropylene drum to another clean, depyrogenated drum of the same size.

Once the material was filtered, it was loaded (4 liters/tray) into disposable polypropylene freeze-dryer trays and loaded into a Virtis freeze-dryer. Calibrated temperature probes were inserted into one tray per shelf and the trays frozen overnight until all probes registered →40° C. Vacuum was then applied to the freeze-dryer and the shelf temperature set at 40° C. Vacuum was continued until all temperature probes had reached at least 35° C. for at least four (4) hours (total drying time ≧48 hours). At this time, filtered air (0.2μ was then bled into the chamber and the vacuum released. The dried V-18 heparinoid bulk drug substance was then removed from the trays into a tared polyethylene polyliner bag and the weight of the final product determined. A second polyliner bag was then placed around the product and the double-bagged material placed in a 5-gallon fiber drum for storage. Two (2) bags of Desi-pac desiccant were then placed between the outer of the two polyliner bags and the inner wall of the fiber drum to absorb moisture. Storage of the resultant containers and V-18 product was in a locked cabinet maintained at 65–75° F. Final yield of dry V-18 product was between 400 and 460 grams for each of the four lots prepared as described.

Tables 2 contains most of the salient details regarding all four (4) lots of V-18 manufactured under GMP conditions. Lot #1618-0002 was manufactured with a slightly different amount of sodium nitrite than was used in the other lots.

TABLE 2

HPSEC-MALLS Results from Four Lots of V18 Product

| Lot Number | 1618-0001 | 1618-0002 | 1618-0003 | 1618-0004 |
|---|---|---|---|---|
| >3,000 | 100[i] | 100 | 100 | 100 |
| >4,000 | 65.0 | 74.3 | 76.8 | 79.2 |
| >5,000 | 39.9 | 47.1 | 47.4 | 49.3 |
| >6,000 | 25.4 | 30.2 | 28.9 | 30.1 |
| >7,000 | 15.5 | 19.2 | 17.7 | 18.3 |
| >8,000 | 9.4 | 12.5 | 11.3 | 11.5 |
| >9,000 | 5.7 | 7.8 | 6.8 | 6.9 |
| $Mw^{ii}$ | 5,201 | 5,565 | 5,523 | 5,599 |
| $Mn^{iii}$ | 4,683 | 5,008 | 5,035 | 5,111 |
| $Mw/Mn^{iv}$ | 1.111 | 1.111 | 1.097 | 1.095 |

[i]Weight fraction above a given molecular weight, expressed in percent.
[ii]Weight-average molecular weight.
[iii]Number-average molecular weight.
[iv]Polydispersity.

II. Mechanisms of Action of V18

As described herein, V18 is a small molecular weight heparin fragment that has been modified so that it has minimal HCII-mediated and ATIII-mediated activity against fluid phase thrombin and factor Xa. V18 differs from low molecular weight heparin (LMWH) since it (V18) has minimal anti-factor Xa activity. V18 also differs from dermatan sulfate and low molecular weight dermatan sulfate since it (V18) has minimal HCII-mediated activity against fluid phase thrombin (Table 1).

As a result of its minimal HCII-mediated and ATIII-mediated activity against fluid-phase thrombin and factor Xa, V18 can be safely administered in high doses that produce concentrations of the compound of up to 150 μg/ml. These concentrations are at least ten times higher than tolerable concentrations of LMWH. At these concentrations, additional antithrombotic properties of V18 are manifest. Such properties include, for example, the following two properties: 1) disruption of the assembly of the intrinsic tenase complex, thereby impairing the activation of Factor X by Factor IXa; and 2) inhibition of factor IX activation by Factor XIa.

Thus, V18 has, inter alia, three unique mechanisms of action. The first is the selective inactivation of fibrin-bound thrombin through a HCII-mediated mechanism, and the second and third impair factor Xa generation through the intrinsic pathway. Such mechanisms of action are illustrated in FIG. 1. As illustrated in FIG. 1, V18 is able to:

1) catalyze HCII-mediated inactivation of fibrin-bound thrombin, while having minimal effects on inactivation of fluid-phase thrombin by either HCII or ATIII;

2) disrupt the assembly of the intrinsic tenase complex, thereby impairing the activation of Factor X by Factor IXa; and 3) impair factor IX activation by Factor XIa.

The above three properties, among others, of V18 render it unique among antithrombotic agents and provide it with potential advantages over other antithrombotic agents. The explanation for these potential advantages are shown in FIGS. 2–5.

Thrombosis is initiated when the intimal injury exposes blood to collagen (which stimulates platelet aggregation and Factor XI activation) and to tissue factor derived from activated leucocytes or the fatty contents of an atherosclerotic plaque. When present in relatively low concentrations, tissue factor initiates clotting by complexing Factor VII or Factor VIIa. The Factor VIIa-tissue factor complex then activates Factor IX (see, FIG. 2).

Figure 3:
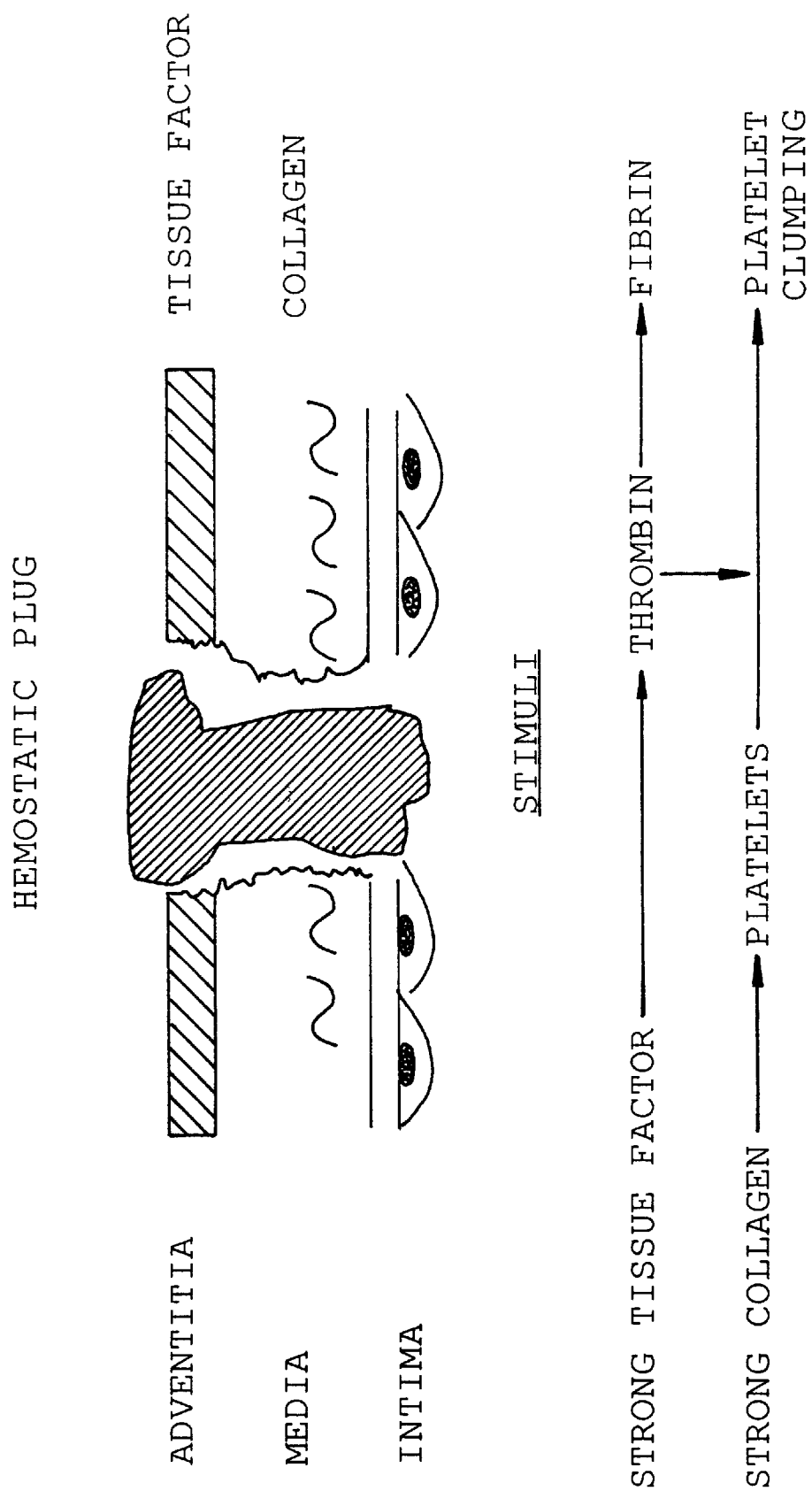

In contrast to thrombosis, which is initiated by superficial injury to the intima, hemostasis is triggered by exposure of blood to the severed wall (intima, media and adventitia) of the blood vessel (see, FIG. 3). Blood flowing from the disrupted vessel is exposed to high concentrations of collagen in the media and high concentrations of tissue factor in the adventitia and the "hole" in the vessel is sealed by a platelet-rich hemostatic plug.

Figure 4:
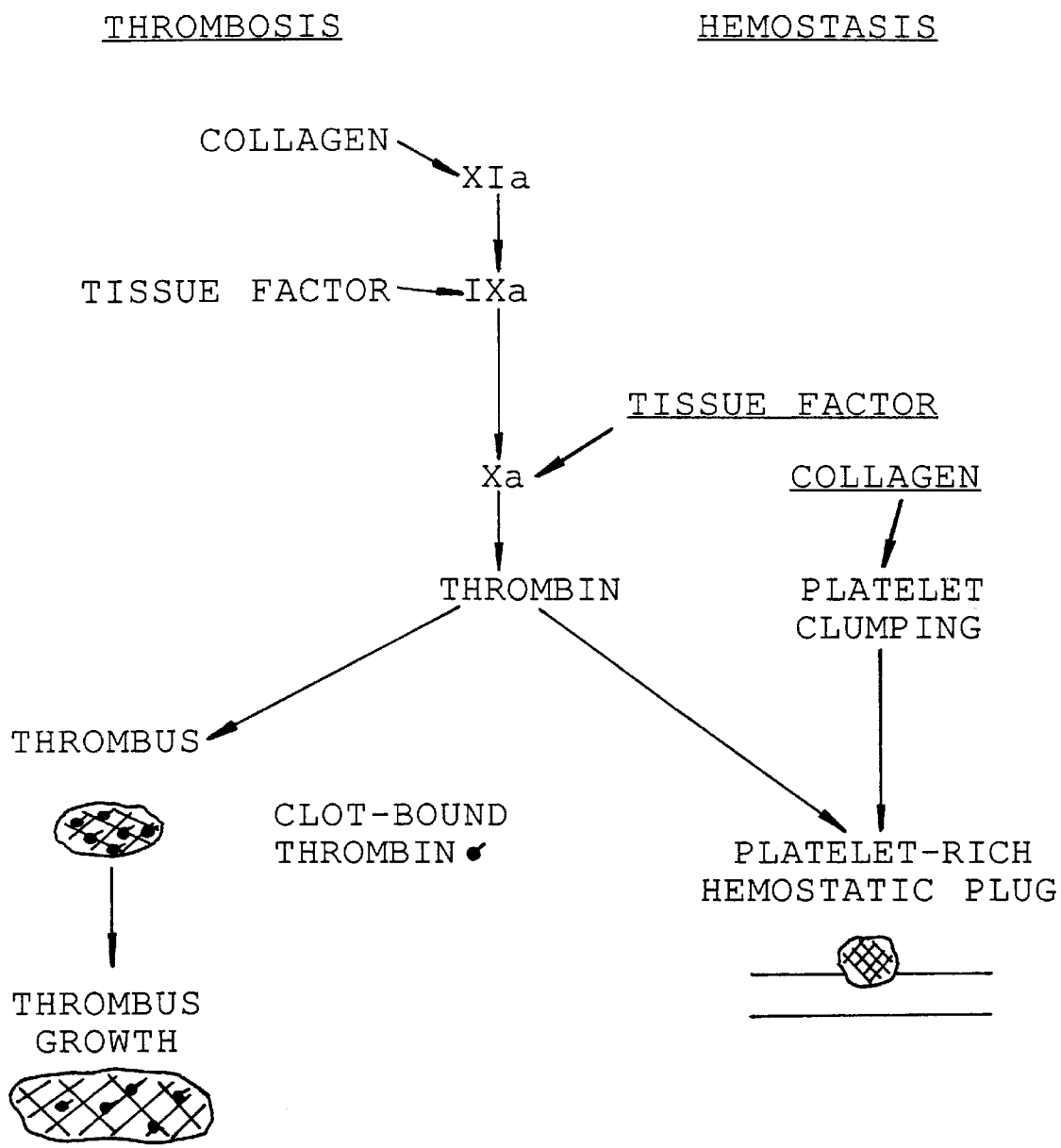
FIG. 4 compares and contrasts the processes of thrombus and hemostatic plug formation.

FIG. 4 compares and contrasts the processes of thrombus and hemostatic plug formation. The stimulus to thrombosis is much less potent than the stimulus for hemostatic plug formation. Thrombosis is initiated by relatively lower concentrations of tissue factor than hemostasis. Similarly, thrombosis is initiated by exposure of blood to lower concentrations of collagen than is hemostasis. The low concentrations of tissue factor/Factor VIIa complex generates thrombin by activating Factor IX and the exposed collagen both activates Factor XI and initiates platelet aggregation (not shown in FIG. 4), thereby triggering thrombosis. Thrombin remains bound to the fibrin, where it stimulates further thrombus growth.

In contrast, hemostatic plug formation is much more explosive. The strong tissue factor stimulus initiates clotting by activating Factor X, thereby bypassing the more proximal steps in coagulation and the exposure of platelets to the resulting thrombin and to collagen in the media results in the much more rapid formation of a platelet-rich hemostatic plug (see, FIG. 4).

Figure 5:
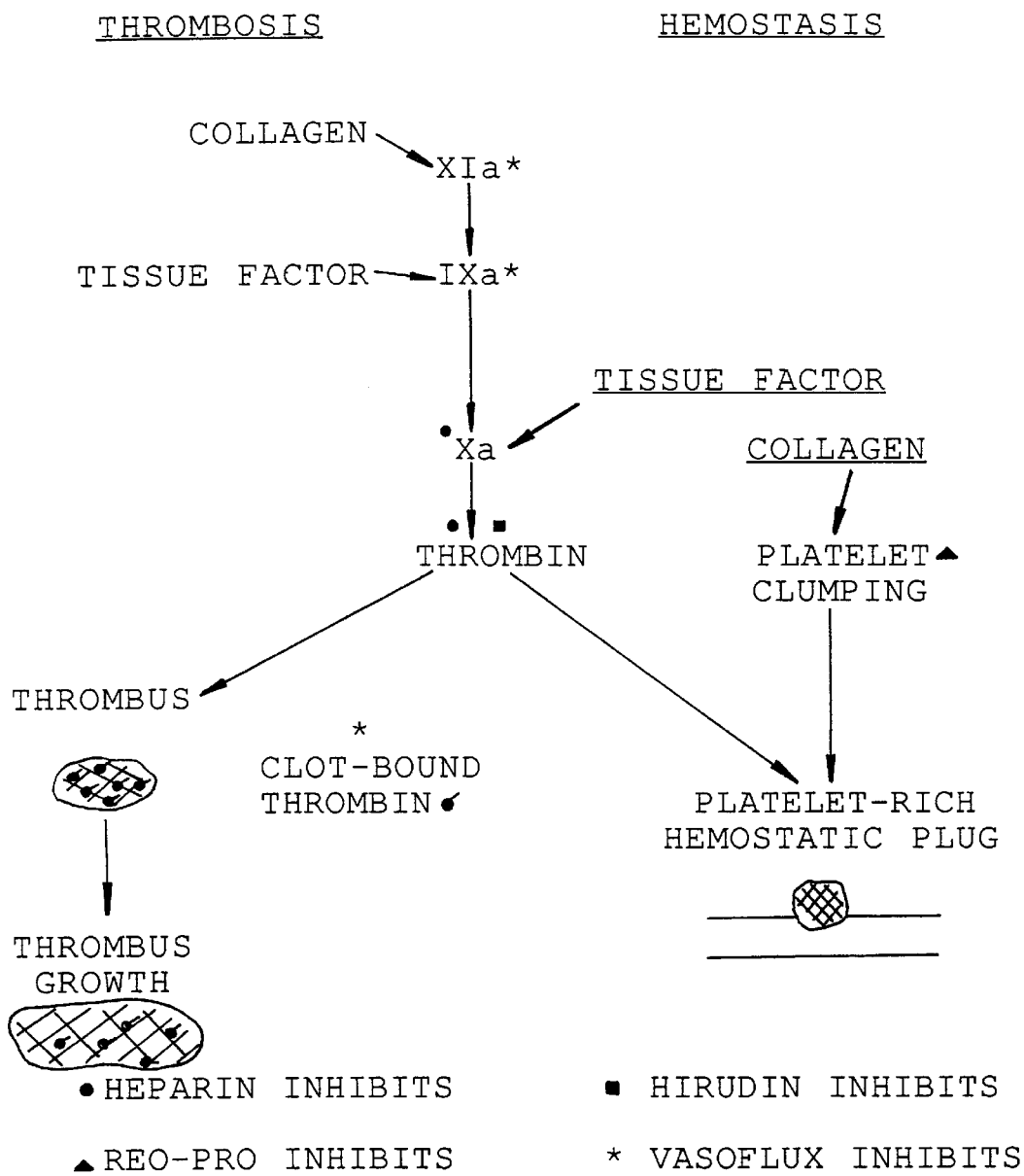
FIG. 5 illustrates the steps in the sequence of thrombosis and hemostasis that are inhibited by the various antithrombotic agents.

FIG. 5 illustrates the steps in the sequence of thrombosis and hemostasis that are inhibited by the various antithrombotic agents. As illustrated therein, V18 delays Factor Xa and thrombin generation by inhibiting Factors IXa and XIa as well as by inactivating fibrin-bound thrombin (thereby bypassing the main steps in hemostasis). In contrast, heparin and LMWH inhibit thrombin and Factor Xa, and hirudin and the other direct thrombin inhibitors inactivate fluid-phase thrombin as well as fibrin-sound thrombin and, thus, all of these compounds at antithrombotic doses have the potential to impair hemostasis.

A. Mechanism 1: Selective Inactivation of Fibrin-Bound Thrombin

Figure 6:
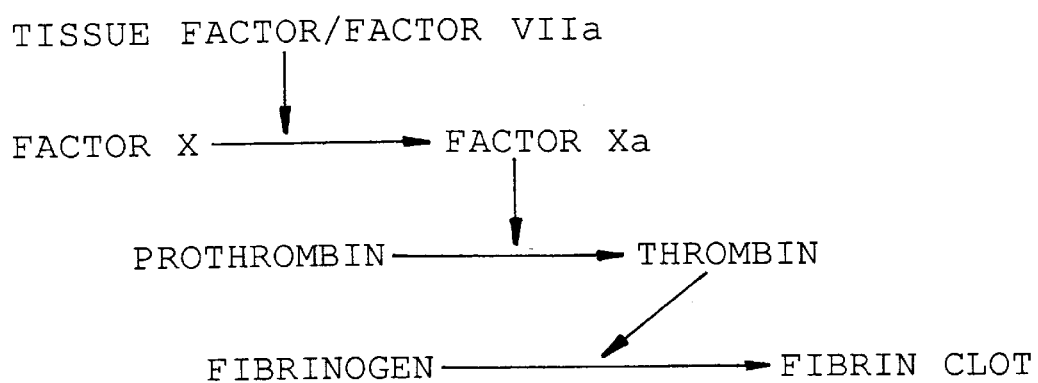
FIGS. 6 and 7 illustrate the principle of the dilute prothrombin time (dilute PT) assay.
Figure 7:
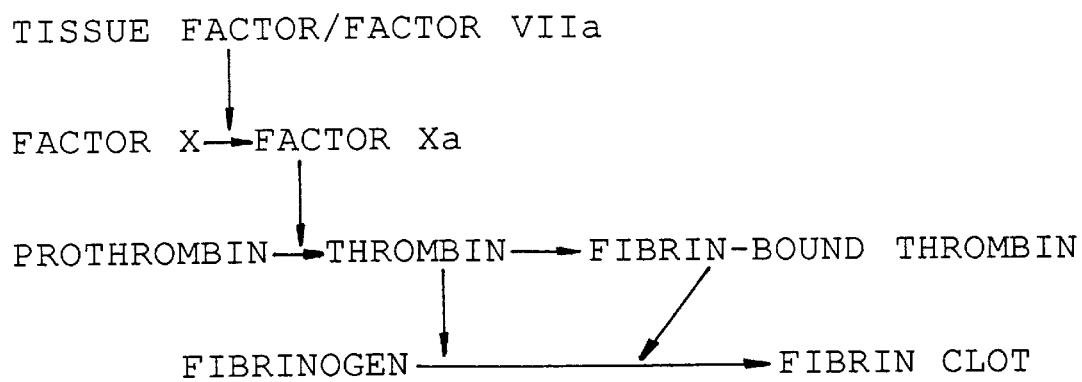
Figure 8:
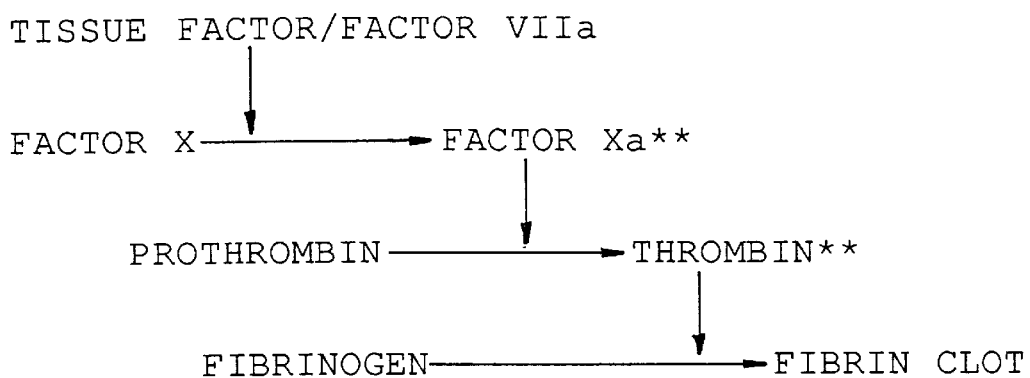
FIG. 8 illustrates that heparin and LMWH prolong the dilute PT in the absence of a plasma clot because they inhibit Factor Xa and thrombin. In contrast, V18 does not prolong the dilute PT because it does not inactivate fluid phase thrombin or Factor Xa.

The validity of this mechanism of action of V18 has been confirmed by an assay that is based on a dilute prothrombin time (dilute PT Assay). The principle of the dilute PT time is illustrated in FIGS. 6 and 7. Briefly, tissue thromboplastin (diluted 1 in 90), which is a mixture of tissue factor, phospholipid and calcium, is added to citrated plasma. The test is influenced by Factor VII, Factor VIIa, Factor Xa, Factor Va and prothrombin. Therefore, the dilute PT is prolonged by anticoagulants that inactivate Factor VIIa, Factor Xa or thrombin (FIG. 8).

Figure 10A:
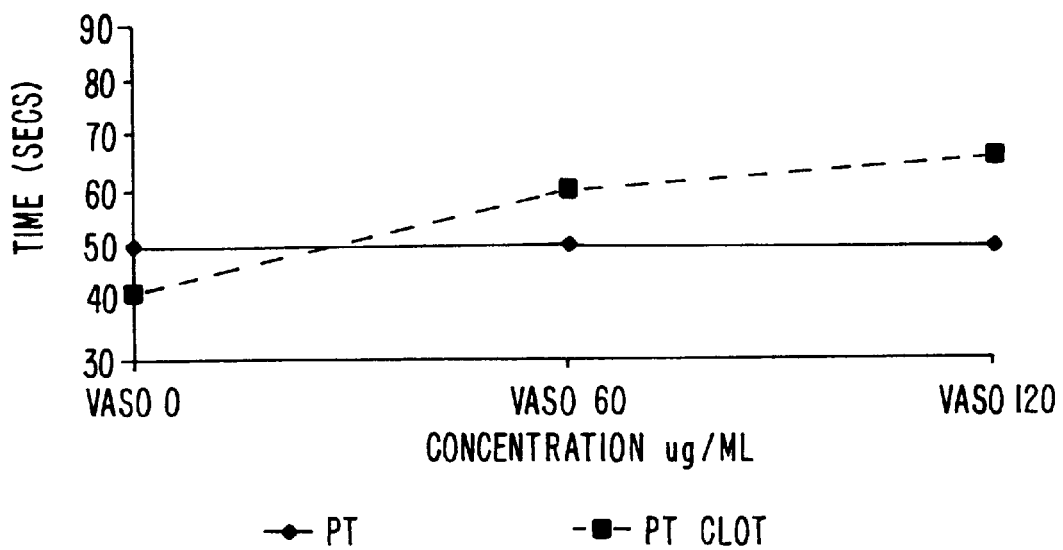
FIGS. 10a and 10b illustrate the effects of V18 and heparin, respectively, on the dilute PT in the presence and absence of a clot.
Figure 16A:
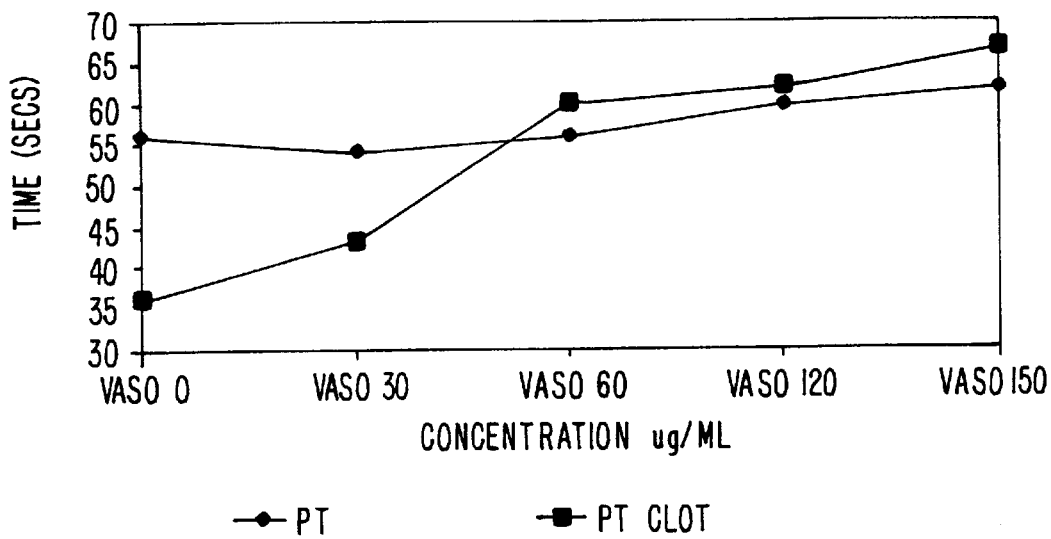
FIGS. 16a and 16b illustrate the effect of V18 on the dilute PT with and without clot in ATIII-depleted plasma, and with and without clot in HCII-depleted plasma, respectively.
Figure 16B:
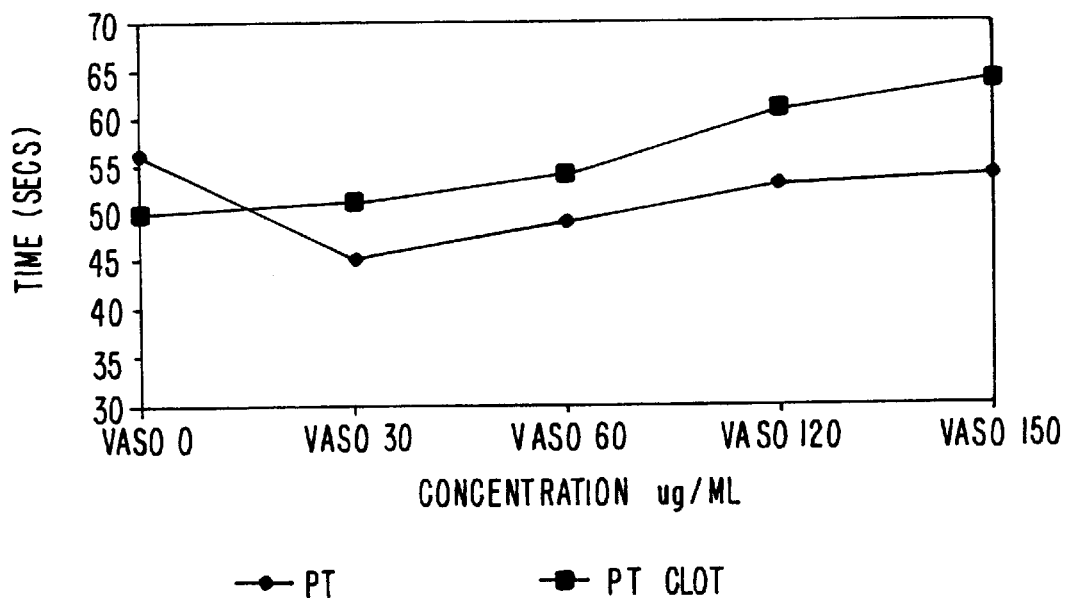

FIG. 10a illustrates the effect of V18 on the dilute PT in the absence and presence of a washed plasma clot, whereas FIG. 16 shows the same experiment done in ATIII-depleted plasma (FIG. 16) or HCII-depleted plasma (FIG. 16b). In normal plasma (FIG. 10a), V18 does not prolong the dilute PT in the absence of a clot indicating that, at the concentrations used in this experiment, V18 has no effect on Factor VIIa, Factor Va, Factor Xa or fluid-phase thrombin. In contrast, in the presence of a clot, V18 prolongs the dilute PT in control plasma (FIG. 10a) and ATIII-depleted plasma (FIG. 16a), but not in HCII-depleted plasma (FIG. 16b). V18 prolongs the dilute PT in the presence of a clot because it inactivates clot-bound thrombin and this effect is HCII, and not ATIII, dependent because it is abolished when HCII is removed from the plasma (FIG. 16b).

Figure 15:
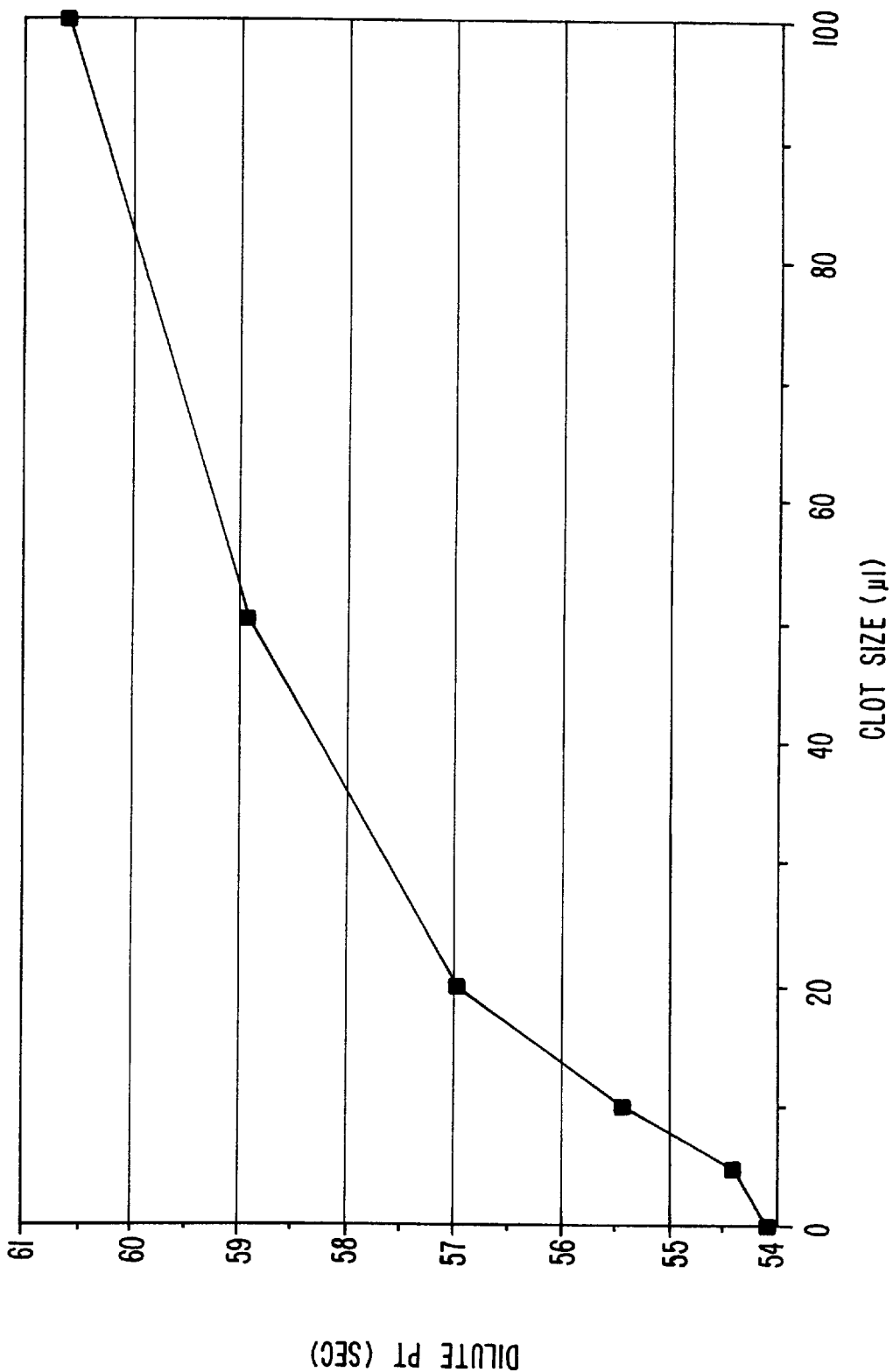
FIG. 15 illustrates the effect of clot size on the dilute PT.

When the dilute PT is performed in the presence of a washed plasma clot, the clot provides (a) a fibrin surface to which free thrombin generated in response to the thromboplastin addition can bind (i.e., the clot acts as a "thrombin sink"), and (b) a source of protected thrombin that shortens the basal clotting time by about 20 sec (FIG. 10a). The ability of the clot to bind thrombin is shown in FIG. 15. When clots of different sizes (prepared by clotting increasing concentrations of fibrinogen with a catalytic amount of thrombin) were added to citrated plasma and the dilute PT was measured, there was progressive prolongation of the PT with the larger clots. Thus, the greater the fibrin surface that is presented, the more thrombin that is adsorbed, and the less that is available to clot the fibrinogen in plasma. As a result, the dilute PT progressively lengthens.

Figure 10B:
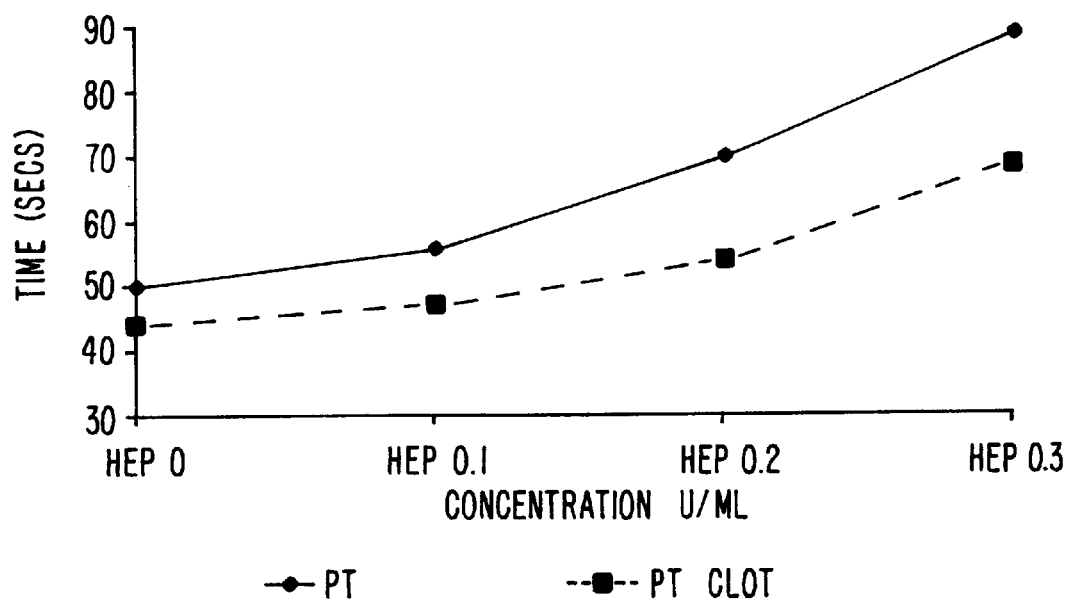

V18 inhibits clot-bound thrombin, thereby blocking the stimulus that shortens the dilute PT. As a result, the fibrin can adsorb thrombin so that in the presence of a washed plasma clot, V18 progressively prolongs the dilute PT (FIG. 10a). In contrast to V18, heparin does not inactivate fibrin-bound thrombin. As a result, it cannot counteract the procoagulant effects of the washed plasma clot so that with heparin, the dilute PT in the presence of a clot is always shorter than that in its absence (FIG. 10b).

As illustrated in FIG. 13, the dilute PT is almost the same in Factor IX-deficient plasma as it is in control plasma. This indicates that the dilute PT is not influenced by Factor IX suggesting that at the concentrations of thromboplastin used in the assay, the Factor VIIa-tissue factor complex is activating Factor X and not activating Factor IX.

In summary, heparin and LMWH prolong the dilute PT in the absence of a plasma clot because they inhibit Factor Xa and thrombin (FIG. 8). In contrast to heparin (and LMWH), V18 does not prolong the dilute PT because it does not inactive fluid phase thrombin and Factor Xa.

Figure 9:
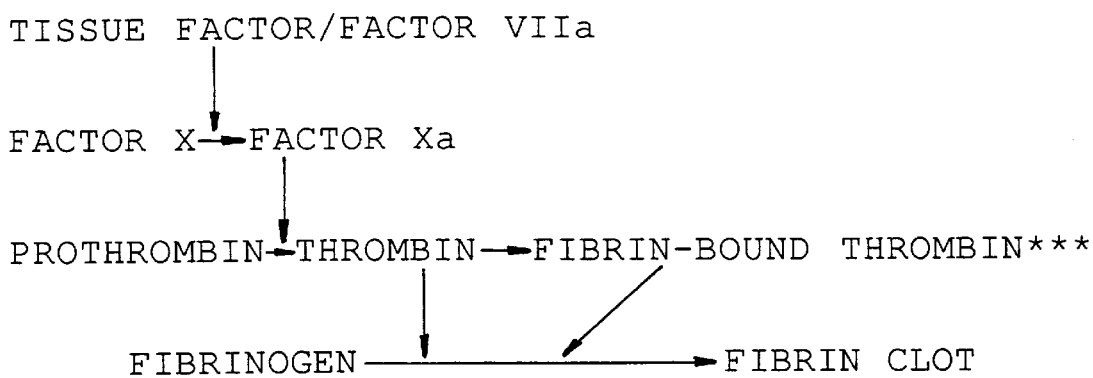
FIG. 9 illustrates that V18 prolongs the dilute PT time in the presence of a clot, reflecting its ability to inactivate fibrin-bound thrombin. In contrast, heparin and LMWH are less effective as anticoagulants in the presence of a clot because they are unable to inactivate fibrin-bound thrombin.

When a washed plasma clot is added to the plasma before starting the assay, the dilute PT time is shortened because of the procoagulant effects of fibrin-bound thrombin. However, in contrast to its lack of effect on the dilute PT without the addition of the clot, V18 increases the dilute PT time in the presence of a clot, reflecting its ability to inactivate fibrin-bound thrombin, thereby allowing the fibrin to adsorb thrombin. In contrast, heparin and LMWH are less effective as anticoagulants in the presence of a clot because they are unable to inactivate fibrin-bound thrombin (FIG. 9).

Figure 12:
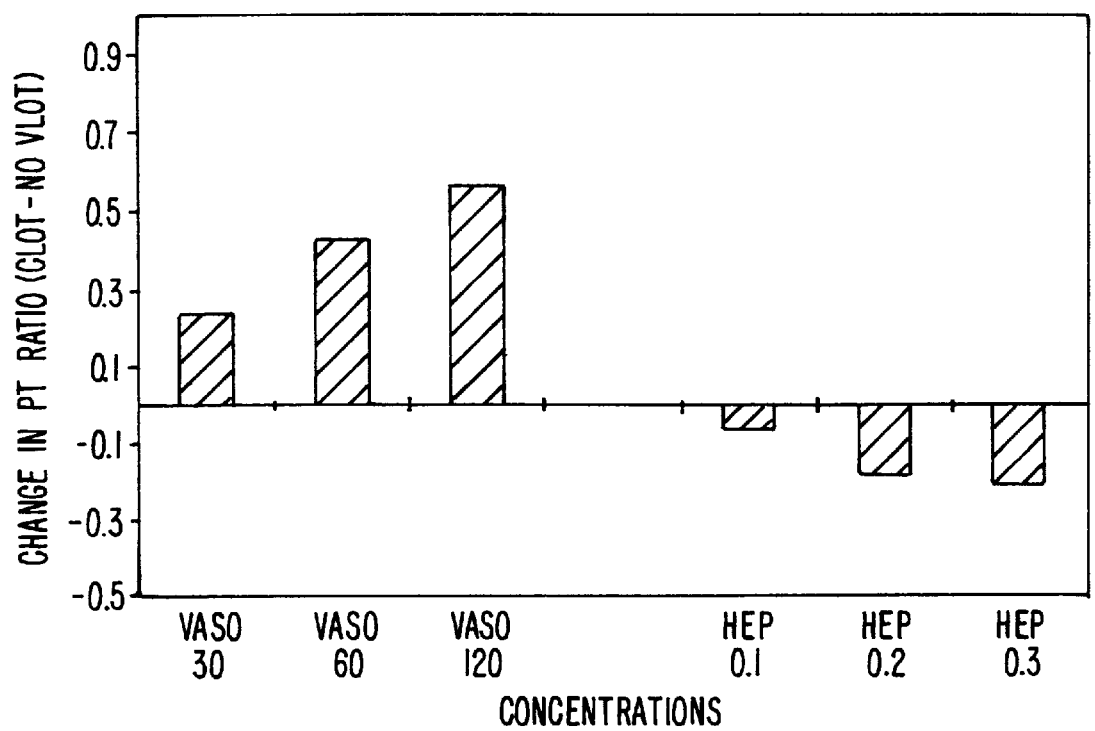
FIG. 12 illustrates the effects of V18 and heparin on dilute PT when a clot is added to normal plasma.

FIG. 10 compares the effects of V18 and heparin on the dilute PT when the test is performed in the absence and in the presence of a washed plasma clot. In the absence of the clot, V18 has no effect on the dilute PT assay. When the assay is performed in the presence of a washed plasma clot, the PT is shortened by the effects of V18 fibrin-bound thrombin. In contrast to its effects in the absence of a plasma clot, V18 produces a dose-dependent prolongation of the dilute PT which overshoots the baseline value of 50 seconds (see, FIG. 10a). In contrast to V18, heparin prolongs the dilute PT in the absence of a clot (through its action on fluid phase thrombin and Factor Xa), but is less effective in the presence of a clot. Thus, in the presence of a clot, the dilute PT ratio is increased by more than 40% by V18 (60 μg/ml) and by almost 60% by V18 (120 μg/ml), compared to the effects in the absence of a clot. In contrast, with heparin, the prolongation of the dilute PT is consistently less in the presence than in the absence of a clot. This difference between the effects of V18 and heparin on the dilute PT can be more readily appreciated by plotting the results as a change in the ratio in the presence and absence of a clot as a function of concentration. Over a range of 0 to 120 μg/ml, V18 produces a dose dependent increase in ratio in the presence of a clot, whereas the increase in ratio produced by heparin in the absence of a clot is blunted by the presence of a clot (see, FIGS. 11 and 12).

The dilute PT is not responsive to V18 because even with the low concentration of tissue factor used, the tissue Factor/VIIa complex activates Factor X and bypasses Factor IX. Thus, as illustrated in FIG. 13, the baseline dilute PT is similar when performed in normal and Factor IX-deficient plasma (FIG. 13). The assay is equally responsive to heparin and LMWH (which inactivate fluid-phase Factor Xa and thrombin) when performed in normal and Factor IX deficient plasma (see, FIG. 14).

The above findings are interpreted as follows: V18 can inactivate clot-bound thrombin through a HCII-mediated mechanism, thereby "passivating" the clot. The phenomenon of overshooting can be explained by the well-described observation that fibrin acts as an antithrombin by binding fluid phase thrombin and reducing its catalytic activity. Thus, as illustrated in FIG. 15, when fibrin clots of increasing size (formed by clotting from fibrinogen with catalytic concentrations of thrombin) are added to plasma, there is a clot-size dependent prolongation of the dilute PT assay. Therefore, agents, such as V18, that inactivate clot-bound thrombin have the potential to capitalize on the antithrombin effects of fibrin. In contrast to V18, heparin is incapable of inactivating clot-bound thrombin and prolongs the dilute PT more effectively in the absence than in the presence of a clot, i.e., by inactivating fluid phase thrombin and Factor Xa.

Figure 17A:
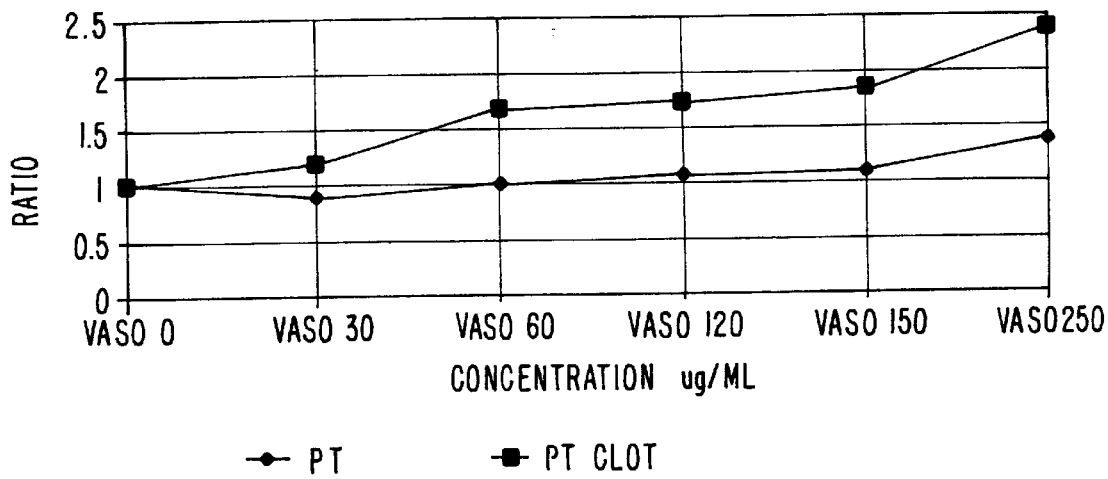
FIGS. 17a and 17b illustrate the effect of V18 on the dilute PT ratio with and without clot in ATIII-plasma, and with and without clot in HCII-depleted plasma, respectively.
Figure 17B:
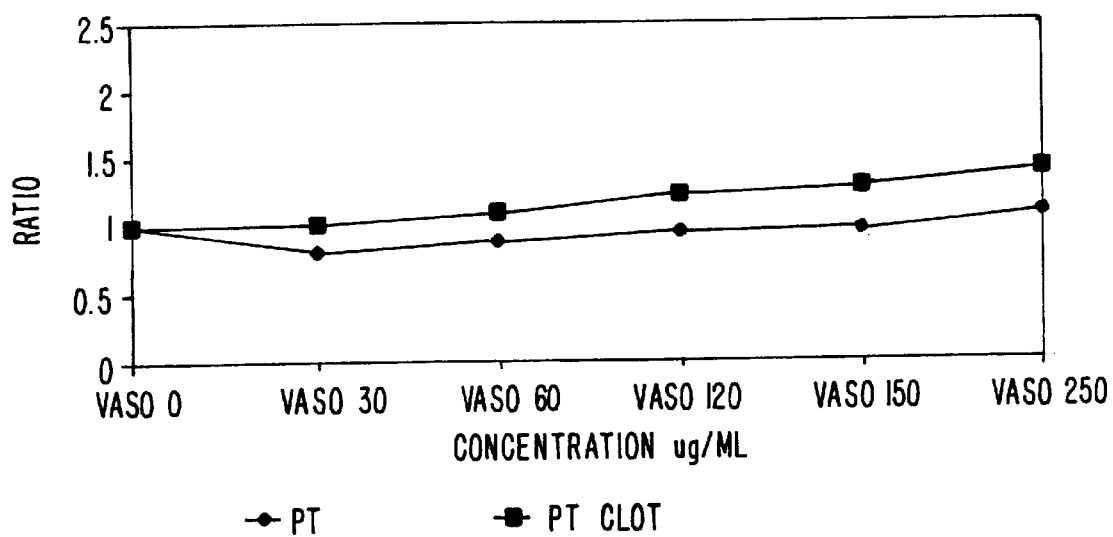

The V18 experiments were repeated in ATIII-depleted and HCII-depleted plasma (see, FIGS. 16 and 17). FIG. 16 illustrates the results of the dilute PT assay expressed in seconds, whereas FIG. 17 illustrates the results of the PT assay expressed as a ratio. In the absence of a clot, V18 did not prolong the dilute PT. However, in the presence of a clot, V18 prolonged the dilute PT in a HCII-dependent manner (ATIII-depleted plasma) and this effect was substantial even at relatively low concentrations (60 μg/ml) of V18. V18 also prolonged the dilute PT weakly in an ATIII-dependent manner (HCII-depleted plasma).

B. Mechanism 2: Inhibition of Assembly of Intrinsic Tenase Complex

In addition to its effects on clot-bound thrombin, V18 also inhibits Factor Xa generation by disrupting assembly of intrinsic tenase by interfering with Factor IXa. This effect of V18 on Factor Xa generation is largely independent of ATIII and HCII.

Figure 18A:
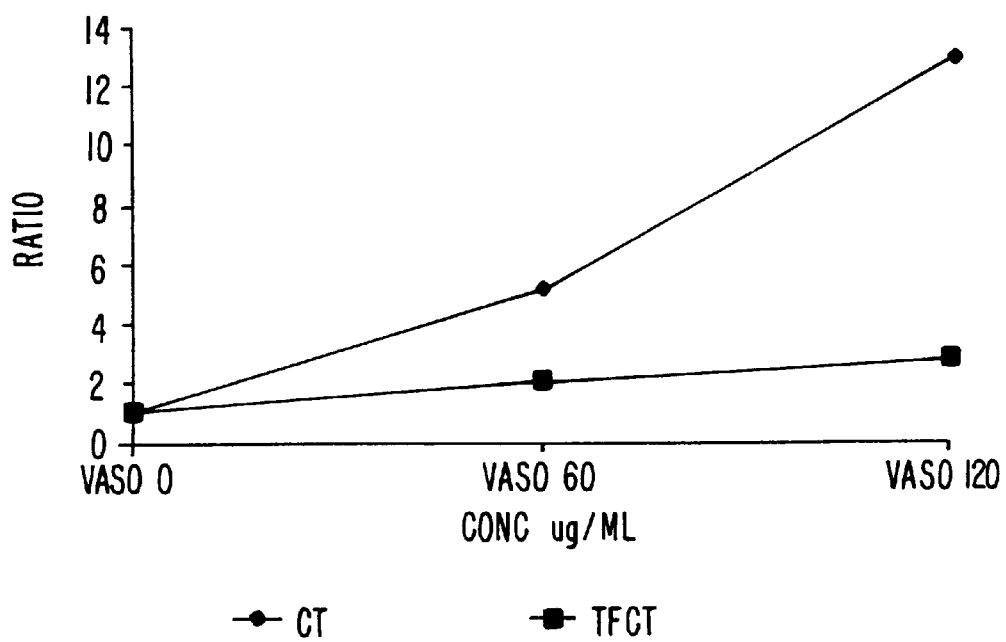
FIGS. 18a and 18b illustrate the effect of V18 and LMWH, respectively, on the whole blood clotting time in the absence and presence of tissue factor.
Figure 18B:
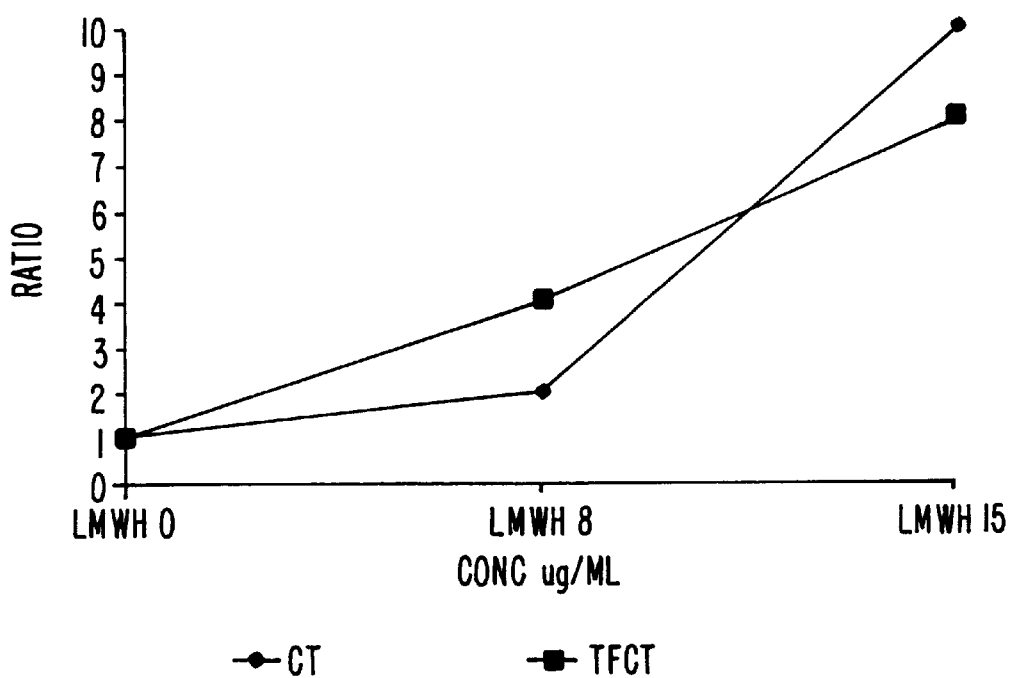

The difference in the mechanism of inhibition of coagulation by V18 and LMWH (and heparin) is also illustrated in FIG. 18. The experiments were performed by comparing the ability of V18 and LMWH to prolong the whole blood clotting time with and without the addition of tissue factor. V18 prolongs the clotting time by impairing Factor IXa and Factor XIa activity with only minimal effects on the tissue factor clotting time, which stimulates clotting by activating Factor X. In contrast, LMWH prolongs the clotting time and the tissue factor clotting time to a similar extent because it inhibits Factor Xa and thrombin which influences both the clotting time and the tissue factor clotting time.

Figure 19A:
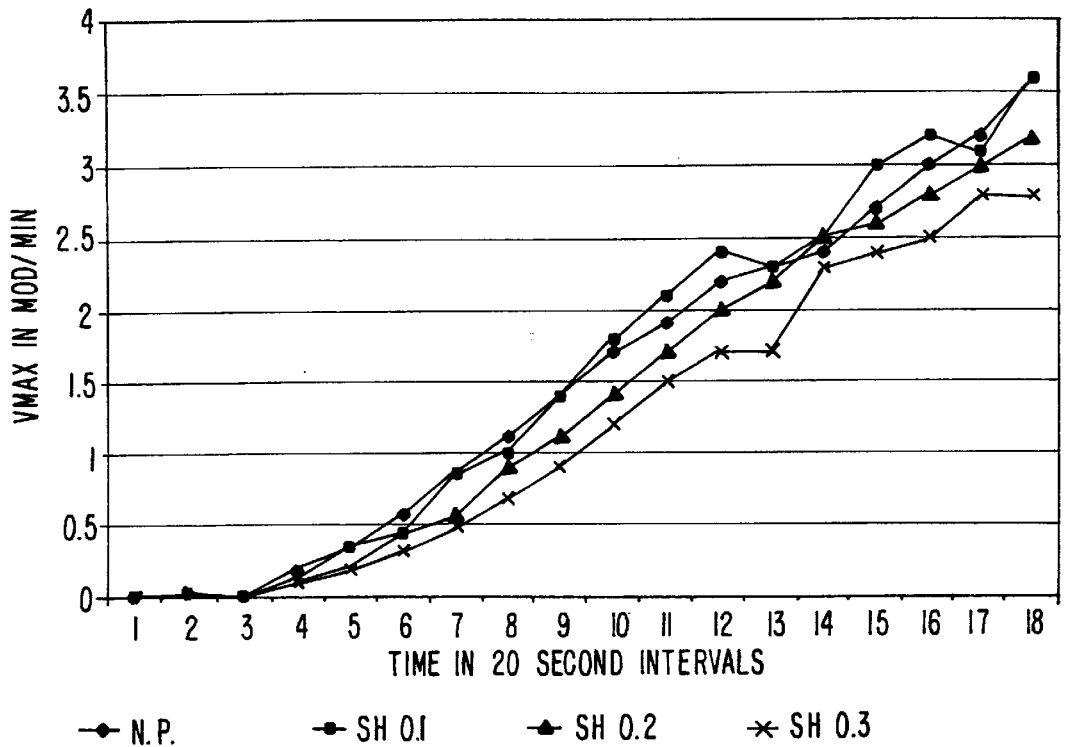
FIGS. 19a and 19b illustrate that heparin only minimally impairs Factor Xa generation triggered by Factor IXa (FIG. 19a) or Factor XIa (FIG. 19b) addition to ATIII-depleted plasma.
Figure 19B:
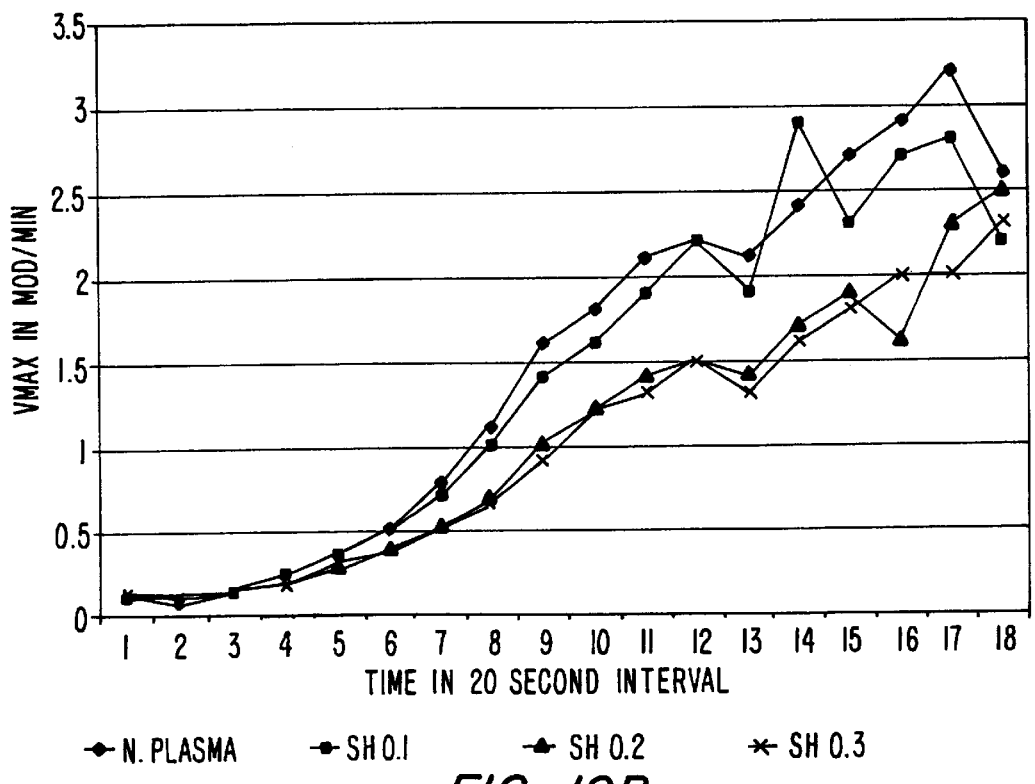
Figure 20A:
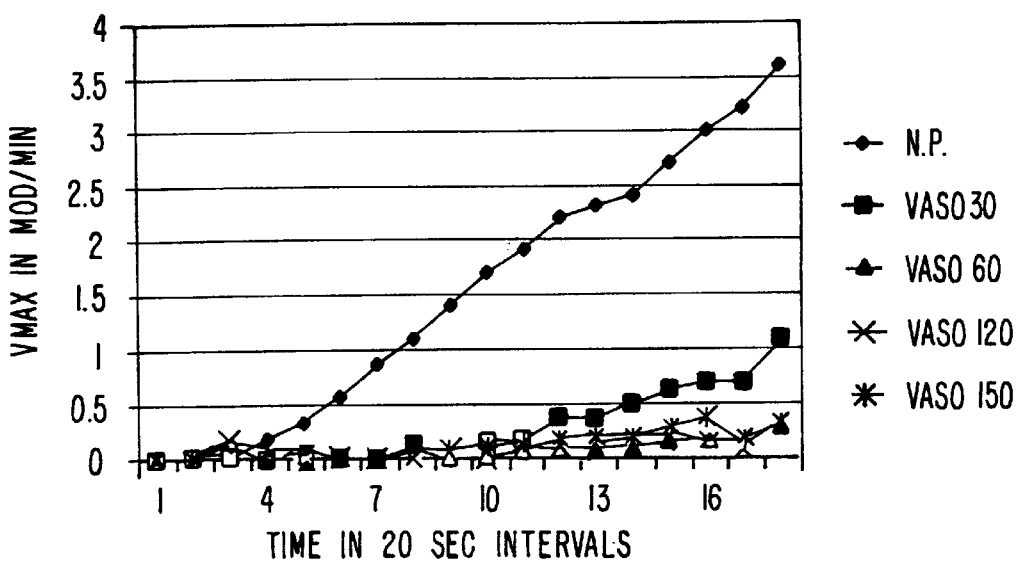
FIGS. 20a and 20b illustrate that in contrast to heparin, V18 inhibits Factor Xa generation triggered by either Factor IXa (FIG. 20a) or Factor XIa (FIG. 20b) addition to ATIII-depleted plasma.
Figure 20B:
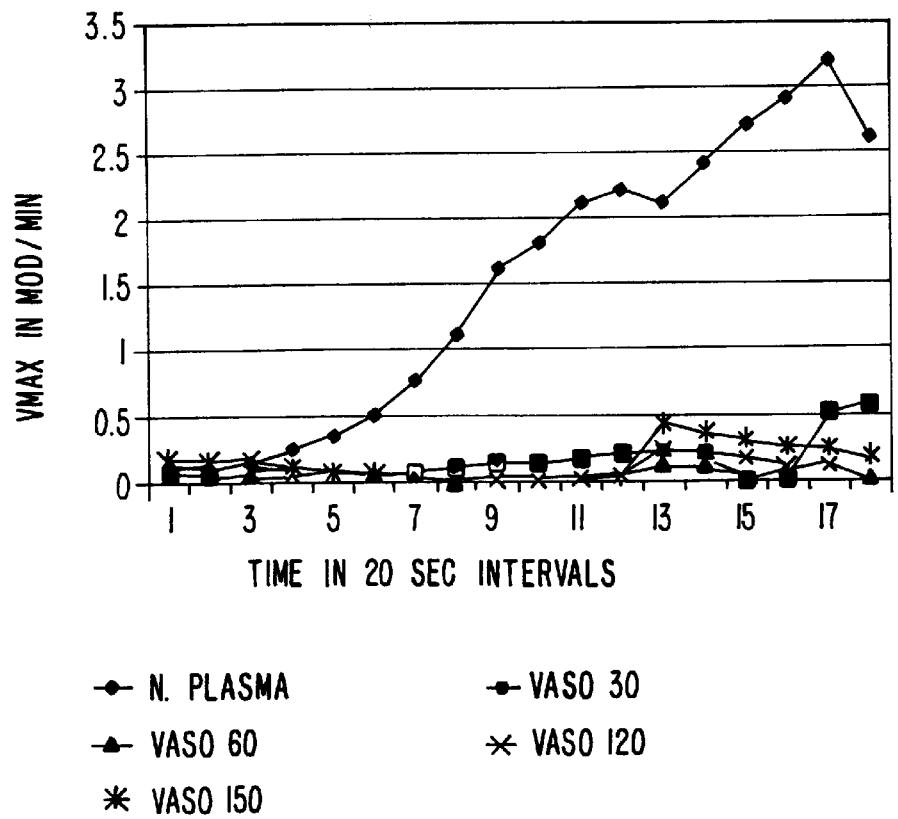

Further experiments were performed to study the mechanism of the ability of V18 to impair the assembly of intrinsic tenase. Factor IXa or Factor XIa were added to plasma immunodepleted of prothrombin (to prevent thrombin generation and subsequent clotting) and the rate of Factor Xa generation was recorded. An anti-ATIII antibody also was added to prevent the rapid inactivation of Factor Xa as it was generated. FIG. 19 illustrates that heparin produced only minimal impairment of Factor Xa generation when clotting was initiated by addition of either Factor IXa (see, FIG. 19a) or Factor XIa (see, FIG. 19b). In contrast, V18 had a marked inhibitory effect on Factor Xa generation induced by either Factor IXa or Factor XIa (see, FIGS. 20a and 20b). These findings confirm the marked ATIII-independent inhibitory effect of V18 on Factor IXa activity, support the results of experiments on intrinsic tenase assembly in a buffer system, and provide an explanation for the prolongation of the APTT by V18.

The interference of V18 with intrinsic tenase assembly is very important because it confers the compound with the ability to "passivate" activated platelets, in addition to its ability to inactivate thrombin bound to fibrin, i.e., clot-bound thrombin.

C. Mechanism 3: Inhibition of Factor IXa and XIa by V18

Figure 21A:
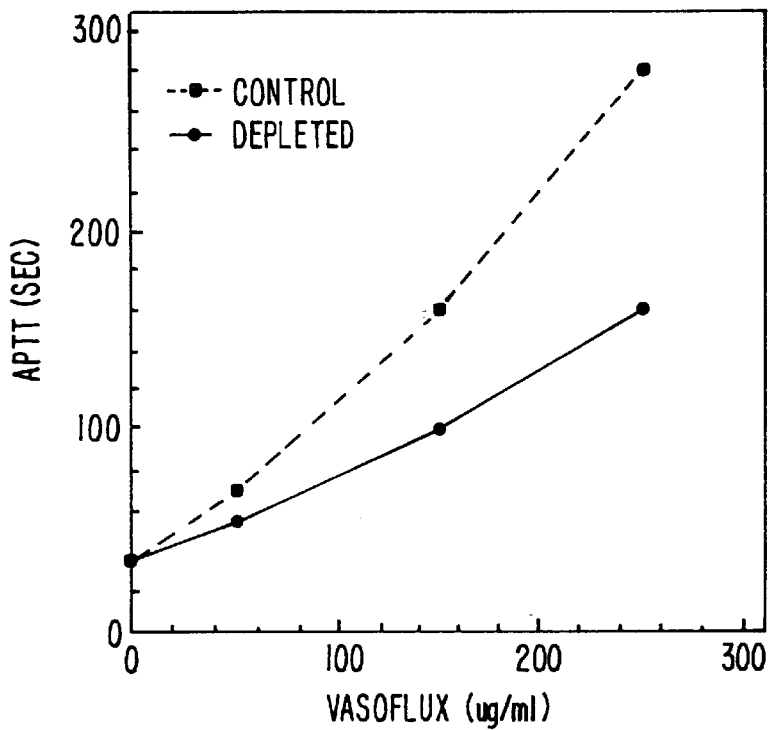
FIGS. 21a and 21b illustrate the effects of V18 and heparin, respectively, on the APTT in control plasma or in plasma depleted of both ATIII and HCII.
Figure 21B:
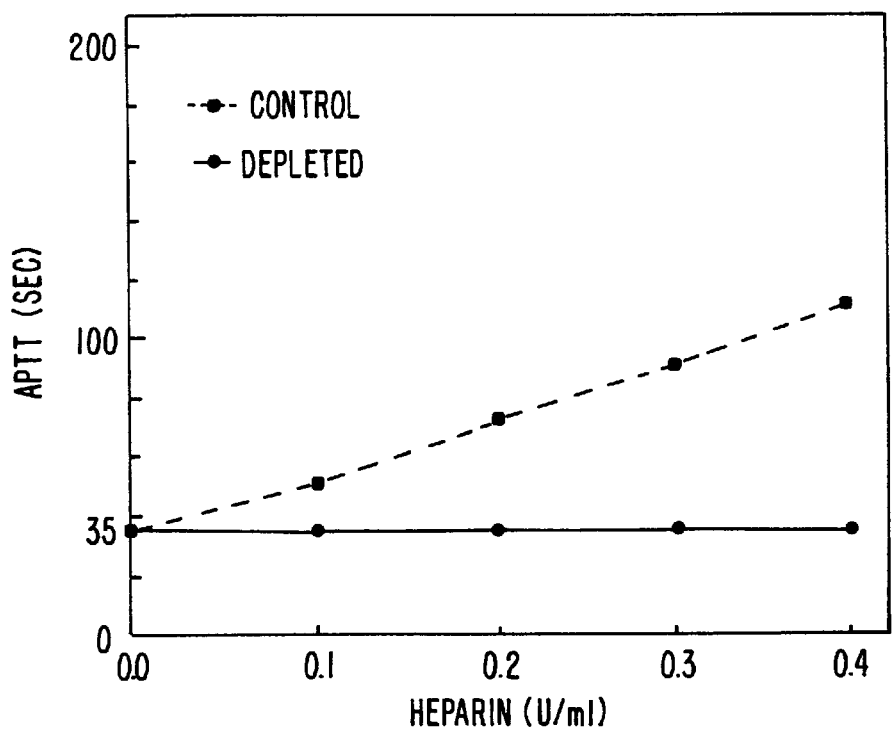

During the course of the studies carried out to characterize the effects of V18 on coagulation, an unexpected and novel observation was made. Quite surprisingly, it was discovered that V18 prolongs the APTT without exhibiting appreciable anti-factor Xa or anti-thrombin activity. Subsequently, it was demonstrated that this effect on the APTT was to a large extent independent of HCII and ATIII. Thus, V18 is able to prolong the APTT in plasma depleted of HCII and ATIII (see, FIG. 21a). In contrast, heparin is unable to inactive in the APTT assay when double depleted plasma is used (See, FIG. 21b). Further studies demonstrated that V18 could interfere with the assembly of intrinsic tenase on phospholipid surfaces, thereby explaining some (but not all) of the ATIII- and HCII-independent effects of V18 on the APTT.

Figure 22A:
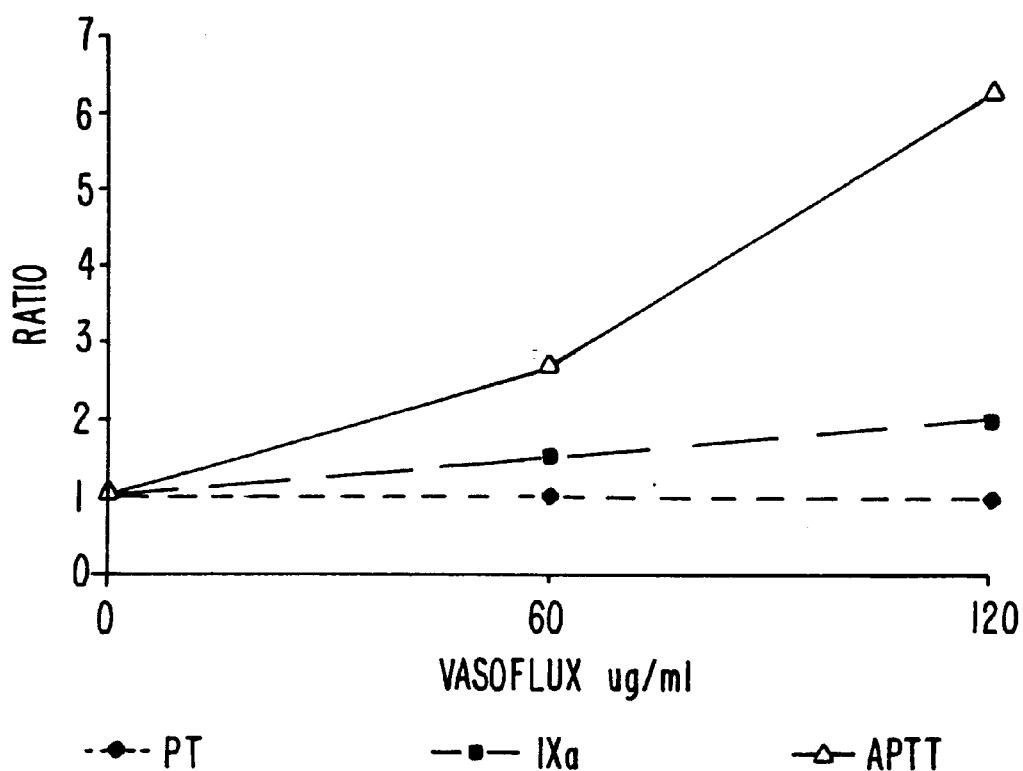
FIGS. 22a and 22b illustrate the effects of V18 and heparin, respectively, on the dilute PT, Factor IXa clotting time and APTT.
Figure 22B:
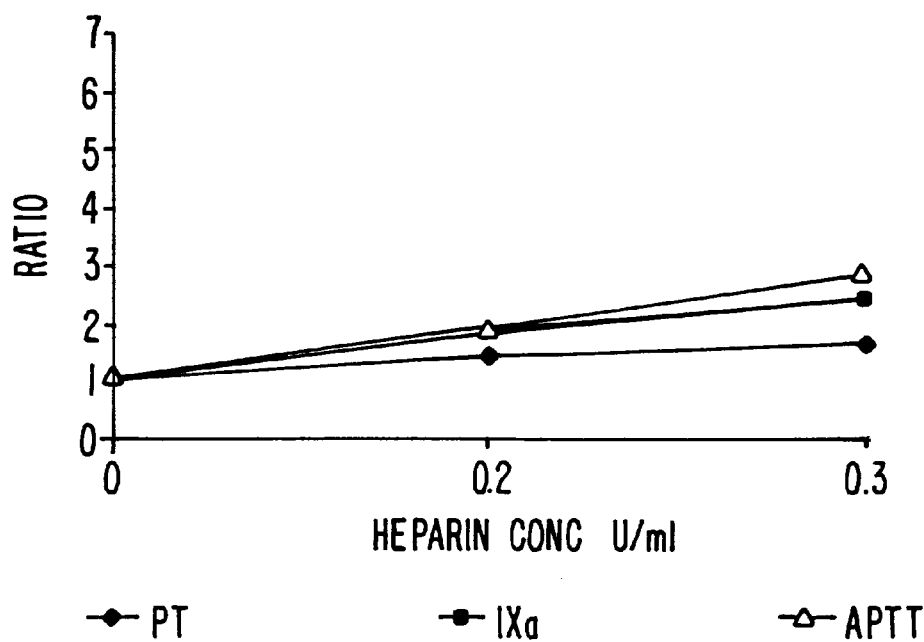

The interference of V18 with the contact activation is illustrated in FIG. 22. Thus, in contrast to heparin which has a similar effect on the IXa clotting time and APTT, V18 has a much greater effect on the APTT than the Factor IXa clotting time. The difference between the APTT and the Factor IXa clotting time represents the effect of contact activation. Included in the figure are the effects of these two antithrombotic agents on the dilute PT assay. Whereas heparin prolongs the dilute PT to a ratio of about 1.5, V18 has no effect of the dilute PT even though it prolongs the Factor IXa clotting time about two fold and has a marked effect on the APTT.

Thus, V18, a compound that is highly effective in arterial thrombosis models, has at least three very important and advantageous mechanisms of action. The first is directed against clot-bound thrombin; the second is directed against the intrinsic tenase complex; and the third is directed against contact activation. None of these actions would be expected to perturb hemostasis (which is mediated by exposure of blood to tissue factor and collagen on the surface of the severed vessel). Therefore, by modulating fibrin-bound thrombin, Factor Xa generation on the surface of activated platelets and Factor IX activation, V18 is very effective in the treatment of arterial thrombosis.

D. Comparison of the Extent of V18 and Heparin Binding

Figure 23:
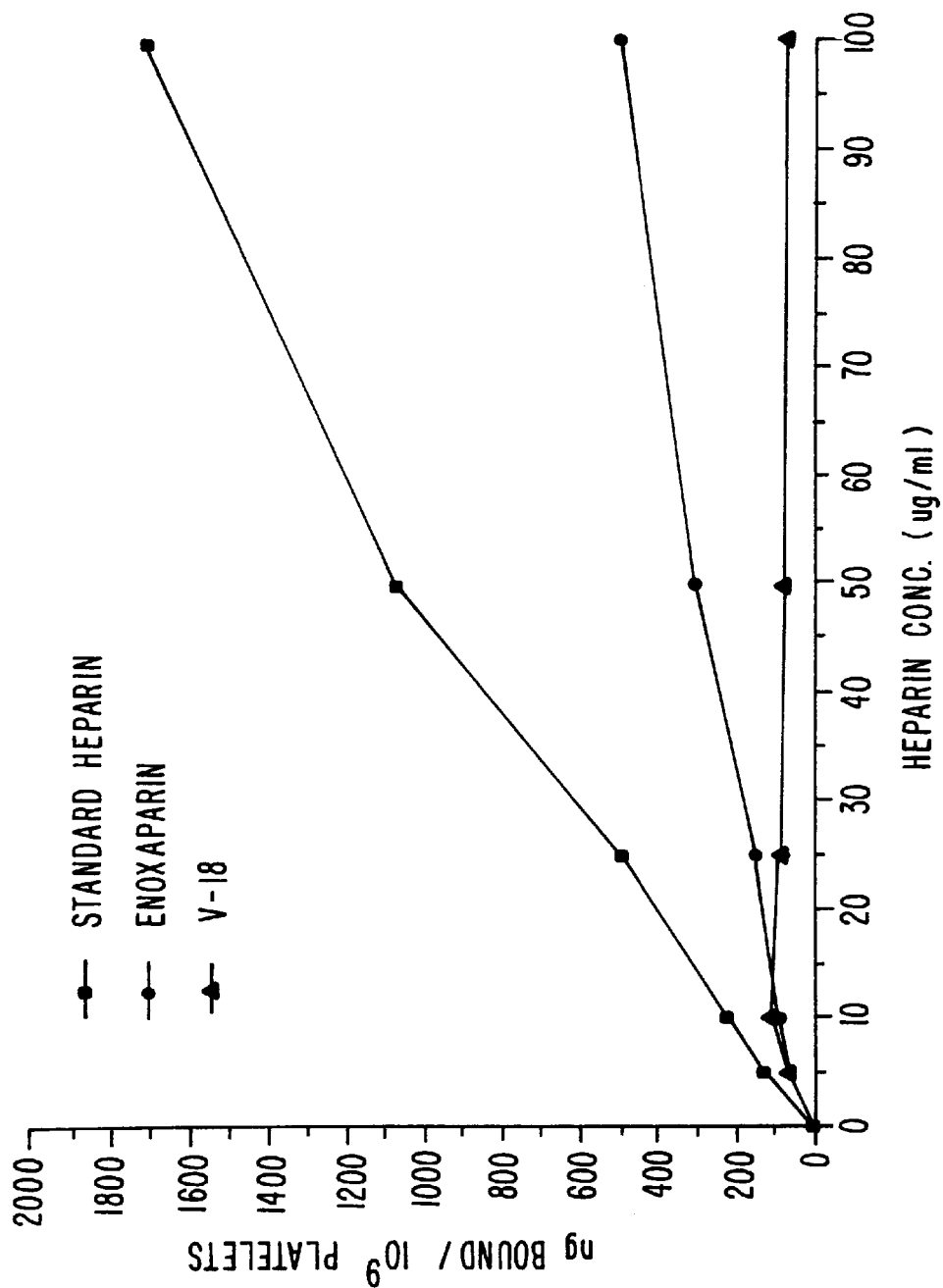
FIG. 23 compares the binding of standard heparin, LMWH and V18 to unactivated washed human platelets.
Figure 24:
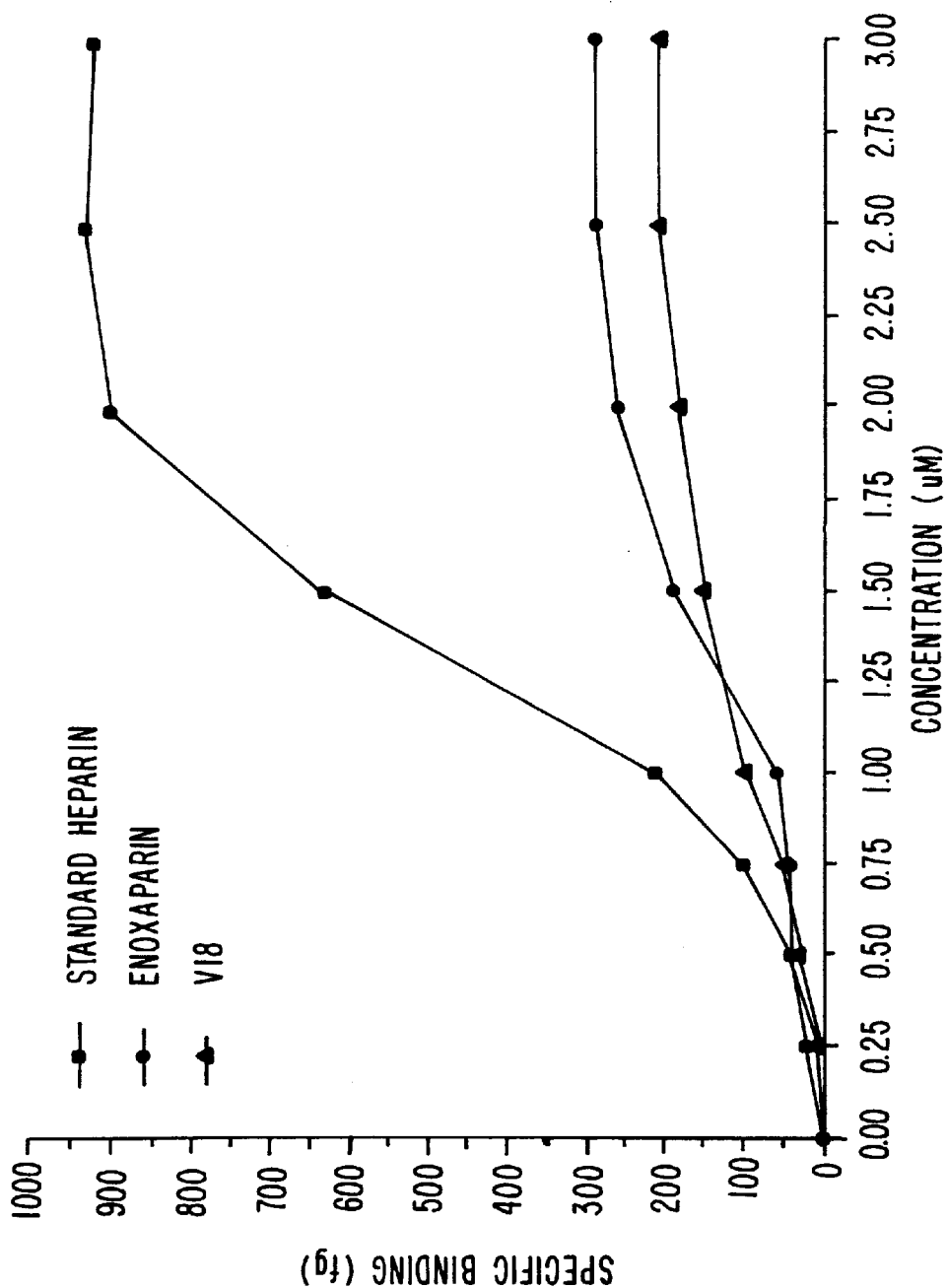
FIG. 24 compares the binding of standard heparin, LMWH and V18 to cultured human umbilical vein endothelial cells.
Figure 25:
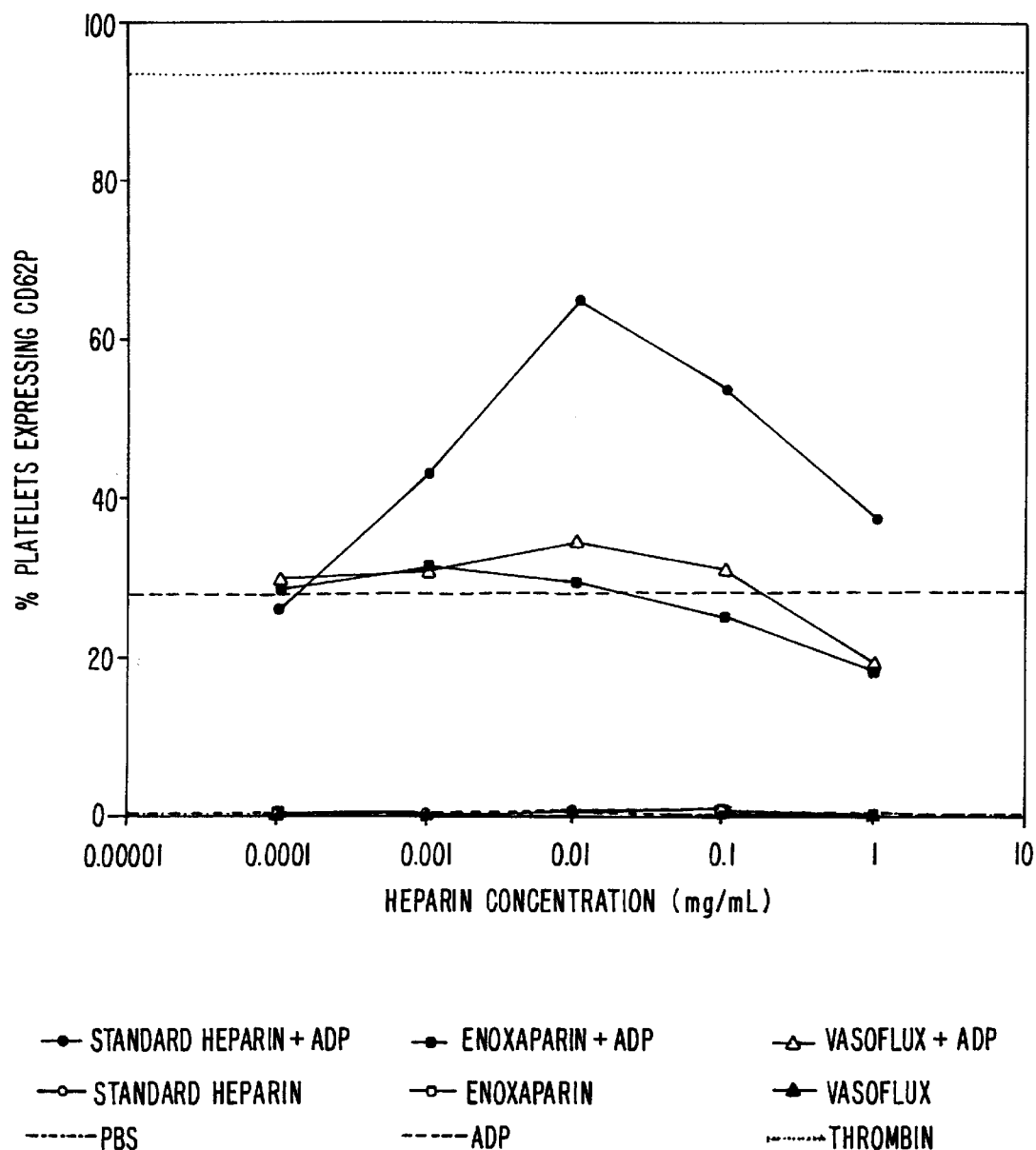
FIG. 25 compares the effect of heparin and V18 on platelet CD62P expression (a sensitive marker of platelet activation) in diluted whole blood from a human volunteer.
Figure 26:
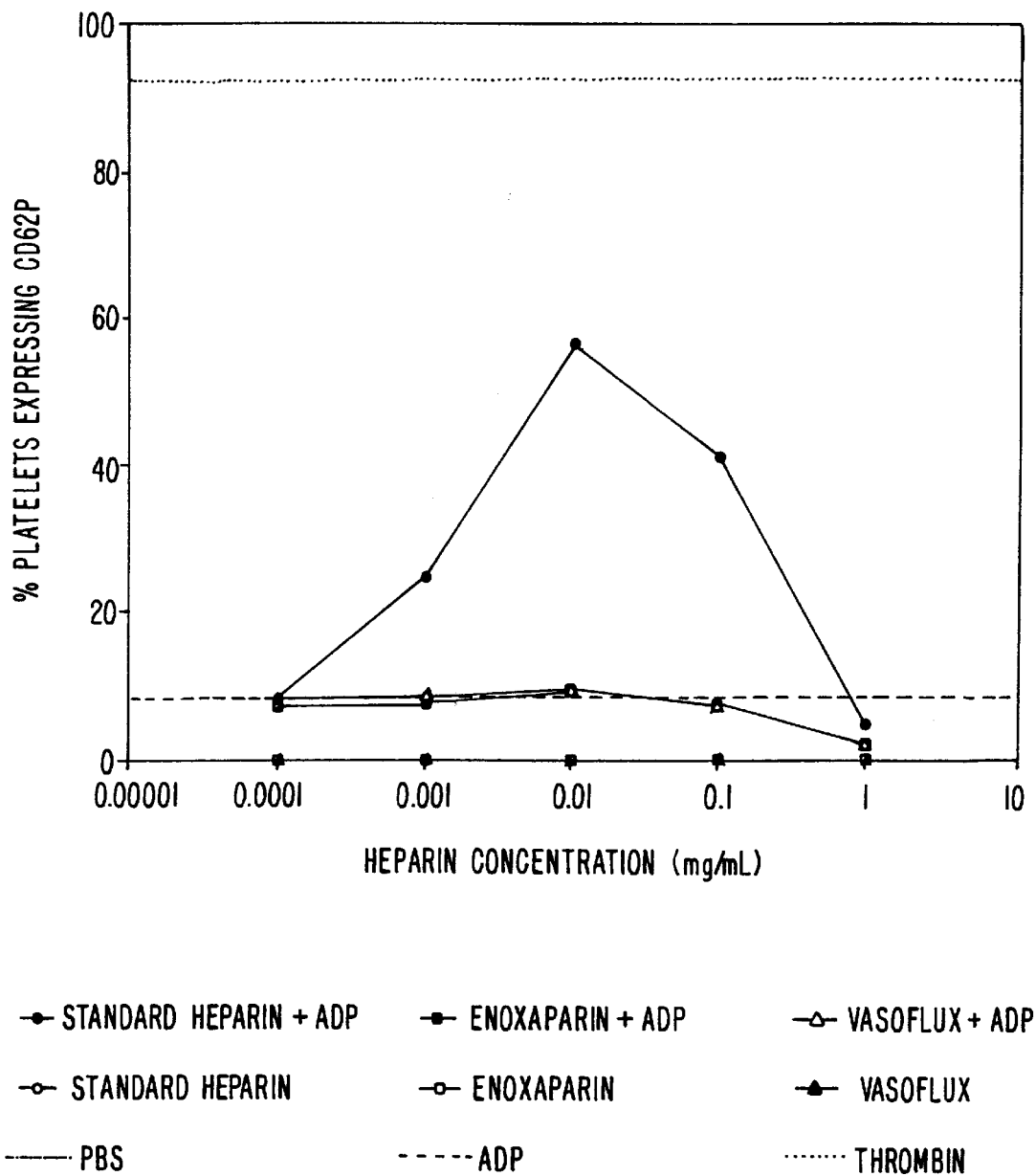
FIG. 26 compares the effect of heparin and V18 on platelet CD62P expression in diluted whole blood from a second volunteer.

The binding of V18 and heparin to platelets and endothelial cells was studied. The results of experiments using radiolabelled GAGs indicate that V18 binds less to platelets than heparin (see, FIG. 23) and endothelial cells (see, FIG. 24). Further experiments were performed to determine whether the binding of V18 and heparin to platelets causes platelet activation. Platelet activation was measured by using FACS analysis to monitor CD62P expression on the platelet surface. The results shown in FIGS. 25 and 26 indicate that heparin augments ADP-mediated platelet activation, whereas V18 does not augment platelet activation.

It is to be understood that the above description is intended to be illustrative and not restrictive. Many embodiments will be apparent to those of skill in the art upon reading the above description. The scope of the invention should, therefore, be determined not with reference to the above description, but should instead be determined with reference to the appended claims, along with the full scope of equivalents to which such claims are entitled. The disclosures of all articles and references, including patent applications and publications, are incorporated herein by reference for all purpose.

What is claimed is:

1. A method for inhibiting assembly of the intrinsic tenase complex in a mammal, said method comprising administering to said mammal an anticoagulantly effective amount of a heparin cofactor II-specific (HCII-specific) catalytic agent, said HCII-specific catalytic agent having:
   (i) a heparin cofactor II specific activity against heparin cofactor II of about 2 to about 5 units/mg in an anti-factor IIa assay;
   (ii) an antithrombin III (ATIII) specific activity against factor Xa of about 0.2 to about 1.5 units/mg in an anti-factor Xa assay; and
   (iii) a solubility in aqueous media ranging from about 150 to about 1,000 mg/ml
wherein said HC-II-specific catalytic agent is a polyanionic carbohydrate of about 10 to about 24 monosaccharide units.

2. A method of claim 1, wherein said HCII-specific catalytic agent has an antithrombin III affinity of less than about 3% of that of unfractionated heparin.

3. A method of claim 1, wherein said HCII-specific catalytic agent has an anticoagulant effect which is contributed to by both an HCII- and ATIII-mediated mechanism, and by a mechanism which is independent of both HCII and ATIII.

4. A method of claim 1, wherein said polyanionic carbohydrate is a heparin preparation having a molecular weight of between about 3,000 and about 8,000 Daltons.

5. A method of claim 4, wherein said heparin preparation consists essentially of the lowest third molecular weight fraction isolated from unfractionated heparin.

6. A method of claim 4, wherein said heparin preparation is produced from unfractionated heparin by chemically lowering the molecular weight range to between about 3,000 and about 8,000 Daltons.

7. A method of claim 6, wherein said heparin preparation has an average molecular weight of about 8,000 Daltons.

8. A method of claim 6, wherein said heparin preparation has an average molecular weight of about 5,000 Daltons.

9. A method of claim 6, wherein said heparin preparation has an average molecular weight of about 3,000 Daltons.

10. A method of claim 6, wherein the antithrombin III affinity of said heparin preparation is reduced to less than about 3% of that of the unfractionated heparin.

11. A method of claim 10, wherein said reduction in the antithrombin III affinity consists of treating the vicinal alcohol groups present in said heparin preparation with an oxidizing agent followed by a reducing agent.

12. A method of claim 11, wherein said oxidizing agent is a member selected from the group consisting of sodium periodate, dimethyl sulfoxide, acid anhydrides, lead tetraacetate and ascorbic acid, and said reducing agent is a member selected from the group consisting of sodium borohydride, lithium aluminum hydride, metal hydrides and hydrazine.

13. A method of claim 4, wherein said heparin preparation consists essentially of material without affinity for ATIII, said material is prepared by affinity purification on a solid phase to which ATIII is immobilized and the effluent retained.

14. A method of claim 1, wherein said HCII-specific catalytic agent has the formula:

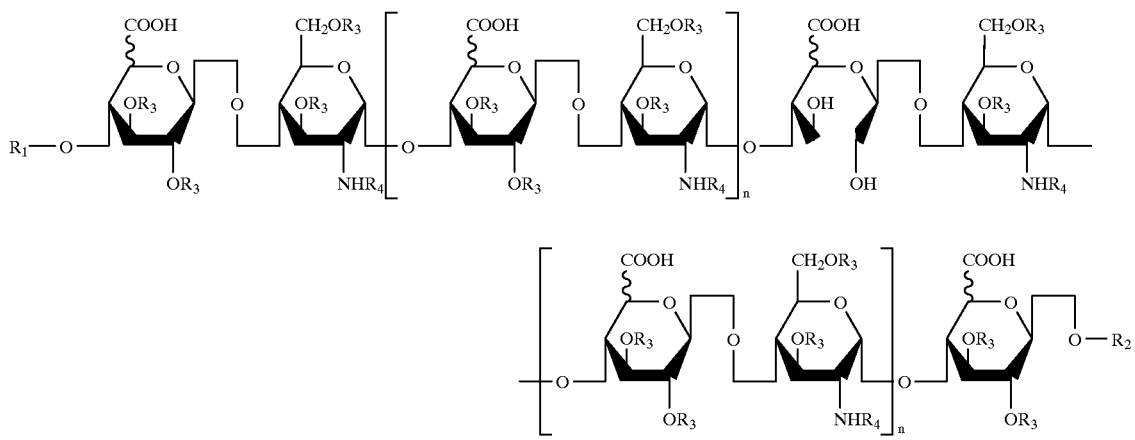

in which:

$R_1$ is a member selected from the group consisting of H, D-glucosamine acid residue, D-glucuronic acid residue and L-iduronic acid residue;

$R_2$ is a member selected from the group consisting of H, D-glucosamine acid residue, D-glucuronic acid residue, L-iduronic acid residue and anhydromannitol;

$R_3$ is a member selected from the group consisting of H and $SO_3^-$;

$R_4$ is a member selected from the group consisting of H, $SO_3^-$ and $CH_3CO^-$; and the n indexes are independently selected and can have values ranging from 0 to about 14 wherein:

said HCII-specific catalytic agent has a molecular weight ranging from about 3,000 Daltons to about 8,000 Daltons.

15. A method of claim 1, wherein said HCII-specific catalytic agent has the formula:

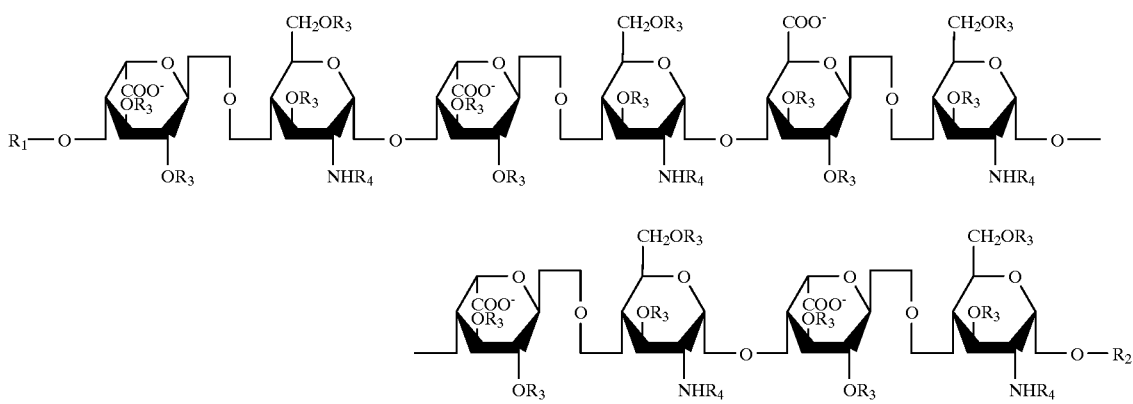

in which:

R₁ and R₂ are members independently selected from the group consisting of H, D-glucosamine acid residue, D-glucuronic acid residue and L-iduronic acid residue;

R₃ is a member selected from the group consisting of H and $SO_3^-$; and

R₄ is a member selected from the group consisting of H, $SO_3^-$ and $CH_3CO^-$;

wherein:

said HCII-specific catalytic agent has a molecular weight ranging from about 3,000 Daltons to about 8,000 Daltons.

16. A method of claim 1, wherein said HCII-specific catalytic agent has a heparin cofactor II specific activity of at least about 3 to about 4 units/mg in anti-factor IIa activity.

17. A method of claim 1, wherein said HCII-specific catalytic agent has an ATIII specific activity of about 1.0 unit/mg in an anti-factor Xa assay.

18. A method of claim 1, wherein said HCII-specific catalytic agent is mixed with a heparin additive prior to patient administration.

19. A method of claim 18, wherein the weight ratio of said HCII-specific catalytic agent to said heparin additive is greater than about 2 to 1.

20. A method of claim 18, wherein said heparin additive is unfractionated heparin.

21. A method of claim 18, wherein said heparin additive is the lowest third molecular weight fraction isolated from unfractionated heparin.

22. A method of claim 1, wherein said HCII-specific catalytic agent is administered in combination with an anti-thrombolytic agent.

23. A method of claim 1, wherein said HCII-specific catalytic agent is administered in combination with an anti-platelet agent.

24. A method for inhibiting the activation of mammalian blood coagulation Factor IX by Factor XIa, said method comprising contacting a mammalian fluid with an anticoagulantly effective amount of a heparin cofactor II-specific (HCII-specific) catalytic agent, said HCII-specific catalytic agent having:

(i) a heparin cofactor II specific activity against heparin cofactor II of about 2 to about 5 units/mg in an anti-factor IIa assay;

(ii) an antithrombin III (ATIII) specific activity against factor Xa of about 0.2 to about 1.5 units/mg in an anti-factor Xa assay; and (iii) a solubility in aqueous media ranging from about 150 to about 1,000 mg/ml wherein said HC-II-specific catalytic agent is a polyanionic carbohydrate of about 10 to about 24 monosaccharide units.

25. A method of claim 24, wherein said HCII-specific catalytic agent has an antithrombin III affinity of less than about 3% of that of unfractionated heparin.

26. A method of claim 24, wherein said HCII-specific catalytic agent has an anticoagulant effect which is contributed to by both an HCII- and ATIII-mediated mechanism, and by a mechanism which is independent of both HCII and ATIII.

27. A method of claim 24, wherein said polyanionic carbohydrate is a heparin preparation having a molecular weight of between about 3,000 and about 8,000 Daltons.

28. A method of claim 24, wherein said HCII-specific catalytic agent has the formula:

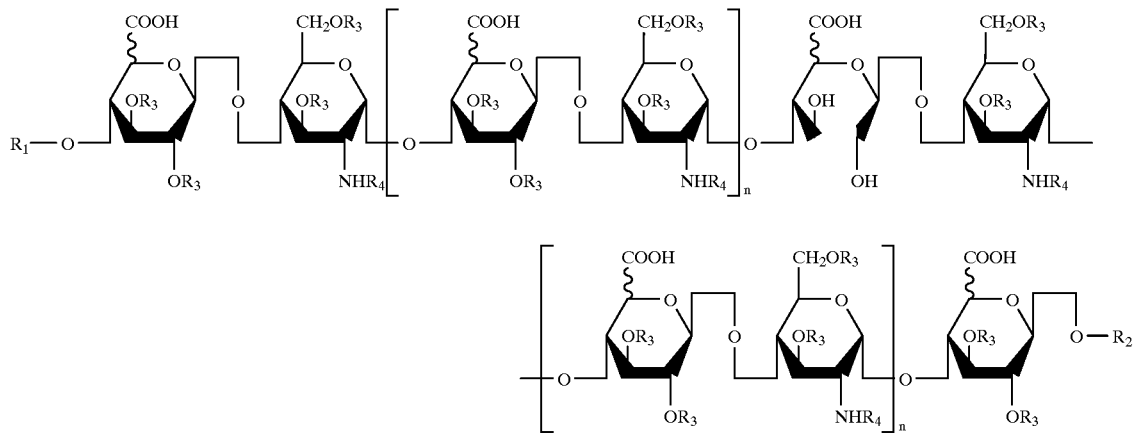

in which:

R₁ is a member selected from the group consisting of H, D-glucosamine acid residue, D-glucuronic acid residue and L-iduronic acid residue;

R₂ is a member selected from the group consisting of H, D-glucosamine acid residue, D-glucuronic acid residue, L-iduronic acid residue and anhydromannitol;

R₃ is a member selected from the group consisting of H and $SO_3^-$;

R₄ is a member selected from the group consisting of H, $SO_3^-$ and $CH_3CO^-$; and the n indexes are independently selected and can have values ranging from 0 to about 14 wherein:

said HCII-specific catalytic agent has a molecular weight ranging from about 3,000 Daltons to about 8,000 Daltons.

29. A method of claim 24, wherein said HCII-specific catalytic agent has the formula:

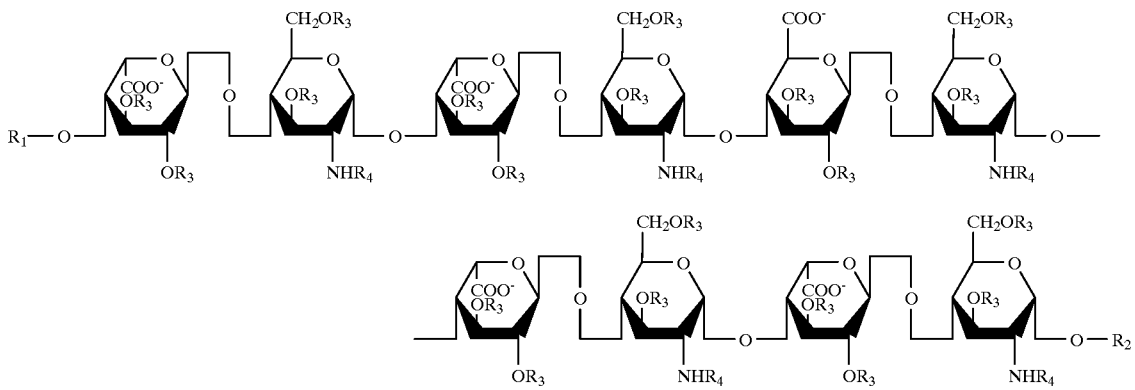

in which:
R$_1$ and R$_2$ are members independently selected from the group consisting of H, D-glucosamine acid residue, D-glucuronic acid residue and L-iduronic acid residue;
R$_3$ is a member selected from the group consisting of H and SO$_3^-$; and
R$_4$ is a member selected from the group consisting of H, SO$_3^-$ and CH$_3$CO$^-$;
wherein:
said HCII-specific catalytic agent has a molecular weight ranging from about 3,000 Daltons to about 8,000 Daltons.

30. A method of claim 24, wherein said HCII-specific catalytic agent has a heparin cofactor II specific activity of at least about 3 to about 4 units/mg in anti-factor IIa activity.

31. A method of claim 24, wherein said HCII-specific catalytic agent has an ATIII specific activity of about 1.0 unit/mg in an anti-factor Xa assay.

32. A method of claim 24, wherein said HCII-specific catalytic agent is mixed with a heparin additive prior to patient administration.

33. A method of claim 24, wherein said HCII-specific catalytic agent is administered in combination with an anti-thrombolytic agent.

34. A method of claim 24, wherein said HCII-specific catalytic agent is administered in combination with an anti-platelet agent.

35. A method for inhibiting activation of blood coagulation Factor X by Factor IXa in a mammal, said method comprising administering to said mammal an anticoagulantly effective amount of a heparin cofactor II-specific (HCII-specific) catalytic agent, said HCII-specific catalytic agent having:
(i) a heparin cofactor II specific activity against heparin cofactor II of about 2 to about 5 units/mg in an anti-factor IIa assay;
(ii) an antithrombin III (ATIII) specific activity against factor Xa of about 0.2 to about 1.5 units/mg in an anti-factor Xa assay; and
(iii) a solubility in aqueous media ranging from about 150 to about 1,000 mg/ml
wherein said HC-II-specific catalytic agent is a polyanionic carbohydrate of about 10 to about 24 monosaccharide units.

36. A method of claim 35, wherein said HCII-specific catalytic agent has an antithrombin III affinity of less than about 3% of that of unfractionated heparin.

37. A method of claim 35, wherein said HCII-specific catalytic agent has an anticoagulant effect which is contributed to by both an HCII- and ATIII-mediated mechanism, and by a mechanism which is independent of both HCII and ATIII.

38. A method of claim 35, wherein said polyanionic carbohydrate is a heparin preparation having a molecular weight of between about 3,000 and about 8,000 Daltons.

39. A method of claim 35, wherein said HCII-specific catalytic agent has the formula:

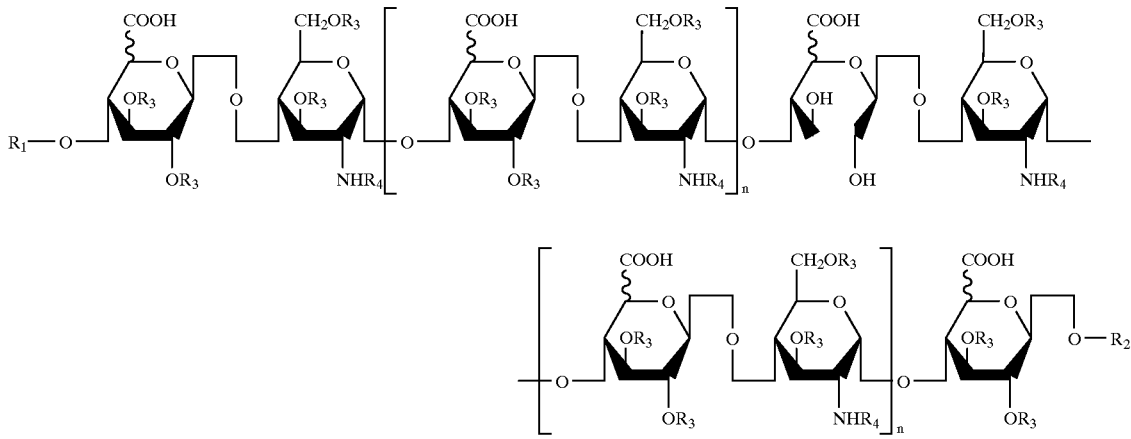

in which:

R₁ is a member selected from the group consisting of H, D-glucosamine acid residue, D-glucuronic acid residue and L-iduronic acid residue;

R₂ is a member selected from the group consisting of H, D-glucosamine acid residue, D-glucuronic acid residue, L-iduronic acid residue and anhydromannitol;

R₃ is a member selected from the group consisting of H and $SO_3^-$;

R₄ is a member selected from the group consisting of H, $SO_3^-$ and $CH_3CO^-$; and the n indexes are independently selected and can have values ranging from 0 to about 14 wherein:

said HCII-specific catalytic agent has a molecular weight ranging from about 3,000 Daltons to about 8,000 Daltons.

40. A method of claim 35, wherein said HCII-specific catalytic agent has the formula:

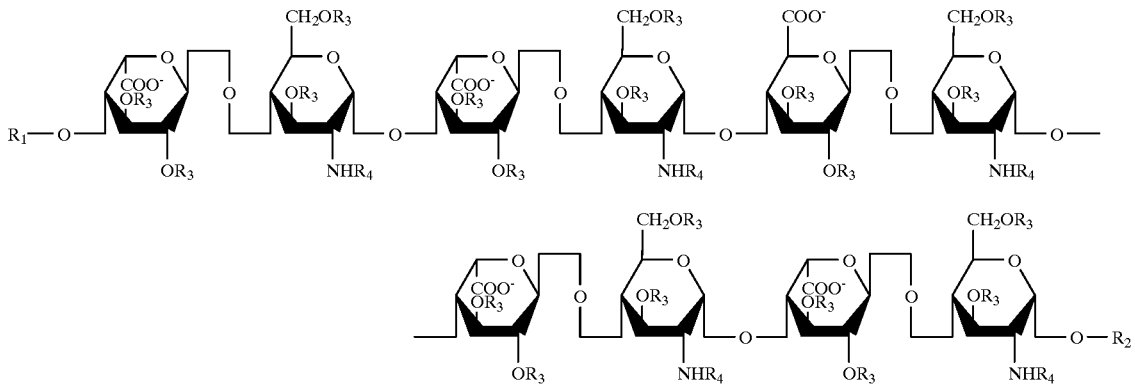

in which:

R₁ and R₂ are members independently selected from the group consisting of H, D-glucosamine acid residue, D-glucuronic acid residue and L-iduronic acid residue;

R₃ is a member selected from the group consisting of H and $SO_3^-$; and

R₄ is a member selected from the group consisting of H, $SO_3^-$ and $CH_3CO^-$;

wherein:

said HCII-specific catalytic agent has a molecular weight ranging from about 3,000 Daltons to about 8,000 Daltons.

41. A method of claim 35, wherein said HCII-specific catalytic agent has a heparin cofactor II specific activity of at least about 3 to about 4 units/mg in anti-factor IIa activity.

42. A method of claim 35, wherein said HCII-specific catalytic agent has an ATIII activity of about 1.0 unit/mg in an anti-factor Xa assay.

43. A method of claim 35, wherein said HCII-specific catalytic agent is mixed with a heparin additive prior to patient administration.

44. A method of claim 35, wherein said HCII-specific catalytic agent is administered in combination with an anti-thrombolytic agent.

45. A method of claim 35, wherein said HCII-specific catalytic agent is administered in combination with an anti-platelet agent.

* * * * *